US008357705B2

(12) United States Patent  
Zemolka et al.

(10) Patent No.: US 8,357,705 B2  
(45) Date of Patent: Jan. 22, 2013

(54) SUBSTITUTED CYCLOHEXYLDIAMINES

(75) Inventors: Saskia Zemolka, Aachen (DE); Bert Nolte, Aachen (DE); Klaus Linz, Wachtberg (DE); Derek John Saunders, Aachen (DE); Wolfgang Schröder, Aachen (DE); Werner Englberger, Stolberg (DE); Fritz Theil, Berlin (DE); Hans Schick, Berlin (DE); Jens Kaufmann, Berlin (DE); Julian Gebauer, Berlin (DE); Helmut Sonnenschein, Berlin (DE)

(73) Assignee: Gruenenthal GmbH, Aachen (DE)

( * ) Notice: Subject to any disclaimer, the term of this patent is extended or adjusted under 35 U.S.C. 154(b) by 366 days.

(21) Appl. No.: 12/410,923

(22) Filed: Mar. 25, 2009

(65) Prior Publication Data  
US 2009/0247591 A1 Oct. 1, 2009

(30) Foreign Application Priority Data

Mar. 27, 2008 (EP) .................................... 08005759

(51) Int. Cl.  
*A61K 31/41* (2006.01)  
*C07D 271/12* (2006.01)

(52) U.S. Cl. ........ 514/364; 514/381; 514/415; 548/131; 548/144; 548/253; 548/507

(58) Field of Classification Search .................. 514/364, 514/381, 415; 548/131, 144, 253, 507  
See application file for complete search history.

(56) References Cited

U.S. PATENT DOCUMENTS

| | | | |
|---|---|---|---|
| 3,328,412 A | 6/1967 | Atkinson et al. | |
| 4,065,573 A | 12/1977 | Lednicer | |
| 4,115,589 A | 9/1978 | Lednicer | |
| 4,291,039 A | 9/1981 | Van Dyke, Jr. et al. | |
| 4,366,172 A | 12/1982 | Lednicer | |
| 4,575,508 A | 3/1986 | Steiner et al. | |
| 5,328,905 A | 7/1994 | Hamminga et al. | |
| 5,631,265 A | 5/1997 | Audia et al. | |
| 5,760,051 A | 6/1998 | Audia et al. | |
| 5,869,691 A | 2/1999 | Audia et al. | |
| 6,998,409 B2 | 2/2006 | Sundermann et al. | |
| 7,276,518 B2 | 10/2007 | Sundermann et al. | |
| 7,332,519 B2 | 2/2008 | Hinze et al. | |
| 7,485,634 B2 | 2/2009 | Martin et al. | |
| 7,507,758 B2 | 3/2009 | Sundermann et al. | |
| 7,547,707 B2 | 6/2009 | Hinze et al. | |
| 7,595,311 B2 | 9/2009 | Busch et al. | |
| 7,799,931 B2 | 9/2010 | Hinze et al. | |
| 7,960,404 B2 | 6/2011 | Schunk et al. | |
| 7,977,370 B2 | 7/2011 | Zemolka et al. | |
| 8,053,576 B2 | 11/2011 | Hinze et al. | |
| 8,133,992 B2 | 3/2012 | Martin et al. | |
| 8,143,257 B2 | 3/2012 | Choi et al. | |
| 2003/0236250 A1 | 12/2003 | Pineiro et al. | |
| 2004/0023947 A1 | 2/2004 | Martin et al. | |
| 2005/0192333 A1 | 9/2005 | Hinze et al. | |
| 2005/0267107 A1 | 12/2005 | Sundermann et al. | |
| 2006/0004034 A1 | 1/2006 | Hinze et al. | |
| 2006/0235012 A1 | 10/2006 | Davidson et al. | |
| 2007/0149557 A1 | 6/2007 | Collins et al. | |
| 2008/0125475 A1 | 5/2008 | Linz et al. | |
| 2008/0221141 A1 | 9/2008 | Friderichs et al. | |
| 2008/0261956 A1 | 10/2008 | Choi et al. | |
| 2008/0280942 A1 | 11/2008 | Diaz-Fernandez et al. | |
| 2009/0042866 A1 | 2/2009 | Lennox et al. | |
| 2009/0156626 A1 | 6/2009 | Hinze et al. | |
| 2009/0163716 A1 | 6/2009 | Hinze et al. | |
| 2009/0247505 A1 | 10/2009 | Zemolka et al. | |
| 2009/0247530 A1 | 10/2009 | Nolte et al. | |
| 2009/0247561 A1 | 10/2009 | Zemolka et al. | |
| 2009/0247573 A1 | 10/2009 | Zemolka et al. | |
| 2009/0247591 A1 | 10/2009 | Zemolka et al. | |
| 2009/0326218 A1 | 12/2009 | Martin et al. | |
| 2010/0009986 A1 | 1/2010 | Zemolka et al. | |
| 2010/0048553 A1 | 2/2010 | Schunk et al. | |
| 2010/0048554 A1 | 2/2010 | Schunk et al. | |
| 2010/0173824 A1 | 7/2010 | Busch et al. | |
| 2011/0015220 A1 | 1/2011 | Linz et al. | |
| 2011/0059999 A1 | 3/2011 | Frormann et al. | |

FOREIGN PATENT DOCUMENTS

| | | |
|---|---|---|
| AR | 071066 | 5/2010 |
| AR | 071067 | 5/2010 |
| AR | 071068 | 5/2010 |
| AR | 073841 | 12/2010 |
| AU | 2009228637 | 10/2009 |
| AU | 2009228642 | 10/2009 |
| AU | 2009228643 | 10/2009 |
| AU | 2009228645 | 10/2009 |
| AU | 2009228647 | 10/2009 |
| AU | 2009228648 | 10/2009 |
| CA | 2446461 A1 | 11/2002 |
| CA | 2550868 A1 | 7/2005 |
| CA | 2658376 A1 | 1/2008 |
| CA | 2658379 A1 | 1/2008 |

(Continued)

OTHER PUBLICATIONS

Reinscheid, et al, "Orphanin FQ: A Neuropepetide that Activates an Opioidlike G Protein-Coupled Receptor", Science, vol. 270, Nov. 3, 1995, pp. 792-794.

Meunier, et al, "Isolation and structure of the endogenous agonist of opioid receptor-like ORL1 receptor", Nature, vol. 377, Oct. 12, 1995, pp. 532-535.

Mogil, et al, "Orphanin FQ is a Functional Anti-Opioid Peptide"; Neuroscience, vol. 75, No. 2, 1996, pp. 333-337.

Jenck, et al, "Orphanin FQ acts as an anxiolytic to attenuate behavioral responses to stress"; Proc. Natl. Acad. Sci. USA, vol. 94, Dec. 1997, pp. 14854-14858.

(Continued)

*Primary Examiner* — Porfirio Nazario Gonzalez  
(74) *Attorney, Agent, or Firm* — Norris McLaughlin & Marcus, P.A.

(57) ABSTRACT

The invention relates to compounds that have an affinity to the μ-opioid receptor and the ORL 1-receptor, methods for their production, medications containing these compounds and the use of these compounds for the treatment of pain or other conditions.

7 Claims, No Drawings

FOREIGN PATENT DOCUMENTS

| | | |
|---|---|---|
| CA | 2718209 | 10/2009 |
| CA | 2719735 | 10/2009 |
| CA | 2719736 | 10/2009 |
| CA | 2719739 | 10/2009 |
| CA | 2719742 | 10/2009 |
| CA | 2719743 | 10/2009 |
| CA | 2446461 C | 4/2011 |
| DE | 28 39 891 | 4/1979 |
| DE | 28 39 891 A1 | 4/1979 |
| EP | 2260022 | 10/2009 |
| EP | 2257526 | 12/2010 |
| EP | 2260021 | 12/2010 |
| EP | 2260042 | 12/2010 |
| EP | 2271613 | 1/2011 |
| EP | 2280941 | 2/2011 |
| GB | 1 055 203 | 1/1967 |
| KR | 20100132048 | 12/2010 |
| KR | 20100136521 | 12/2010 |
| MX | 2010009955 | 9/2010 |
| MX | 2010010337 | 10/2010 |
| MX | 2010010339 | 10/2010 |
| MX | 2010010407 | 10/2010 |
| MX | 2010010446 | 11/2010 |
| MX | 2010010448 | 11/2010 |
| PE | 16502009 | 11/2009 |
| PE | 16572009 | 11/2009 |
| PE | 18222009 | 12/2009 |
| PE | 18232009 A1 | 12/2009 |
| PE | 16892009 | 11/2011 |
| WO | 01 87838 | 11/2001 |
| WO | 02 90330 | 5/2002 |
| WO | 02 090317 | 11/2002 |
| WO | 02090317 A1 | 11/2002 |
| WO | 03 008370 | 1/2003 |
| WO | 03 008731 | 1/2003 |
| WO | 03 080557 | 1/2003 |
| WO | 2004 043899 | 5/2004 |
| WO | 2004 043900 | 5/2004 |
| WO | 2004 043902 | 5/2004 |
| WO | 2004 043909 | 5/2004 |
| WO | 2004 043949 | 5/2004 |
| WO | 2004 043967 | 5/2004 |
| WO | 2005 063769 | 7/2005 |
| WO | 2005 066183 | 7/2005 |
| WO | 2005 110970 | 11/2005 |
| WO | 2005 110971 | 11/2005 |
| WO | 2005 110973 | 11/2005 |
| WO | 2005 110974 | 11/2005 |
| WO | 2005 110975 | 11/2005 |
| WO | 2005 110976 | 11/2005 |
| WO | 2005 110977 | 11/2005 |
| WO | 2006 018184 | 2/2006 |
| WO | 2006058088 | 6/2006 |
| WO | 2006065479 | 6/2006 |
| WO | 2006065480 | 6/2006 |
| WO | 2006 108565 | 10/2006 |
| WO | 2007 079927 | 7/2007 |
| WO | 2007 079928 | 7/2007 |
| WO | 2007 079930 | 7/2007 |
| WO | 2007 079931 | 7/2007 |
| WO | 2007 124903 | 11/2007 |
| WO | 2008 009416 | 1/2008 |
| WO | 2008009415 | 1/2008 |
| WO | 2008040481 A1 | 4/2008 |
| WO | 2008101659 A1 | 8/2008 |
| WO | 2008101660 A1 | 8/2008 |
| WO | 2009 118174 A1 | 10/2009 |
| WO | 2009118163 | 10/2009 |
| WO | 2009118163 A1 | 10/2009 |
| WO | 2009118168 | 10/2009 |
| WO | 2009118168 A1 | 10/2009 |
| WO | 2009118169 | 10/2009 |
| WO | 2009118171 | 10/2009 |
| WO | 2009118171 A1 | 10/2009 |
| WO | 2009118173 | 10/2009 |
| WO | 2009118173 A1 | 10/2009 |
| WO | 2009118174 | 10/2009 |

OTHER PUBLICATIONS

King et al, "Spinal analgesic activity of orphanin FQ/nociceptin and its fragments", Neuroscience Letters 223 (1997), pp. 113-116.

Abdulla et al, "Axotomy Reduces the Effect of Analgesic Opioids Yet Increases the Effect of Nociceptin on Dorsal Root Ganglion Neurons"; The Journal of Nosciene, Dec. 1, 1998, 18 (23), pp. 9685-9694.

Manabe et al, "Facilitation of long-term potentiation and memory in mice lacking nociceptin receptors"; Nature, vol. 394, Aug. 6, 1998, pp. 577-581.

Nishi et al, "Unrestrained nociceptive response and disregulation of hearing ability in mice lacking the nociceptin/orphaninFQ receptor"; The EMBO Journal, vol. 16, No. 8, 1997, pp. 1858-1864.

Calo, et al, "Pharmacology of nociceptin and its receptor: a novel therapeutic target"; British Journal of Pharmacology (2000) 129, pp. 1261-1283.

Bavetsias et al., "Design and Synthesis of Cyclopenta[g]quinazoline-Based Antifolates as Inhibitors of Thymidylate Synthase and Potential Antitumor Agents", J. Med. Chem, No. 43, pp. 1910-1926, (2000).

Catterall et al., "Binding of Batrachotoxinin A 20-α-Benzoate to a Receptor Site Associated with Sodium Channels in Synaptic Nerve Ending Particles", The Journal of Biological Chemistry, vol. 256, No. 17, pp. 8922-8927, Sep. 10, 1981.

Dirat et al., "Expeditious systhesis of novel NK1 antagonists based on a 1,2,4-trisubstituted cyclohexane", Tetrahedron Letters, No. 47, pp. 1295-1298, (2006).

Elliot et al., "NK1 antagonists based on seven membered lactam scaffolds", Bioorganic & Medicinal Chemistry Letters No. 16, pp. 2929-2932, (2006).

Hamzé et al., "Systhesis of Various 3-Substituted 1,2,4-Oxadiazole-Containing Chiral B3- and α-Amino Acids from Fmoc-Protected Aspartic Acid", J. Org. Chem. No. 68, pp. 7316-7321, (2003).

Hashmi et al., "Gold Catalysis: Mild Conditions for the Synthesis of Oxazoles from N-Propargylcarboxamides and Mechanistic Aspects", Organic Letters, vol. 6, No. 23, pp. 4391-4394, (2004).

Katritzky et al., "The Chemistry of N-Substituted Benzotriazoles; Part 11.1 The Preparation of Tertiary Amines Containing Tertiary-Alkyl Groups from Ketones, Secondary Amines and Organometallic Reagents", Communications, pp. 66-69, Jan. 1989.

Kim et al., "An experimental model for peripheral neuropathy produced by segmental spinal nerve ligation in the rat", Elsevier Science Publishers B.V., No. 50, pp. 355-363, (1992).

Kudzma et al., "4-Phenyl- and a 4-Heteroaryl-4-anilidopiperidines. A Novel Class of Analgesic and Anesthetic Agents1", J. Med. Chem. No. 32, pp. 2534-2542, (1989).

Layer, Robert W. "The Chemistry of Imines", B.F. Goodrich Co., Research Center, pp. 489-510; Dec. 7, 1962.

Lednicer et al., "4-Amino-4-arylcyclohexanones and Their Derivatives, a Novel Class of Analgesics. 1. Modification of the Aryl Ring", The Upjohn Company, Research Laboratories, Aug. 7, 1979.

Lee et al., "Introduction of Heterocycles at the 2-position of Indoline as Ester Bioisosteres", Bull. Koren Chem. Soc. vol. 25, No. 2 pp. 207-212, (2004).

Maddox et al., "The Synthesis of Phencyclidine and Other 1-Arylcyclohexylamines", Research Laboratories, Parke, Davis and Company; vol. 8, pp. 230-235, Mar. 1965.

Morwick et al., "A Practical Approach to the Synthesis of 2,4-Disubstituted Oxazoles from Amino Acids", Organic Letters, vol. 4, No. 16, pp. 2665-2668, (2002).

Thompson et al., "Structure-Based Design of Cathepsin K Inhibitors Containing a Benzyloxy-Substituted Benzoyl Peptidomimetic", Journal of Medical Chemistry, vol. 41, No. 21, pp. 3923-3927, (1998).

Corey et al.; Tetrahedron Letters, No. 36, 1972, pp. 3769-3772.

D'Amour et al., The Biological Research Laboratory, Jan. 27, 1941, pp. 74-79.

Harned et al.; Tetrahedron, No. 61, 2005, pp. 12093-12099.

Katritzky et al., Synthesis, Dec. 1992, pp. 1295-1298.

Prashad et al., Tetahedron LEtters, No. 46, 1005, pp. 5455-5458, (2005).

Regitz et al.; Chem. Ber., No. 101, 1968, pp. 3734-3743.

Shiner et al., J. am. Chem. Soc., 103, 1981, pp. 436-442.
Xia et al., Organic Letters, vol. 7, No. 7, 2005, pp. 1315-1318.
Messina et al., Tetrahedron, Asymmetry 11, 2000, pp. 1681-1685.
Greene et al., Protective Groups in Organic Synthesis; Wiley Interscience Publication; 3rd Edition, 1999.
Jirkovsky et al., J. Heterocycl. Chem., 12, 1975, pp. 937-940.
Beck et al., J. Chem. Soc. Perkin 1, 1992, pp. 813-822.
Shinada et al., Tetrahedron Letters, vol. 39, 1996, pp. 7099-7102.
Garden et al., Tetrahedron, 58, 2002, pp. 8399-8412.
Williams et al., J. Org. Chem. 1980, 45, pp. 5082-5088.
Bandini et al. J. Org. Chem. 67, 2002, pp. 5386-5389.
Davis et al. J. Med. Chem. 35, 1992, pp. 177-184.
Yamagishi et al., J. Med. Chem. 35, 1992, pp. 2085-2094.
Gleave et al.; Bioorganic & Medicinal Chemistry Letters 8, 1998, pp. 1231-1236.
Sandmeyer, Helv.Chim.Acta; 2; 1919; 239.
Katz et al.; J. Med. Chem. 31, 1988; pp. 1244-1250.
Bac et al. Tetrahedron Letters, 1988, vol. 29, pp. 2819-2822.
Kato et al. J. Fluorine Chemistry, 99, 1999, pp. 5-7.
Piper, et al; Journal of Medicinal Chemistry, US American Chemical Society, Washington, No. 9, Jan. 1, 1966; pp. 911-920.
Gilbert, et al; Journal of the American Chemical Society, 1950, No. 72, pp. 2411-2417.
Chu, et al.; Tetrahedron, Elsevier Science Publishers, Amsterdam, NL, No. 62, 2006, pp. 5536-5548.
Finlayson, et al., European Journal of Pharmacology, 412 (2001), pp. 203-212.
Ma et al. J. Org. Chem. 2001, 66, 4525-4542.
Lednicer et al., J. Med. Chem., 23, 1980, pp. 424-430.
Patani et al Chem rev. 1996, vol. 96, p. 3147-3176.
Rose et al, Can J. Chem., 74, 1996, 1836.
Dorwald F. A., Side reactions in Oranic Synthesis, 2005, Wiley: VCH, Weinheim p. IX of Preface.
Ardati, Mol. Pharmacol., 51, 1997, pp. 816-824.
Gaspar et al. Mild Cobalt-Catalyzed Hydrocyanation of Olefins with Tosyl Cyanide. Angew. Chemie. Int. Ed. 2007, vol. 46, pp. 4519-4522.

SUBSTITUTED CYCLOHEXYLDIAMINES

The invention relates to substituted cyclohexyldiamines that have an affinity to the μ-opioid receptor and the ORL 1-receptor, methods for their production, medications containing these compounds and the use of these compounds for the production of medications.

Cyclohexane derivatives that have an affinity to the μ-opioid receptor and the ORL 1-receptor are known in the prior art. In this context, reference can be made, for example, to the following documents in their full scope WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

However, the known compounds are not satisfactory in every respect and there is a need for further compounds with comparable or better properties.

Thus, in appropriate binding assays the known compounds occasionally exhibit a certain affinity to the hERG ion channel, the L-type calcium ion channel (phenylalkylamine, benzothiazepine, dihydropyridine binding sites) or to the sodium channel in the BTX assay (batrachotoxin), which can be respectively interpreted as an indication of cardiovascular side-effects. Moreover, many of the known compounds exhibit only a slight solubility in aqueous media, which can adversely affect the bioavailability, inter alia. In addition, the chemical stability of the known compounds is often merely inadequate. Thus, the compounds occasionally do not exhibit an adequate pH, UV or oxidation stability, which can adversely affect the storage stability and also the oral bioavailability, inter alia. Moreover, the known compounds have an unfavourable PK/PD (pharmacokinetic/pharmacodynamic) profile in some instances, which can be displayed, for example, in too long a duration of effect.

The metabolic stability of the known compounds also appears to be in need of improvement. An improved metabolic stability can point to an increased bioavailability. A weak or absent interaction with transporter molecules that participate in the absorption and excretion of medicinal substances should be considered an indication of an improved bioavailability and possibly low interactions of medications. Moreover, the interactions with the enzymes involved in the breakdown and excretion of medicinal substances should also be as low as possible, since such test results also indicate that low interactions of medications or none at all are possibly to be expected.

The object forming the basis of the invention is to provide compounds that are suitable for pharmaceutical purposes and have advantages over the compounds of the prior art.

This object is achieved by the compounds described hereinbelow.

It has been surprisingly found that substituted cyclohexane derivatives can be produced that have an affinity to the μ-opioid receptor and the ORL 1-receptor.

The invention relates to compounds of the general formula (1)

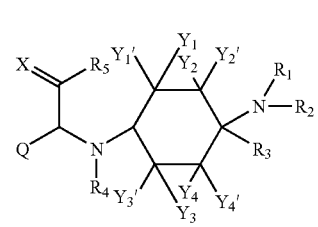

(1)

wherein $Y_1$, $Y_1'$, $Y_2$, $Y_2'$, $Y_3$, $Y_3'$, $Y_4$ and $Y_4'$ are respectively selected independently from the group comprising —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$; preferably respectively selected independently of one another from the group comprising —H, —F, —Cl, —CN and —C$_{1-8}$-aliphatic; or $Y_1$ and $Y_1'$, or $Y_2$ and $Y_2'$, or $Y_3$ and $Y_3'$, or $Y_4$ and $Y_4'$ jointly stand for =O;

Q stands for —R$_0$; preferably for —C$_{1-8}$-aliphatic-aryl or —C$_{1-8}$-aliphatic-heteroaryl; particularly preferred for —CH$_2$-indolyl;

X stands for =O, =CR$_6$R$_7$ or =N—R$_6$;

R$_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

R$_1$ and R$_2$, independently of one another, stand for —H or —R$_0$; or R$_1$ and R$_2$ together stand for —CH$_2$CH$_2$OCH$_2$CH$_2$—, —(CH$_2$)$_{3-6}$— or —CH$_2$CH$_2$NR'CH$_2$CH$_2$— with R'=—H, —R$_0$ or —C(=O)R$_0$;

R$_3$ stands for —R$_0$;

R$_4$ stands for —H, —C(=O)R$_0$ or —R$_0$;

R$_5$ stands for —H, —F, —Cl, —Br, —I, —CN, —NO$_2$, —CHO, —R$_0$, —C(=O)H, —C(=O)R$_0$, —C(=O)OH, —C(=O)OR$_0$, —C(=O)NH$_2$, —C(=O)NHR$_0$, —C(=O)N(R$_0$)$_2$, —N(R$_0$)$_2$, —N$^+$(R$_0$)$_3$, —N$^+$(R$_0$)$_2$O$^-$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ or —NHC(=O)N(R$_0$)$_2$;

R$_6$ and R$_7$ respectively independently of one another stand for —H, —F, —Cl, —Br, —I, —CN, —NO$_2$, —CHO, —R$_0$, —C(=O)H, —C(=O)R$_0$, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ or —NH—C(=O)N(R$_0$)$_2$;

or R$_5$ and R$_6$ jointly form a five- or six-membered ring, the other ring atoms of which respectively independently of one another are C, N, S or O, wherein the ring is aromatic or non-aromatic, unsubstituted or mono- or polysubstituted by substituents selected independently of one another from the group comprising —F, —Cl, —Br, —I, —CN, —NO$_2$, —CHO, =O, —R$_0$, —C(=O)R$_0$, —C(=O)H, —C(=O)

OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH; —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$ and —NH—C(=O)N(R$_0$)$_2$;

wherein

"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue, the number of ring-carbon atoms preferably lies in the specified range (i.e. "C$_{3-8}$-cycloaliphatic" preferably has 3, 4, 5, 6, 7 or 8 ring-carbon atoms);

wherein with respect to "aliphatic" and "cycloaliphatic", "mono- or polysubstituted" is understood to mean the mono- or polysubstitution, e.g. the mono-, di-, tri- or complete substitution, of one or more hydrogen atoms by substituents selected independently of one another from the group comprising aus —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$, —NHC(=O)N(R$_0$)$_2$, —Si(R$_0$)$_3$, —PO(OR$_0$)$_2$;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" is understood to mean the mono- or polysubstitution of one or more hydrogen atoms of the ring system by substituents selected from the group comprising —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)N(R$_0$)$_2$, —Si(R$_0$)$_3$, —PO(OR$_0$)$_2$;

wherein any N-ring atoms present can be respectively oxidised (N-oxide);

in the form of a single stereoisomer or mixture thereof, the free compounds and/or their physiologically compatible salts and/or solvates.

In the combination of different residues, e.g. Y$_1$, Y$_1$', Y$_2$, Y$_2$', Y$_3$, Y$_3$', Y$_4$ and Y$_4$', and also the combination of residues at substituents thereof such as e.g. —OR$_0$, —OC(=O)R$_0$, —OC(=O)NHR$_0$, a substituent, e.g. R$_0$, can assume different meanings within a substance for two or more residues, e.g. —OR$_0$, —OC(=O)R$_0$, —OC(=O)NHR$_0$.

The compounds according to the invention exhibit favourable binding to the ORL 1-receptor and the μ-opioid receptor.

In a preferred embodiment, the compounds according to the invention have an affinity ratio of ORL1/μ of at least 0.1. The ORL1/μ ratio is defined as $1/[K_{i(ORL1)}/K_{i(\mu)}]$. It is particularly preferred if the ORL1/μ ratio amounts to at least 0.2 or at least 0.5, more preferred at least 1.0 or at least 2.0, further preferred at least 3.0 or at least 4.0, most preferred at least 5.0 or at least 7.5 and in particular at least 10 or at least 15. In a preferred embodiment the ORL1/μ ratio lies in the range of 0.1 to 30, more preferred 0.1 to 25.

In another preferred embodiment, the compounds according to the invention have an ORL1/μ affinity ratio of more than 30, more preferred at least 50, further preferred at least 100, most preferred at least 200 and in particular at least 300.

The compounds according to the invention preferably have a K$_i$ value on the μ-opioid receptor of at maximum 500 nM, more preferred at maximum 100 nM, further preferred at maximum 50 nM, most preferred at maximum 10 nM and in particular at maximum 1.0 nM.

Methods for determining the K$_i$ value on the μ-opioid receptor are known to the person skilled in the art. The determination is preferably conducted as described in association with the examples.

It has surprisingly been shown that compounds with affinity to the ORL 1- and μ-opioid receptor, in which the ratio of ORL 1 to μ defined by $1/[K_{i(ORL1)}/K_{i(\mu)}]$ lies in the range of 0.1 to 30, preferably 0.1 to 25, have a pharmacological profile that has significant advantages compared to the other opioid receptor ligand:

1. The compounds according to the invention exhibit an efficacy in acute pain models that is at times comparable with the usual stage-3 opioids. However, they are distinguished at the same time by a significantly better compatibility compared to classic μ-opioids.
2. In contrast to common stage-3 opioids, the compounds according to the invention exhibit a significantly higher efficacy in mono- and polyneuropathic pain models, which is attributable to a synergy of ORL 1- and μ-opioid components.
3. In contrast to common stage-3 opioids, the compounds according to the invention exhibit in neuropathic animals a substantial, preferably a complete, separation of antiallodynic or antihyperalgesic effect and antinociceptive effect.
4. In contrast to common stage-3 opioids, in animal models the compounds according to the invention exhibit a significant increase in efficacy for chronic inflammatory pain (carageenan- or CFA-induced hyperalgesia, visceral inflammatory pain, amongst others) compared to acute pain.
5. In contrast to common stage-3 opioids, side-effects typical of μ-opioids (respiratory depression, opioid-induced hyperalgesia, physical dependence/withdrawal, psychic dependence/addiction, among others) are significantly reduced or preferably not observed with the compounds according to the invention in the therapeutically effective dose range.

In view of the reduced μ-opioid side-effects, on the one hand, and the increased efficacy in chronic, preferably neuropathic pain, on the other hand, the mixed ORL 1/μ agonists are thus distinguished by significantly increased safety margins compared to pure μ-opioids. This results in a significantly increased "therapeutic window" in the treatment of pain conditions, preferably chronic pain, more preferred neuropathic pain.

It is preferred if $Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NH$_2$, —NH—$C_{1-6}$-aliphatic, —NH—$C_{3-8}$-cycloaliphatic, —NH—$C_{1-6}$-aliphatic-OH, —N($C_{1-6}$-aliphatic)$_2$, —N($C_{3-8}$-cycloaliphatic)$_2$, —N($C_{1-6}$-aliphatic-OH)$_2$, —NO$_2$, —NH—$C_{1-6}$-aliphatic-$C_{3-8}$-cycloaliphatic, —NH—$C_{1-6}$-aliphatic-aryl, —NH—$C_{1-6}$-aliphatic-heteroaryl, —NH-aryl, —NH-heteroaryl, —SH, —S—$C_{1-6}$-aliphatic, —S—$C_{3-8}$-cycloaliphatic, —S—$C_{1-6}$-aliphatic-$C_{3-8}$-cycloaliphatic, —S—$C_{1-6}$-aliphatic-aryl, —S—$C_{1-6}$-aliphatic-heteroaryl, —S-aryl, —S-heteroaryl, —OH, —O—$C_{1-6}$-aliphatic, —O—$C_{3-8}$-cycloaliphatic, —O—$C_{1-6}$-aliphatic-OH, —O—$C_{1-6}$-aliphatic-$C_{3-8}$-cycloaliphatic, —O—$C_{1-6}$-aliphatic-aryl, —O—$C_{1-6}$-aliphatic-heteroaryl, —O-aryl, —O-heteroaryl, —O—C(=O)$C_{1-6}$-aliphatic, —O—C(=O)$C_{3-8}$-cycloaliphatic, —O—C(=O)$C_{1-6}$-aliphatic-OH, —O—C(=O)$C_{1-6}$-aliphatic-$C_{3-8}$-cycloaliphatic, —O—C(=O)$C_{1-6}$-aliphatic-aryl, —O—C(=O)$C_{1-6}$-aliphatic-heteroaryl, —O—C(=O)aryl, —O—C(=O)heteroaryl, —$C_{1-6}$-aliphatic, —$C_{3-8}$-cycloaliphatic, —$C_{1-6}$-aliphatic-$C_{3-8}$-cycloaliphatic, —$C_{1-6}$-aliphatic-aryl, —$C_{1-6}$-aliphatic-heteroaryl, -aryl, -heteroaryl, —C(=O)$C_{1-6}$-aliphatic, —C(=O)$C_{3-8}$-cycloaliphatic, —C(=O)$C_{1-6}$-aliphatic-$C_{3-8}$-cycloaliphatic, —C(=O)$C_{1-6}$-aliphatic-aryl, —C(=O)$C_{1-6}$-aliphatic-heteroaryl, —C(=O)aryl, —C(=O)heteroaryl, —CO$_2$H, —CO$_2$—$C_{1-6}$-aliphatic, —CO$_2$—$C_{3-8}$-cycloaliphatic, —CO$_2$—$C_{1-6}$-aliphatic-$C_{3-8}$-cycloaliphatic, —CO$_2$—$C_{1-6}$-aliphatic-aryl, —CO$_2$—$C_{1-6}$-aliphatic-heteroaryl, —CO$_2$-aryl, —CO$_2$-heteroaryl; or $Y_1$ and $Y_1'$, or $Y_2$ and $Y_2'$, or $Y_3$ and $Y_3'$, or $Y_4$ and $Y_4'$ jointly stand for =O. It is preferred if $Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NH$_2$ and —OH.

In a preferred embodiment one of the residues $Y_1$, $Y_1'$, $Y_2$, $Y_2'$, $Y_3$, $Y_3'$, $Y_4$ and $Y_4'$ differs from —H and the remaining residues stand for —H.

It is particularly preferred if $Y_1$, $Y_1'$, $Y_2$, $Y_2'$, $Y_3$, $Y_3'$, $Y_4$ and $Y_4'$ respectively stand for —H.

Q preferably stands for —$C_{1-8}$-aliphatic, -aryl, -heteroaryl, —$C_{1-8}$-aliphatic-aryl or —$C_{1-8}$-aliphatic-heteroaryl; more preferred for —$C_{1-8}$-aliphatic-aryl or —$C_{1-8}$-aliphatic -heteroaryl. In this case, -aliphatic, -aryl and -heteroaryl can be respectively unsubstituted or mono- or polysubstituted, preferably with substituents selected independently of one another from the group comprising —$C_{1-8}$-aliphatic, —OH, —O$C_{1-8}$-aliphatic, —CF$_3$, —F, —Cl, —Br, —NO$_2$, —CN, -heteroaryl, —$C_{1-8}$-aliphatic-aryl and —$C_{1-8}$-aliphatic-heteroaryl.

In a preferred embodiment Q is selected from the group comprising -phenyl, -pyrrolyl, -furyl, -thienyl, -pyridyl, -indolyl, -benzofuryl and -benzothienyl possibly respectively bridged via —$C_{1-8}$-aliphatic, wherein these can respectively be unsubstituted or mono- or polysubstituted, preferably with substituents selected independently of one another from the group comprising —$C_{1-8}$-aliphatic, —OH, —O$C_{1-8}$-aliphatic, —CF$_3$, —F, —Cl, —Br, —NO$_2$, —CN, -heteroaryl, —$C_{1-8}$-aliphatic-aryl and —$C_{1-8}$-aliphatic-heteroaryl (e.g. -ethyl-4-pyridyl).

$R_0$, respectively independently, preferably stands for —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl or —$C_{1-8}$-aliphatic-heteroaryl. In this case —$C_{1-8}$-aliphatic-$C_{3-12}$-cycloaliphatic, —$C_{1-8}$-aliphatic-aryl or —$C_{1-8}$-aliphatic-heteroaryl mean that the residues —$C_{3-12}$-cycloaliphatic, -aryl or -heteroaryl are respectively bonded via a bivalent bridge —$C_{1-8}$-aliphatic-. Preferred examples of —$C_{1-8}$-aliphatic-aryl are —CH$_2$—C$_6$H$_5$, —CH$_2$CH$_2$—C$_6$H$_5$, and —CH=CH—C$_6$H$_5$.

$R_1$ and $R_2$, independently of one another, preferably stand for —H; —$C_{1-6}$-aliphatic; —$C_{3-8}$-cyclo-aliphatic, —$C_{1-6}$-aliphatic-aryl, —$C_{1-6}$-aliphatic-$C_{3-8}$-cycloaliphatic or —$C_{1-6}$-aliphatic-heteroaryl; or the residues $R_1$ and $R_2$ together form a ring and represent —CH$_2$CH$_2$OCH$_2$CH$_2$—, —CH$_2$CH$_2$NR'—CH$_2$CH$_2$— or —(CH$_2$)$_{3-6}$—. It is more preferred if $R_1$ and $R_2$, independently of one another, stand for —H; —$C_{1-5}$-aliphatic; or the residues $R_1$ and $R_2$ together form a ring and represent —CH$_2$CH$_2$OCH$_2$CH$_2$—, —CH$_2$CH$_2$NR'—CH$_2$CH$_2$— or —(CH$_2$)$_{3-6}$—, wherein R' preferably represents —H or —$C_{1-5}$-aliphatic. Particularly preferred are those compounds, in which $R_1$ and $R_2$, independently of one another, stand for —CH$_3$ or —H, wherein $R_1$ and $R_2$ do not simultaneously represent —H; or $R_1$ and $R_2$ form a ring and represent —(CH$_2$)$_{3-4}$—. Compounds, in which $R_1$ and $R_2$ stand for —CH$_3$ or in which $R_1$ stands for —H and $R_2$ stands for —CH$_3$, are most particularly preferred.

It is particularly preferred if $R_1$ and $R_2$ together with the nitrogen atom, to which they are bonded, form one of the following functional groups:

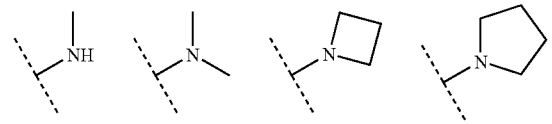

$R_3$ preferably stands for —$C_{1-8}$-aliphatic, —$C_{3-8}$-cycloaliphatic, -aryl, -heteroaryl; or for -aryl, -heteroaryl or —$C_{3-8}$-cycloaliphatic respectively bonded via a —$C_{1-3}$-aliphatic group.

It is particularly preferred if $R_3$ stands for -ethyl, -propyl, -butyl, -pentyl, -hexyl, -heptyl, -cyclopentyl, -cyclohexyl, -phenyl, -benzyl, -naphthyl, -anthracenyl, -thiophenyl, -benzothiophenyl, -furyl, -benzofuranyl, -benzodioxolanyl, -indolyl, -indanyl, -benzodioxanyl, -pyrrolyl, -pyridyl, -pyrimidyl or -pyrazinyl, respectively unsubstituted or mono- or polysubstituted; —$C_{5-6}$-cycloaliphatic, -phenyl, -naphthyl, -anthracenyl, -thiophenyl, -benzothiophenyl, -pyridyl, -furyl, -benzofuranyl, -benzodioxolanyl, -indolyl, -indanyl, -benzodioxanyl, -pyrrolyl, -pyrimidyl, -triazolyl or -pyrazinyl, respectively unsubstituted or mono- or polysubstituted; bonded via a saturated, unbranched —$C_{1-3}$-aliphatic group.

It is more preferred if $R_3$ stands for -propyl, -butyl, -pentyl, -hexyl, -phenyl, -furyl, -thiophenyl, -naphthyl, -benzyl, -benzofuranyl, -indolyl, -indanyl, -benzodioxanyl, -benzodioxolanyl, -pyridyl, -pyrimidyl, -pyrazinyl, -triazolyl or -benzothiophenyl, respectively unsubstituted or mono- or polysubstituted; -phenyl, -furyl or -thiophenyl, respectively unsubstituted or mono- or polysubstituted, bonded via a saturated, unbranched —$C_{1-3}$-aliphatic group.

It is further preferred if $R_3$ stands for -propyl, -butyl, -pentyl, -hexyl, -phenyl, -phenethyl, -thiophenyl, -pyridyl, -triazolyl, -benzothiophenyl or -benzyl, respectively substituted or unsubstituted, particularly preferred for -propyl, -3-methoxypropyl, -butyl, -pentyl, -hexyl, -phenyl, -3-methylphenyl, -3-fluorophenyl, -benzo[1,3]-dioxolyl, -thienyl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

It is especially preferred if $R_3$ stands for -butyl, -ethyl, -3-methoxypropyl, -benzothiophenyl, -phenyl, -3-methylphenyl, -3-fluorophenyl, -benzo[1,3]-dioxolyl, -benzyl, -1-methyl-1,2,4-triazolyl, -thienyl or -phenethyl.

It is most preferred if $R_3$ stands for -phenyl, -benzyl or -phenethyl, respectively unsubstituted or mono- or polysubstituted on the ring; $—C_{1-5}$-aliphatic, $—C_{4-6}$-cycloaliphatic, -pyridyl, -thienyl, -thiazolyl, -imidazolyl, -1,2,4 triazolyl or -benzimidazolyl, unsubstituted or mono- or polysubstituted.

It is particularly preferred if $R_3$ stands for -phenyl, -benzyl, -phenethyl, -thienyl, -pyridyl, -thiazolyl, -imidazolyl, -1,2,4 triazolyl, -benzimidazolyl or -benzyl, unsubstituted or mono- or polysubstituted with —F, —Cl, —Br, —CN, —$CH_3$, —$C_2H_5$, —$NH_2$, —$NO_2$, —SH, —$CF_3$, —OH, —$OCH_3$, —$OC_2H_5$ or —$N(CH_3)_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, respectively unsubstituted or mono- or polysubstituent with —OH, —$OCH_3$ or —$OC_2H_5$, wherein -thienyl, -pyridyl, -thiazolyl, -imidazolyl, -1,2,4-triazolyl and -benzimidazolyl are preferably unsubstituted.

It is particularly preferred if $R_3$ stands for -phenyl, unsubstituted or mono-substituted with —F, —Cl, —CN, —$CH_3$; -thienyl; -ethyl, -n-propyl or -n-butyl, unsubstituted or mono- or polysubstituted with —$OCH_3$, —OH or —$OC_2H_5$, in particular with —$OCH_3$.

$R_4$ preferably stands for —H, —$C_{1-5}$-aliphatic, —$C_{3-8}$-cycloaliphatic, -aryl, -heteroaryl, —$C_{1-6}$-aliphatic-aryl, —$C_{1-6}$-aliphatic-$C_{3-8}$-cycloaliphatic, —$C_{1-6}$-aliphatic-heteroaryl, —C(=O)aryl, —C(=O)heteroaryl, —C(=O)$C_{1-6}$-aliphatic, —C(=O)$C_{1-6}$-aliphatic-aryl, —C(=O)$C_{1-6}$-aliphatic-heteroaryl, —C(=O)$C_{3-8}$-cycloaliphatic-aryl, —C(=O)$C_{3-8}$-cycloaliphatic-heteroaryl, more preferred for —H or —$C_{1-5}$-aliphatic, in particular for —H or —$CH_3$.

X stands for =O, =$CR_6R_7$ or =N—$R_6$. If X stands for =O, then the compound of the general formula (1) according to the invention has the general formula (1-a). If X stands for =$NR_6$, then the compound of the general formula (1) according to the invention has the general formula (1-b). If X stands for =$CR_6R_7$, then the compound of the general formula (1) according to the invention has the general formula (1-c):

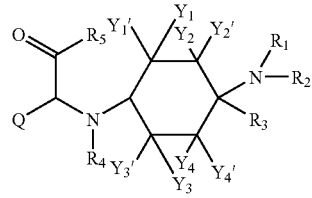

(1-a)

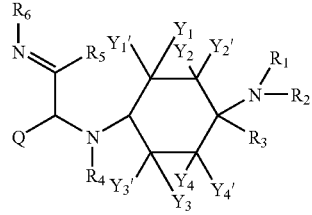

(1-b)

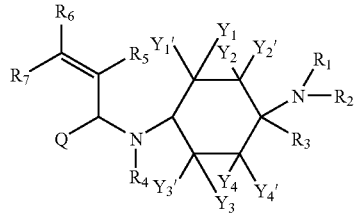

(1-c)

Preferred embodiments of the compounds of the general formulae (1-b) and (1-c) are shown below:

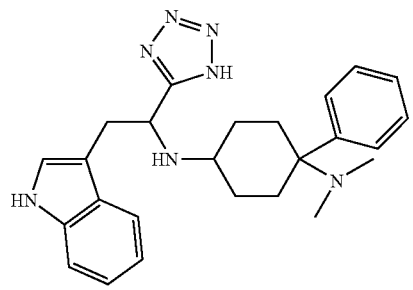

E-1

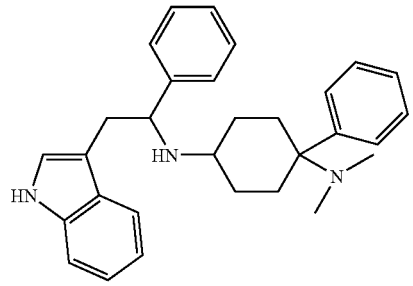

E-2

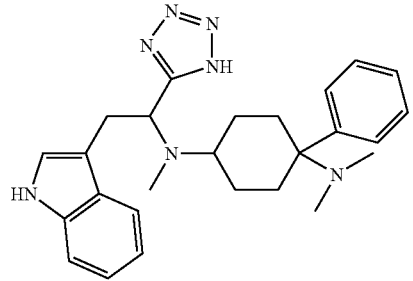

E-3

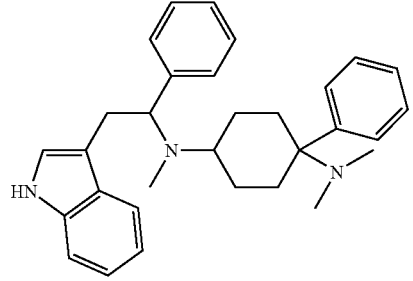

E-4

$R_5$ preferably stands for —H, —F, —Cl, —Br, —I, —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —C(=O)H, —C(=O)—$C_{1-8}$-aliphatic, —C(=O)—$C_{3-12}$-cycloaliphatic, —C(=O)-aryl, —C(=O)-heteroaryl, —C(=O)—C$_{1-8}$-aliphatic-C$_{3-12}$-cycloaliphatic, —C(=O)—C$_{1-8}$-aliphatic-aryl, —C(=O)—C$_{1-8}$-aliphatic-heteroaryl, —C(=O)O—C$_{1-8}$-aliphatic, —C(=O)O—C$_{3-12}$-cycloaliphatic, —C(=O)O-aryl, —C(=O)O-heteroaryl, —C(=O)O—C$_{1-8}$-aliphatic-C$_{3-12}$-cycloaliphatic, —C(=O)O—C$_{1-8}$-aliphatic-aryl, —C(=O)O—C$_{1-8}$-aliphatic-heteroaryl, —CN, —C(=O)NH$_2$, —C(=O)—NH—C$_{1-8}$-aliphatic, —C(=O)NH—C$_{3-12}$-cycloaliphatic, —C(=O)NH-aryl, —C(=O)NH-heteroaryl, —C(=O)—NH—C$_{1-8}$-aliphatic-C$_{3-12}$-cycloaliphatic, —C(=O)NH—C$_{1-8}$-aliphatic-aryl, —C(=O)NH—C$_{1-8}$-aliphatic-heteroaryl, —C(=O)N(C$_{1-8}$-aliphatic)$_2$, —C(=O)N(C$_{3-12}$-cycloaliphatic)$_2$, —C(=O)N(aryl)$_2$, —C(=O)N(heteroaryl)$_2$, —C(=O)N(C$_{1-8}$-aliphatic-C$_{3-12}$-cycloaliphatic)$_2$, —C(=O)N(C$_{1-8}$-aliphatic-aryl)$_2$, —C(=O)—N(C$_{1-8}$-aliphatic-heteroaryl)$_2$, —NH$_2$, —NO$_2$, —NH—C$_{1-8}$-aliphatic, —NH—C$_{3-12}$-cycloaliphatic, —NH-aryl, —NH-heteroaryl, —NH—C$_{1-8}$-aliphatic-C$_{3-12}$-cycloaliphatic, —NH—C$_{1-8}$-aliphatic-aryl, —NH—C$_{1-8}$-aliphatic-heteroaryl, —N(C$_{1-8}$-aliphatic)$_2$, —N(C$_{3-12}$-cycloaliphatic)$_2$, —N(aryl)$_2$, —N(heteroaryl)$_2$, —N(C$_{1-8}$-aliphatic-C$_{3-12}$-cycloaliphatic)$_2$, —N(C$_{1-8}$-aliphatic-aryl)$_2$, —N(C$_{1-8}$-aliphatic-heteroaryl)$_2$, —NHC(=O)—C$_{1-8}$-aliphatic, —NHC(=O)—C$_{3-12}$-cycloaliphatic, —NHC(=O)-aryl, —NHC(=O)-heteroaryl, —NHC(=O)—C$_{1-8}$-aliphatic-C$_{3-12}$-cycloaliphatic, —NHC(=O)—C$_{1-8}$-aliphatic-aryl, —NHC(=O)—C$_{1-8}$-aliphatic-heteroaryl, —NHC(=O)O—C$_{1-8}$-aliphatic, —NHC(=O)O—C$_{3-12}$-cycloaliphatic, —NHC(=O)O-aryl, —NHC(=O)O-heteroaryl, —NHC(=O)O—C$_{1-8}$-aliphatic-C$_{3-12}$-cycloaliphatic, —NHC(=O)O—C$_{1-8}$-aliphatic-aryl, —NHC(=O)O—C$_{1-8}$-aliphatic-heteroaryl, —NHC(=O)NH—C$_{1-8}$-aliphatic, —NHC(=O)NH—C$_{3-12}$-cycloaliphatic, —NHC(=O)NH-aryl, —NHC(=O)—NH-heteroaryl, —NHC(=O)NH—C$_{1-8}$-aliphatic-C$_{3-12}$-cycloaliphatic, —NHC(=O)NH—C$_{1-8}$-aliphatic-aryl, —NHC(=O)NH—C$_{1-8}$-aliphatic-heteroaryl, —NHC(=O)N(C$_{1-8}$-aliphatic)$_2$, —NHC(=O)N(C$_{3-2}$-cycloaliphatic)$_2$, —NHC(=O)N(aryl)$_2$, —NHC(=O)—N(heteroaryl)$_2$, —NHC(=O)N(C$_{1-8}$-aliphatic-C$_{3-12}$-cycloaliphatic)$_2$, —NHC(=O)N(C$_{1-8}$-aliphatic-aryl)$_2$, —NHC(=O)N(C$_{1-8}$-aliphatic-hetero-aryl)$_2$, —SH, —SC$_{1-8}$-aliphatic, —SC$_{3-12}$-cycloaliphatic, —S-aryl, —S-heteroaryl, —SC$_{1-8}$-aliphatic-C$_{3-12}$-cycloaliphatic, —SC$_{1-8}$-aliphatic-aryl, —SC$_{1-8}$-aliphatic-heteroaryl, —S(=O)$_{1-2}$C$_{1-8}$-aliphatic, —S(=O)$_{1-2}$C$_{3-12}$-cycloaliphatic, —S(=O)$_{1-2}$aryl, —S(=O)$_{1-2}$heteroaryl, —S(=O)$_{1-2}$C$_{1-8}$-aliphatic-C$_{3-12}$-cycloaliphatic, —S(=O)$_{1-2}$C$_{1-8}$-aliphatic-aryl, —S(=O)$_{1-2}$C$_{1-8}$-aliphatic-heteroaryl, —S(=O)$_{1-2}$OH, —S(=O)$_{1-2}$OC$_{1-8}$-aliphatic, —S(=O)$_{1-2}$OC$_{3-12}$-cycloaliphatic, —S(=O)$_{1-2}$Oaryl, —S(=O)$_{1-2}$Oheteroaryl, —S(=O)$_{1-2}$OC$_{1-8}$-aliphatic-C$_{3-12}$-cycloaliphatic, —S(=O)$_{1-2}$OC$_{1-8}$-aliphatic-aryl, —S(=O)$_{1-2}$OC$_{1-8}$-aliphatic-heteroaryl, —S(=O)$_{1-2}$NH$_2$, —S(=O)$_{1-2}$NHC$_{1-8}$-aliphatic, —S(=O)$_{1-2}$NHC$_{3-12}$-cycloaliphatic, —S(=O)$_{1-2}$NH-aryl, —S(=O)$_{1-2}$NH-heteroaryl, —S(=O)$_{1-2}$NHC$_{1-8}$-aliphatic-C$_{3-12}$-cycloaliphatic, —S(=O)$_{1-2}$NHC$_{1-8}$-aliphatic-aryl, —S(=O)$_{1-2}$NHC$_{1-8}$-aliphatic-heteroaryl, —S(=O)$_{1-2}$N(C$_{1-8}$-aliphatic)$_2$, —S(=O)$_{1-2}$N(C$_{3-12}$-cycloaliphatic)$_2$, —S(=O)$_{1-2}$N(aryl)$_2$, —S(=O)$_{1-2}$N(heteroaryl)$_2$, —S(=O)$_{1-2}$N(C$_{1-8}$-aliphatic-C$_{3-12}$-cycloaliphatic)$_2$, —S(=O)$_{1-2}$N(C$_{1-8}$-aliphatic-aryl)$_2$ or —S(=O)$_{1-2}$N(C$_{1-8}$-aliphatic-heteroaryl)$_2$.

R$_6$ and R$_7$, independently of one another, preferably stand for —H, —F, —Cl, —Br, —I, —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C(=O)H, —C(=O)—C$_{1-8}$-aliphatic, —C(=O)—C$_{3-12}$-cycloaliphatic, —C(=O)-aryl, —C(=O)-heteroaryl, —C(=O)—C$_{1-8}$-aliphatic-C$_{3-12}$-cycloaliphatic, —C(=O)—C$_{1-8}$-aliphatic-aryl, —C(=O)—C$_{1-8}$-aliphatic-heteroaryl, —C(=O)O—C$_{1-8}$-aliphatic, —C(=O)O—C$_{3-12}$-cycloaliphatic, —C(=O)O-aryl, —C(=O)O-heteroaryl, —C(=O)O—C$_{1-8}$-aliphatic-C$_{3-12}$-cycloaliphatic, —C(=O)O—C$_{1-8}$-aliphatic-aryl, —C(=O)O—C$_{1-8}$-aliphatic-heteroaryl, —CN, —C(=O)NH$_2$, —C(=O)—NH—C$_{1-8}$-aliphatic, —C(=O)NH—C$_{3-12}$-cycloaliphatic, —C(=O)NH-aryl, —C(=O)NH-heteroaryl, —C(=O)—NH—C$_{1-8}$-aliphatic-C$_{3-12}$-cycloaliphatic, —C(=O)NH—C$_{1-8}$-aliphatic-aryl, —C(=O)NH—C$_{1-8}$-aliphatic-heteroaryl, —C(=O)N(C$_{1-8}$-aliphatic)$_2$, —C(=O)N(C$_{3-12}$-cycloaliphatic)$_2$, —C(=O)N(aryl)$_2$, —C(=O)N(heteroaryl)$_2$, —C(=O)N(C$_{1-8}$-aliphatic-C$_{3-2}$-cycloaliphatic)$_2$, —C(=O)N(C$_{1-8}$-aliphatic-aryl)$_2$, —C(=O)—N(C$_{1-8}$-aliphatic-heteroaryl)$_2$, —OH, —OC$_{1-8}$-aliphatic, —OC$_{3-12}$-cycloaliphatic, -Oaryl, -Oheteroaryl, —OC$_{1-8}$-aliphatic-C$_{3-12}$-cycloaliphatic, —OC$_{1-8}$-aliphatic-aryl, —OC$_{1-8}$-aliphatic-heteroaryl, —OC(=O)H, —OC(=O)—C$_{1-8}$-aliphatic, —OC(=O)—C$_{3-12}$-cycloaliphatic, —OC(=O)-aryl, —OC(=O)-heteroaryl, —OC(=O)—C$_{1-8}$-aliphatic-C$_{3-12}$-cycloaliphatic, —OC(=O)—C$_{1-8}$-aliphatic-aryl, —OC(=O)—C$_{1-8}$-aliphatic-heteroaryl, —OC(=O)O—C$_{1-8}$-aliphatic, —OC(=O)O—C$_{3-12}$-cycloaliphatic, —OC(=O)O-aryl, —OC(=O)—O-heteroaryl, —OC(=O)O—C$_{1-8}$-aliphatic-C$_{3-12}$-cycloaliphatic, —OC(=O)O—C$_{1-8}$-aliphatic-aryl, —OC(=O)—O—C$_{1-8}$-aliphatic-heteroaryl, —OC(=O)NH—C$_{1-8}$-aliphatic, —OC(=O)NH—C$_{3-12}$-cycloaliphatic, —OC(=O)NH-aryl, —OC(=O)NH-heteroaryl, —OC(=O)NH—C$_{1-8}$-aliphatic-C$_{3-12}$-cycloaliphatic, —OC(=O)NH—C$_{1-8}$-aliphatic-aryl, —OC(=O)NH—C$_{1-8}$-aliphatic-heteroaryl, —OC(=O)N(C$_{1-8}$-aliphatic)$_2$, —OC(=O)N(C$_{3-12}$-cycloaliphatic)$_2$, —OC(=O)N(aryl)$_2$, —OC(=O)—N(heteroaryl)$_2$, —OC(=O)N(C$_{1-8}$-aliphatic-C$_{3-12}$-cycloaliphatic)$_2$, —OC(=O)N(C$_{1-8}$-aliphatic-aryl)$_2$, —OC(=O)N(C$_{1-8}$-aliphatic-heteroaryl)$_2$, —NH$_2$, —NO$_2$, —NH—C$_{1-8}$-aliphatic, —NH—C$_{3-12}$-cycloaliphatic, —NH-aryl, —NH-heteroaryl, —NH—C$_{1-8}$-aliphatic-C$_{3-12}$-cycloaliphatic, —NH—C$_{1-8}$-aliphatic-aryl, —NH—C$_{1-8}$-aliphatic-heteroaryl, —N(C$_{1-8}$-aliphatic)$_2$, —N(C$_{3-12}$-cycloaliphatic)$_2$, —N(aryl)$_2$, —N(heteroaryl)$_2$, —N(C$_{1-8}$-aliphatic-C$_{3-12}$-cycloaliphatic)$_2$, —N(C$_{1-8}$-aliphatic-aryl)$_2$, —N(C$_{1-8}$-aliphatic-heteroaryl)$_2$, —NHC(=O)—C$_{1-8}$-aliphatic, —NHC(=O)—C$_{3-12}$-cycloaliphatic, —NHC(=O)-aryl, —NHC(=O)-heteroaryl, —NHC(=O)—C$_{1-8}$-aliphatic-C$_{3-12}$-cycloaliphatic, —NHC(=O)—C$_{1-8}$-aliphatic-aryl, —NHC(=O)—C$_{1-8}$-aliphatic-heteroaryl, —NHC(=O)O—C$_{1-8}$-aliphatic, —NHC(=O)O—C$_{3-12}$-cycloaliphatic, —NHC(=O)O-aryl, —NHC(=O)O-heteroaryl, —NHC(=O)O—C$_{1-8}$-aliphatic-C$_{3-12}$-cycloaliphatic, —NHC(=O)O—C$_{1-8}$-aliphatic-aryl, —NHC(=O)O—C$_{1-8}$-aliphatic-heteroaryl, —NHC(=O)NH—C$_{1-8}$-aliphatic, —NHC(=O)NH—C$_{3-12}$-cycloaliphatic, —NHC(=O)NH-aryl, —NHC(=O)—NH-heteroaryl, —NHC(=O)NH—C$_{1-8}$-aliphatic-C$_{3-12}$-cycloaliphatic, —NHC(=O)NH—C$_{1-8}$-aliphatic-aryl, —NHC(=O)NH—C$_{1-8}$-aliphatic-heteroaryl, —NHC(=O)N(C$_{1-8}$-aliphatic)$_2$, —NHC(=O)N(C$_{3-12}$-cycloaliphatic)$_2$, —NHC(=O)N(aryl)$_2$, —NHC(=O)—N(heteroaryl)$_2$, —NHC(=O)N(C$_{1-8}$-aliphatic-C$_{3-12}$-cycloaliphatic)$_2$, —NHC(=O)N(C$_{1-8}$-aliphatic-aryl)$_2$, —NHC(=O)N(C$_{1-8}$-aliphatic-heteroaryl)$_2$, —SH, —SC$_{1-8}$-aliphatic, —SC$_{3-12}$-cycloaliphatic, —S-aryl, —S-heteroaryl, —SC$_{1-8}$-aliphatic-C$_{3-12}$-cycloaliphatic, —SC$_{1-8}$-aliphatic-aryl, —SC$_{1-8}$-aliphatic-heteroaryl, —S(=O)$_{1-2}$C$_{1-18}$-aliphatic, —S(=O)$_{1-2}$C$_{3-12}$-cycloaliphatic, —S(=O)$_{1-2}$aryl, —S(=O)$_{1-2}$ heteroaryl, —S(=O)$_{1-2}$C$_{1-8}$-aliphatic-C$_{3-12}$-cycloaliphatic, —S(=O)$_{1-2}$C$_{1-8}$-aliphatic-aryl, —S(=O)$_{1-2}$C$_{1-8}$-aliphatic-heteroaryl, —S(=O)$_{1-2}$OH, —S(=O)$_{1-2}$OC$_{1-8}$-aliphatic, —S(=O)$_{1-2}$OC$_{3-12}$-cycloaliphatic, —S(=O)$_{1-2}$Oaryl, —S(=O)$_{1-2}$Oheteroaryl, —S(=O)$_{1-2}$OC$_{1-8}$-aliphatic-C$_{3-12}$-cycloaliphatic, —S(=O)$_{1-2}$OC$_{1-8}$-aliphatic-aryl, —S(=O)$_{1-2}$OC$_{1-8}$-aliphatic-heteroaryl, —S(=O)$_{1-2}$NH$_2$, —S(=O)$_{1-2}$NHC$_{1-8}$-aliphatic, —S(=O)$_{1-2}$NHC$_{3-12}$-cycloaliphatic, —S(=O)$_{1-2}$NH-aryl, —S(=O)$_{1-2}$NH-heteroaryl, —S(=O)$_{1-2}$NHC$_{1-8}$-aliphatic-C$_{3-12}$-cycloaliphatic, —S(=O)$_{1-2}$NHC$_{1-8}$-aliphatic-aryl, —S(=O)$_{1-2}$NHC$_{1-8}$-aliphatic-heteroaryl, —S(=O)$_{1-2}$N(C$_{1-8}$-aliphatic)$_2$, —S(=O)$_{1-2}$N(C$_{3-12}$-cycloaliphatic)$_2$, —S(=O)$_{1-2}$N(aryl)$_2$, —S(=O)$_{1-2}$N(heteroaryl)$_2$, —S(=O)$_{1-2}$N(C$_{1-8}$-aliphatic-C$_{3-12}$-cycloaliphatic)$_2$, —S(=O)$_{1-2}$N(C$_{1-8}$-aliphatic-aryl)$_2$ or —S(=O)$_{1-2}$N(C$_{1-8}$-aliphatic-heteroaryl)$_2$;

or $R_5$ and $R_6$ jointly form a five- or six-membered ring, the other ring atoms of which (i.e. the 3 or 4 ring atoms besides X and the C-atom, to which X is bonded) respectively independently of one another are C, N, S or O, wherein the ring is aromatic or non-aromatic, unsubstituted or mono- or polysubstituted. In this embodiment, $R_5$ thus represents a possibly substituted ring atom selected from the group comprising C, N, S or O. If $R_5$ forms a ring atom —O— or —S—, then this is not further substituted. If $R_5$ forms a ring atom —C—, then this is di-substituted, wherein the substituents can be —H, inter alia, (—CH$_2$—). If $R_5$ forms a ring atom =C—, then this is mono-substituted, wherein the substituent can be —H, inter alia, (=CH—). If $R_5$ forms a ring atom —N—, then this is mono-substituted, wherein the substituent can be —H, inter alia, (—NH—). If $R_5$ forms a ring atom =N—, then this is not substituted further. If the ring jointly formed by $R_5$ and $R_6$ is substituted with one or more substituents, which differ from —H, then the substituents are preferably selected independently of one another from the group comprising —F, —Cl, —Br, —I, —CN, —NO$_2$, —CHO, =O, —R$_0$, —OH, —OR$_0$, —NH$_2$, —NHR$_0$ and —N(R$_0$)$_2$; particularly preferred =O and —CH$_3$.

If X stands for =O, then $R_5$ preferably stands for —NH$_2$, —NH—C$_{1-8}$-aliphatic, —NH—C$_{3-12}$-cyclo-aliphatic, —NH-aryl, —NH-heteroaryl, —NH—C$_{1-8}$-aliphatic-C$_{3-12}$-aycloaliphatic, —NH—C$_{1-8}$-aliphatic-aryl, —NH—C—s-aliphatic-heteroaryl, —N(C$_{1-8}$-aliphatic)$_2$, —N(C$_{3-12}$-cycloaliphatic)$_2$, —N(aryl)$_2$, —N(heteroaryl)$_2$, —N(C$_{1-8}$-aliphatic-C$_{3-12}$-cycloaliphatic)$_2$, —N(C$_{1-8}$-aliphatic-aryl)$_2$, or —N(C$_{1-8}$-aliphatic-heteroaryl)$_2$; particularly preferred for —NH$_2$, —NHC$_{1-8}$-aliphatic or —N(C$_{1-8}$-aliphatic)$_2$.

If X stands for =CR$_6$R$_7$ or =NR$_6$, then $R_5$ preferably together with $R_6$ forms a five- or six-membered ring, the other ring atoms of which (i.e. the 3 or 4 ring atoms besides X and the C-atom, to which X is bonded) respectively independently of one another are C, N, S or O, wherein the ring is aromatic or non-aromatic, unsubstituted or mono- or polysubstituted. The functional group —CR$_5$(=X) preferably stands for one of the following residues, which can be unsubstituted or mono- or polysubstituted:

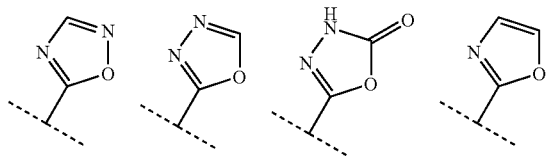

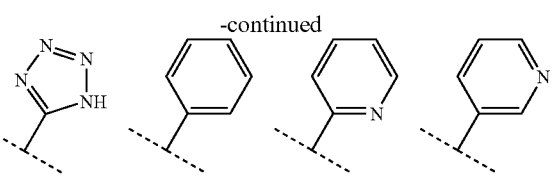

$R_7$ preferably stands for —H, —F, —Cl, —Br, —CH$_3$, —OH, —OCH$_3$, —CN or —NO$_2$.

For the purposes of the description hydrocarbon residues are divided into aliphatic hydrocarbon residues and aromatic hydrocarbon residues.

Aliphatic hydrocarbon residues are themselves divided into non-cyclic aliphatic hydrocarbon residues (="aliphatic") and cyclic aliphatic hydrocarbon residues, i.e. alicyclic hydrocarbon residues (="cycloaliphatic"). Cycloaliphatic compounds can be monocyclic or multicyclic. Alicyclic hydrocarbon residues ("cycloaliphatic") comprise both pure aliphatic carbocycles and aliphatic heterocycles, i.e.—unless expressly specified—"cycloaliphatic" comprises pure aliphatic carbocycles (e.g. cyclohexyl), pure aliphatic heterocycles (e.g. piperidyl or piperazyl) and also non-aromatic, multicyclic, possibly mixed, systems (e.g. decalinyl, decahydroquinolinyl).

Aromatic hydrocarbons are themselves divided into carbocyclic aromatic hydrocarbons (="aryl") and heterocyclic aromatic hydrocarbons (="heteroaryl").

The classification of multicyclic, at least partially aromatic systems preferably depends on whether at least one aromatic ring of the multicyclic system has at least one heteroatom (usually N, O or S) in the ring. If at least one such heteroatom is present in this ring, this is preferably a "heteroaryl" (even if a further carbocyclic aromatic or non-aromatic ring with or without heteroatom is possibly present as additionally present cycle of the multicyclic system); if such a heteroatom is not present in any of the possibly several aromatic rings of the multicyclic system, then this is preferably "aryl" (even if a ring heteroatom is present in a possibly additionally present non-aromatic cycle of the multicyclic system).

Therefore, the following priority in the classification applies within the cyclic substituents: heteroaryl>aryl>cycloaliphatic.

For the purposes of the description monovalent and multivalent, i.e. bivalent, hydrocarbon residues are not distinguished between conceptually, i.e. depending on the context, "C$_{1-3}$-aliphatic" covers e.g. —C$_{1-3}$-alkyl, —C$_{1-3}$-alkenyl and —C$_{1-3}$-alkinyl, as well as e.g. —C$_{1-3}$-alkylene-, —C$_{1-3}$-alkenylene- and C$_{1-3}$-alkinylene.

Aliphatic is preferably respectively a branched or unbranched, saturated or a mono- or polyunsaturated, unsubstituted or mono- or polysubstituted, aliphatic hydrocarbon residue. Where aliphatic is mono- or polysubstituted, the substituents are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$. Thus, "aliphatic" covers acyclic saturated or unsaturated hydrocarbon residues that can be branched or straight-chain, i.e. alkanyls, alkenyls and alkinyls. In this case, alkenyls have at least one C=C double bond and alkinyls have at least one C—C triple bond. Preferred unsubstituted monovalent aliphatics comprise —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2$—$CH_2CH_3$ and —$CH_2CH_2CH_2CH_2CH_3$; but also —CH=$CH_2$, —C≡CH, —$CH_2$CH=$CH_2$, —CH=CHCH$_3$, —$CH_2$C≡CH, —C≡CCH$_3$ and —CH=CHCH=$CH_2$. Preferred unsubstituted bivalent aliphatics comprise —$CH_2$—, —$CH_2CH_2$—, —$CH_2$CH(CH$_3$)—, —CH(CH$_3$)—CH$_2$—, —$CH_2CH_2CH_2$—, —CH(CH$_3$)CH$_2CH_2$—, —CH$_2$CH(CH$_3$)—CH$_2$—, —CH$_2CH_2$CH(CH$_3$)—, —CH=(CH$_2$CH$_3$)CH$_2$— and —$CH_2CH_2$—$CH_2CH_2$—; but also —CH=CH—, —C≡C—, —$CH_2$CH=CH—, —CH=CHCH$_2$—, —$CH_2CH_2$— and —C≡CCH$_2$—. Preferred substituted monovalent aliphatics comprise —$CH_2F$, —$CHF_2$, —$CF_3$, —$CH_2CF_3$, —$CF_2CF_3$, —$CH_2OH$, —$CH_2CH_2OH$, —$CH_2$CHOHCH$_3$, —$CH_2OCH_3$ and —$CH_2CH_2OCH_3$. Preferred substituted bivalent aliphatics comprise —$CF_2$—, —$CF_2CF_2$—, —$CH_2$CHOH—, —CHOHCH$_2$— and —$CH_2$CHOHCH$_2$—. -Methyl-, -ethyl-, -n-propyl- and -n-butyl are particularly preferred.

Cycloaliphatic is preferably respectively a saturated or a mono- or polyunsaturated, unsubstituted or mono- or polysubstituted, aliphatic (i.e. not aromatic), mono- or multicyclic hydrocarbon residue. The number of ring-carbon atoms preferably lies in the specified range (i.e. a "$C_{3-8}$-cycloaliphatic" preferably has 3, 4, 5, 6, 7 or 8 ring-carbon atoms). For the purposes of the description "$C_{3-8}$-cycloaliphatic" is preferably a cyclic hydrocarbon with 3, 4, 5, 6, 7 or 8 ring-carbon atoms, saturated or unsaturated, but not aromatic, wherein possibly one or two carbon atoms are replaced independently of one another by a heteroatom S, N or O. Where cycloalkyl is mono- or polysubstituted, the substituents are selected independently of one another from the group comprising —F, —Cl, —Br, —I, —CN, —$NO_2$, —CHO, =O, —$R_0$, —C(=O)$R_0$, —C(=O)OH, —C(=O)O$R_0$, —C(=O)$NH_2$, —C(=O)NH$R_0$, —C(=O)N($R_0$)$_2$, —OH, —O$R_0$, —OC(=O)H, —OC(=O)$R_0$, —OC(=O)O$R_0$, —OC(=O)NH$R_0$, —OC(=O)—N($R_0$)$_2$, —SH, —S$R_0$, —$SO_3$H, —S(=O)$_{1-2}$—$R_0$, —S(=O)$_{1-2}$NH$_2$, —$NH_2$, —NH$R_0$, —N($R_0$)$_2$, —$N^+$($R_0$)$_3$, —$N^+$($R_0$)$_2O^-$, —NHC(=O)$R_0$, —NHC(=O)O$R_0$, —NHC(=O)$NH_2$, —NHC(=O)NH$R_0$, —NHC(=O)N($R_0$)$_2$, —Si($R_0$)$_3$, —PO(O$R_0$)$_2$. Advantageously, $C_{3-8}$-cycloaliphatic is selected from the group comprising cyclopropyl, cyclobutyl, cyclopentyl, cyclohexyl, cycloheptyl, cyclooctyl, cyclo-pentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

In association with "aliphatic" or "cycloaliphatic", "mono- or polysubstituted" is preferably understood to mean the mono- or polysubstitution, e.g. the mono-, di-, tri- or 4-substitution, of one or more hydrogen atoms by —F, —Cl, —Br, —I, —OH, —OC$_{1-6}$-alkyl, —OC(=O)C$_{1-6}$-alkyl, —SH, —$NH_2$, —NHC$_{1-6}$-alkyl, —N(C$_{1-6}$-alkyl)$_2$, —C(=O)OC$_{1-6}$-alkyl or —C(=O)OH. Compounds, wherein "aliphatic substituted" or "cycloaliphatic substituted" means aliphatic or cycloaliphatic substituted with —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —N($CH_3$)$_2$, are preferred. Particularly preferred substituents are —F, —Cl, —OH, —SH, —$NH_2$ and —C(=O)OH.

Polysubstituted residues are understood to be those residues that are polysubstituted, e.g. twice or three times either at different or at the same atoms, e.g. three times at the same C-atom, as in the case of —$CF_3$ or —$CH_2CF_3$, or at different sites, as in the case of —CH(OH)—CH=CH—CHCl$_2$. The polysubstitution can occur with the same or with different substituents. A substituent may also be substituted itself. Thus, -Oaliphatic also covers —$OCH_2CH_2O$—$CH_2CH_2OH$, amongst others. It is preferred if aliphatic or cycloaliphatic is substituted with —F, —Cl, —Br, —I, —CN, —$CH_3$, —$C_2H_5$, —$NH_2$, —$NO_2$, —SH, —$CF_3$, —OH, —$OCH_3$, —$OC_2H_5$ or —N($CH_3$)$_2$.

It is most particularly preferred if aliphatic or cycloaliphatic is substituted with —OH, —$OCH_3$ or —$OC_2H_5$.

It is preferred if aryl respectively independently stands for a carbocyclic ring system with at least one aromatic ring, but without heteroatoms in this ring, wherein the aryl residues can possibly be condensed with further saturated, (partially) unsaturated or aromatic ring systems and each aryl residue can be present in unsubstituted or mono- or polysubstituted form, wherein the aryl substituents are the same or different and can be in any desired and possible position of the aryl. Preferred aryls are phenyl, naphthyl, anthracenyl, phenanthrenyl, fluoroanthenyl, fluoroenyl, indanyl and tetralinyl. Phenyl and naphthyl are particularly preferred. Where aryl is mono- or polysubstituted, the aryl substituents can be the same or different and be in any desired and possible position of the aryl, and are selected independently of one another from the group comprising —F, —Cl, —Br, —I, —CN, —$NO_2$, —CHO, =O, —$R_0$, —C(=O)$R_0$, —C(=O)OH, —C(=O)O$R_0$, —C(=O)$NH_2$, —C(=O)NH$R_0$, —C(=O)N($R_0$)$_2$, —OH, —O(CH$_2$)$_{1-2}$O—, —O$R_0$, —OC(=O)H, —OC(=O)$R_0$, —OC(=O)O$R_0$, —OC(=O)NH$R_0$, —OC(=O)N($R_0$)$_2$, —SH, —S$R_0$, —$SO_3$H, —S(=O)$_{1-2}$—$R_0$, —S(=O)$_{1-2}$NH$_2$, —$NH_2$, —NH$R_0$, —N($R_0$)$_2$, —$N^+$($R_0$)$_3$, —$N^+$($R_0$)$_2O^-$, —NHC(=O)$R_0$, —NHC(=O)O$R_0$, —NHC(=O)$NH_2$, —NHC(=O)NH$R_0$, —NHC(=O)N($R_0$)$_2$, —Si($R_0$)$_3$, —PO(O$R_0$)$_2$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-methyl-phenyl, 3-methyl-phenyl, 4-methyl-phenyl, 2,3-dimethyl-phenyl, 2,4-dimethyl-phenyl and 3,4-dimethyl-phenyl.

Heteroaryl preferably stands for a 5-, 6- or 7-membered cyclic aromatic residue that contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle, the substituents can be the same or different and can be in any desired and possible position of the heteroaryl; and wherein the heterocycle can also be part of a bi- or polycyclic system. "Heteroaryl" is preferably selected from the group comprising pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding can occur via any desirable and possible ring member of the heteroaryl residue. Where heteroaryl is mono- or polysubstituted, the heteroaryl substituents can be the same or different and can be in any desirable and possible position of the heteroaryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NH—C(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$.

With respect to "aryl" or "heteroaryl", "mono- or polysubstituted" are understood to mean the mono- or polysubstitution, e.g. di-, tri-, 4- or 5-substitution, of one or more hydrogen atoms of the ring system.

Particularly preferred are the substituents or aryl and heteroaryl respectively selected independently of one another from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O$^-$, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_2$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds, in which "aryl substituted" or "heteroaryl substituted" means aryl or heteroaryl substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, are preferred. Particularly preferred substituents are —F, —Cl, —OH, —SH, —NH$_2$ and —C(=O)OH.

The compounds according to the invention can be present in the form of a single stereoisomer or mixture thereof, the free compounds and/or their physiologically compatible salts and/or solvates.

The compounds according to the invention can be chiral or achiral, depending on the substitution pattern.

Depending on the substitution with respect to the cyclohexane ring the compounds according to the invention can be isomers, in which the substitution pattern in 1,4 position (1 position: >C(NR$_1$R)R$_3$; 4 position: >CHNCHQC(=X)R$_5$) can also be referred to as syn/anti. "Syn/anti isomers" are a subgroup of the stereoisomers (configuration isomers).

In a preferred embodiment, the diastereomer excess of the syn-isomer amounts to at least 50% de, more preferred at least 75% de, more preferred at least 90% de, most preferred at least 95% de, and in particular at least 99% de. In another preferred embodiment, the diastereomer excess of the anti-isomer amounts to at least 50% de, more preferred at least 75% de, more preferred at least 90% de, most preferred at least 95% de, and in particular at least 99% de. The two diastereomers differ in their polarity, and therefore in the following the non-polar diastereomer is different from the polar diastereomer. The two diastereomers (in the case of two stereo centres) are present in the form of enantiomer pairs (RR+SS or RS+SR).

Suitable methods for separating the isomers (diastereomers) are known to the person skilled in the art. Column chromatography, preparative HPLC and crystallisation processes can be given as examples. The polarity is, for example, responsible for the sequence in which the two diastereomers are eluted in thin-film chromatography (no reversed phase conditions).

If the compounds according to the invention are chiral, then they are preferably present as racemate or in concentrated form of an enantiomer. In a preferred embodiment the enantiomer excess(ee) of the S-enantiomer amounts at least 50% ee, more preferred at least 75% ee, more preferred at least 90% ee, most preferred at least 95% ee, and in particular at least 99% ee. In another preferred embodiment, the enantiomer excess (ee) of the R-enantiomer amounts to at least 50% ee, more preferred at least 75% ee, more preferred at least 90% ee, most preferred at least 95% ee, and in particular at least 99% ee.

Suitable methods for separating the enantiomers are known to the person skilled in the art. Preparative HPLC on chiral stationary phases and conversion into diastereomeric intermediates can be given as examples. The conversion into diastereomeric intermediates can occur, for example, as salt formation by means of chiral, enantiomer-pure acids. After separation of the diastereomers thus formed, the salt can then be converted into the free base or another salt again.

Unless expressly specified, each reference to the compounds according to the invention covers all isomers (e.g. stereoisomers, diastereomers, enantiomers) in any desired mixture ratio.

Unless expressly specified, each reference to the compounds according to the invention covers the free compounds (i.e. the forms that are not present in the form of salt) and all physiologically compatible salts.

For the purposes of the description, physiologically compatible salts of the compounds according to the invention are present as salts with anions or acids of the respective compound with inorganic or organic acids, which are physiologically compatible—in particular on application in humans and/or mammals.

Examples of physiologically compatible salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxo-proline, hexane-1-sulphonic acid, nicotinic acid, 2-, 3- or 4-aminobenzoic acid, 2,4,6-trimethyl benzoic acid, α-liponic acid, acetylglycine, acetylsalicylic acid, hippuric acid and/or aspartic acid. The hydrochloride, citrate and hemicitrate are particularly preferred.

Physiologically compatible salts with cations or bases are salts of the respective compound—as anion with at least one, preferably inorganic, cation, which are physiologically compatible—in particular on application in humans and/or mammals. Particularly preferred are the salts of the alkali and earth alkali metals, also ammonium salts, but in particular (mono-) or (di-) sodium, (mono-) or (di-) potassium, magnesium or calcium salts.

Respectively preferred embodiments of the compounds according to the invention are explained below. Unless expressly specified, all definitions of the respective substituents explained previously (i.e. from R$_0$ to R$_7$, Y$_1$ to Y$_4$', Q, X etc., for example) and their respective embodiments apply accordingly and will not therefore be repeated.

Preferred embodiments of the compounds of the general formula (1) according to the invention have the general formula (1.1) or (1.2):

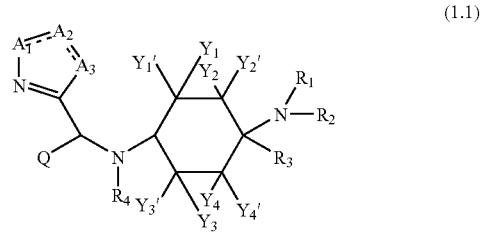

(1.1)

-continued (1.2)

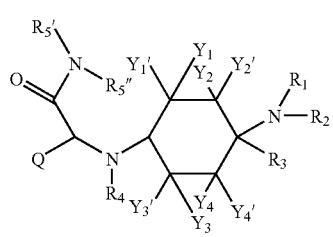

wherein, where present,
$A_1$ stands for —N=, —NH—, —NR$_8$— or —CR$_8$=;
$A_2$ stands for =N—, —C(=O)— or =CR$_9$—;
$A_3$ stands for —O—, —NH— or —NR$_{10}$—; and;
$R_5'$, $R_5''$, $R_8$, $R_9$ and $R_{10}$ respectively independently of one another stand for —H, =O or —C$_{1-8}$-aliphatic.

Preferably $R_5'$ and $R_5''$ respectively independently of one another stand for —H or —C$_{1-8}$-aliphatic.

For the purpose of the description "═══" stands for a double bond or for a single bond. A person skilled in the art knows that the bond between $A_1$ and $A_2$ usually cannot be a double bond, if the bond between $A_2$ and $A_3$ is already a double bond, and vice versa. Moreover, the person skilled in the art knows that a specific number of hydrogen atoms is possibly present as substituents.

Further preferred embodiments of the compounds of the general formula (1) according to the invention have the general formula (2), (3), (4), (5) or (6):

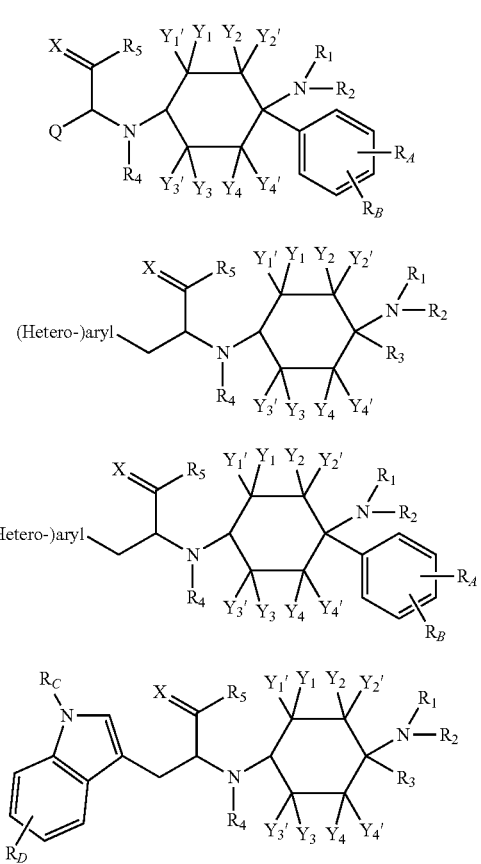

-continued (6)

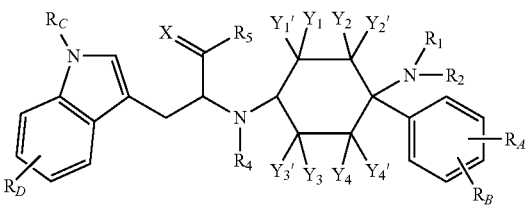

wherein, where present,
$R_A$, $R_B$, $R_C$ and $R_D$ are respectively selected independently of one another from the group comprising —H, —C$_{1-8}$-aliphatic, —OH, —OC$_{1-8}$-aliphatic, —CF$_3$, —F, —Cl, —Br, —NO$_2$, —CN, -heteroaryl, —C$_{1-8}$-aliphatic-aryl and —C$_{1-8}$-aliphatic-heteroaryl; and (hetero)aryl stands for heteroaryl or aryl.

In this case, -aryl and -heteroaryl can respectively be unsubstituted or mono- or polysubstituted, preferably with substituents that are selected independently of one another from the group comprising —C$_{1-8}$-aliphatic, —OH, —OC$_{1-8}$-aliphatic, —CF$_3$, —F, —Cl, —Br, —NO$_2$, —CN, -heteroaryl, —C$_{1-8}$-aliphatic-aryl and —C$_{1-8}$-aliphatic-heteroaryl (e.g. -ethyl-4-pyridyl).

In a preferred embodiment (hetero)aryl is selected from the group comprising phenyl, benzyl, pyrrolyl, furyl, thienyl, pyridyl, indolyl, benzofuryl and benzothienyl, wherein these can be respectively unsubstituted or mono- or polysubstituted, preferably with substituents that are selected independently of one another from the group comprising —C$_{1-8}$-aliphatic, —OH, —OC$_{1-8}$-aliphatic, —CF$_3$, —F, —Cl, —Br, —NO$_2$, —CN, -aryl, -heteroaryl, —C$_{1-8}$-aliphatic-aryl and —C$_{1-8}$-aliphatic-heteroaryl (e.g. -ethyl-4-pyridyl).

Preferred embodiments of the compounds of the general formula (2) have the general formula (2.1), (2.2), (2.3) or (2.4):

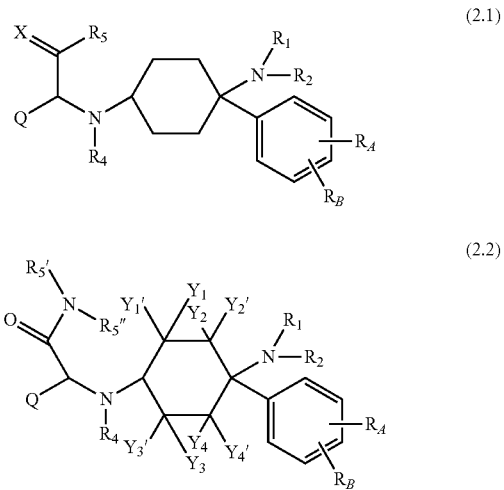

(2.3)
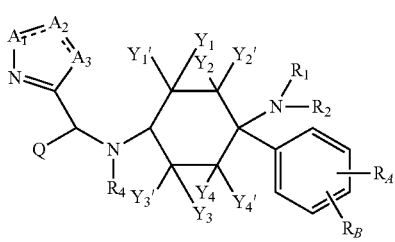

(2.4)
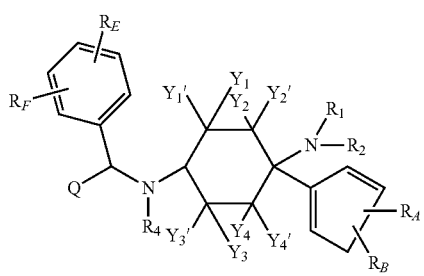

wherein, where present, $R_E$ and $R_F$ are respectively selected independently of one another from the group comprising —H, —$C_{1-8}$-aliphatic, —OH, —O$C_{1-8}$-aliphatic, —CF$_3$, —F, —Cl, —Br, —NO$_2$, —CN, -heteroaryl, —$C_{1-8}$-aliphatic-aryl and —$C_{1-8}$-aliphatic-heteroaryl.

Preferred embodiments of the compounds of the general formula (3) have the general formula (3.1), (3.2), (3.3), or (3.4):

(3.1)
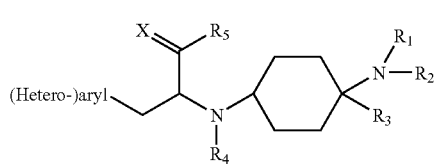

(3.2)
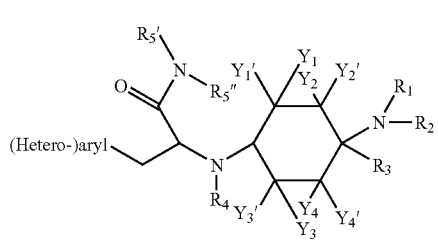

(3.3)
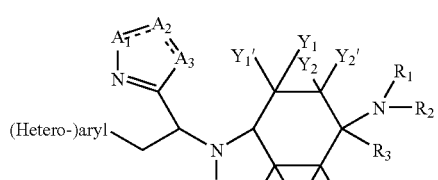

(3.4)
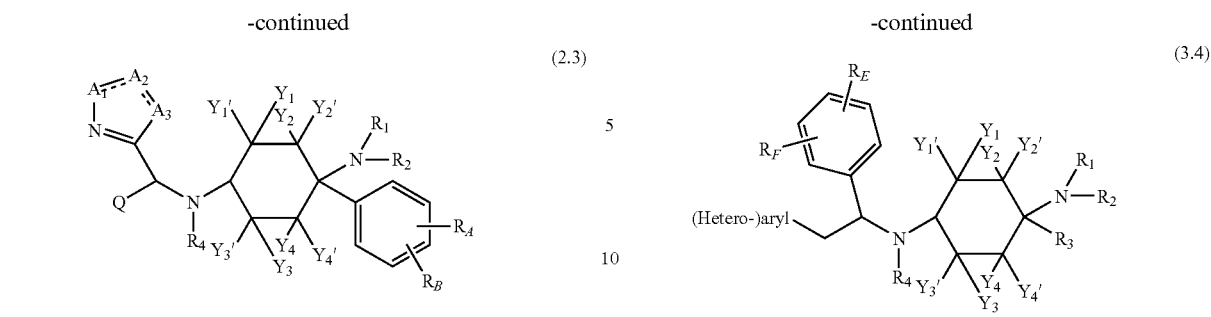

Preferred embodiments of the compounds of the general formula (4) have the general formula (4.1), (4.2), (4.3) or (4.4):

(4.1)
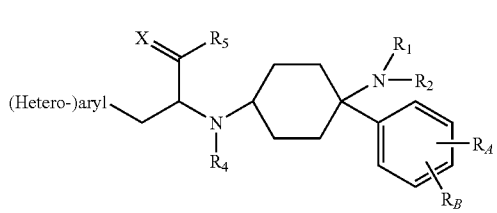

(4.2)
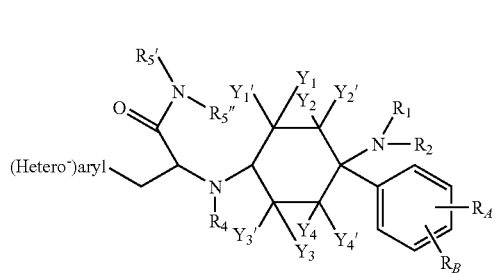

(4.3)
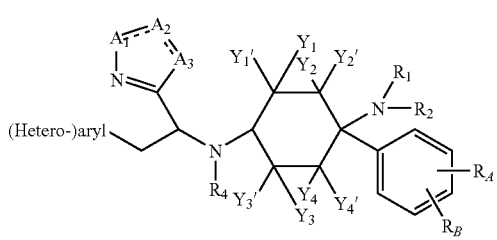

(4.4)
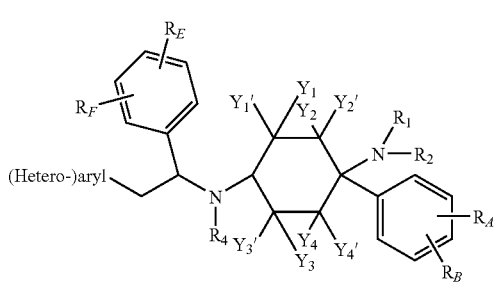

Preferred embodiments of the compounds of the general formula (5) have the general formula (5.1), (5.2), (5.3) or (5.4):

(5.1) 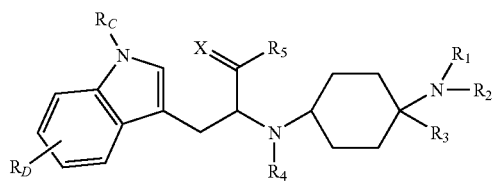

(5.2) 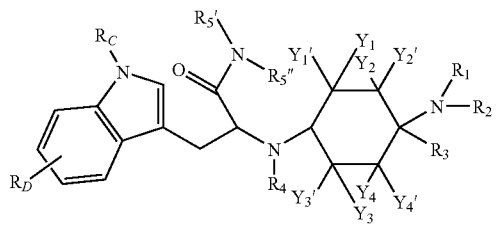

(5.3) 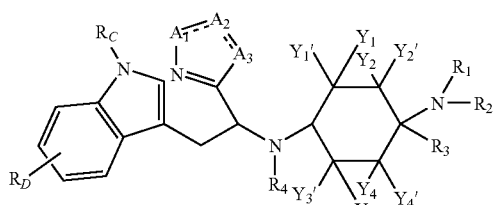

(5.4) 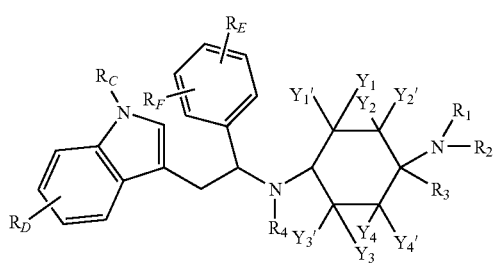

Preferred embodiments of the compounds of the general formula (6) have the general formula (6.1), (6.2), (6.3) or (6.4):

(6.1) 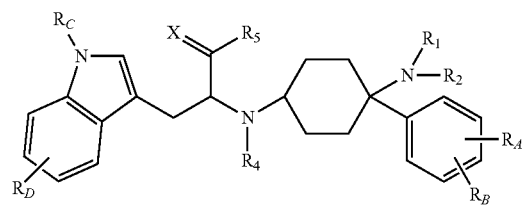

(6.2) 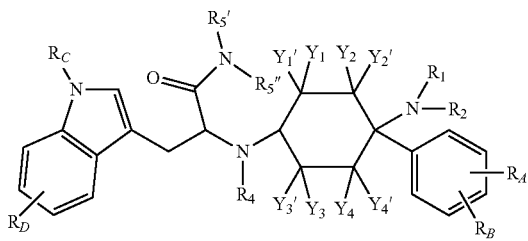

(6.3) 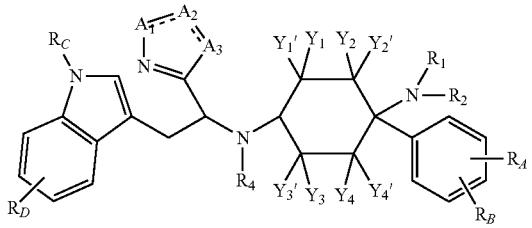

(6.4) 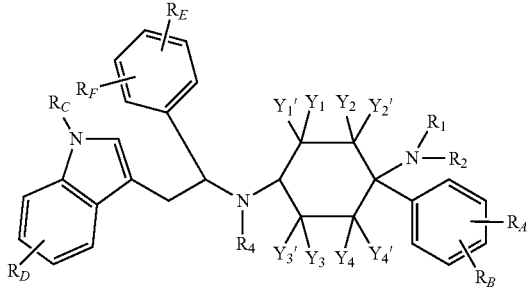

The compounds according to the invention are defined by substituents, e.g. by $R_1$, $R_2$ and $R_3$ (substituents of the first generation), which are themselves possibly substituted (substituents of the second generation). Depending on the definition, these substituents of the substituents can themselves be substituted again (substituents of the third generation). If, for example, $Y_1 = -R_0$, wherein $-R_0 = -C_{1-8}$-aliphatic (substituent of the first generation), then $-C_{1-8}$-aliphatic can itself be substituted, e.g. with $-OR_0$, wherein $R_0$=-aryl (substituent of the second generation). This gives the functional group $-C_{1-8}$-aliphatic-O-aryl. -Aryl can then in turn be substituted again, e.g. with —Cl (substituent of the third generation). This then gives overall the functional group $-C_{1-8}$-aliphatic-O-aryl-Cl.

In a preferred embodiment, the substituents of the third generation cannot be substituted again, i.e. there are then no substituents of the fourth generation.

In another preferred embodiment, the substituents of the second generation cannot be substituted again, i.e. there are then already no substituents of the third generation. In other words, in this embodiment the functional groups for $R_0$ to $R_7$ can possibly be respectively substituted, but the respective substituents cannot then themselves be substituted again.

In another preferred embodiment, the substituents of the first generation cannot be substituted again, i.e. there are then neither substituents of the second generation nor substituents of the third generation. In other words, in this embodiment the functional groups for $R_0$ to $R_7$ are not respectively substituted.

Compounds of the following group are most particularly preferred:

(S)-2-(4-(dimethylamino)-4-phenylcyclohexylamino)-3-(1H-indol-3-yl)propanamide;
(S)-2-(4-(dimethylamino)-4-phenylcyclohexylamino)-3-(1H-indol-3-yl)propanamide;
(±)-2-(4-(dimethylamino)-4-phenylcyclohexylamino)-3-(1H-indol-3-yl)propanamide;
(±)-2-(4-(dimethylamino)-4-phenylcyclohexylamino)-3-(1H-indol-3-yl)propanamide;
(S)-2-(4-(dimethylamino)-4-phenylcyclohexylamino)-3-(1H-indol-3-yl)-N,N-dimethylpropanamide;

(S)-2-(4-(dimethylamino)-4-phenylcyclohexylamino)-3-(1H-indol-3-yl)-N,N-dimethylpropanamide;
(S)-2-(4-(dimethylamino)-4-phenylcyclohexylamino)-3-(1H-indol-3-yl)-N-methyl-propanamide;
(S)-2-(4-(dimethylamino)-4-phenylcyclohexylamino)-3-(1H-indol-3-yl)-N-methyl-propanamide;
5-((S)-1-(4-(dimethylamino)-4-phenylcyclohexylamino)-2-(1H-indol-3-yl)ethyl)-1,3,4-oxadiazol-2(3H)-one;
5-((S)-1-(4-(dimethylamino)-4-phenylcyclohexylamino)-2-(1H-indol-3-yl)ethyl)-1,3,4-oxadiazol-2(3H)-one;
N4-((S)-2-(1H-indol-3-yl)-1-(3-methyl-1,2,4-oxadiazol-5-yl)ethyl)-N1,N1-dimethyl-1-phenylcyclohexane-1,4-diamine;
5-((R)-1-(4-(dimethylamino)-4-phenylcyclohexylamino)-2-(1H-indol-3-yl)ethyl)-1,3,4-oxadiazol-2(3H)-one;
5-((R)-1-(4-(dimethylamino)-4-phenylcyclohexylamino)-2-(1H-indol-3-yl)ethyl)-1,3,4-oxadiazol-2(3H)-one;
N4-((R)-2-(1H-indol-3-yl)-1-(3-methyl-1,2,4-oxadiazol-5-yl)ethyl)-N1,N1-dimethyl-1-phenylcyclohexane-1,4-diamine;
N4-((R)-2-(1H-indol-3-yl)-1-(3-methyl-1,2,4-oxadiazol-5-yl)ethyl)-N1,N1-dimethyl-1-phenylcyclohexane-1,4-diamine;
N4-((S)-2-(1H-indol-3-yl)-1-(5-methyloxazol-2-yl)ethyl)-N1,N1-dimethyl-1-phenyl-cyclohexane-1,4-diamine;
N4-((S)-2-(1H-indol-3-yl)-1-(5-methyloxazol-2-yl)ethyl)-N1,N1-dimethyl-1-phenyl-cyclohexane-1,4-diamine;
N4-(2-(1H-indol-3-yl)-1-(1H-tetrazol-5-yl)ethyl)-N1,N1-dimethyl-1-phenylcyclohexane-1,4-diamine;
N4-(2-(1H-indol-3-yl)-1-phenylethyl)-N1,N1-dimethyl-1-phenylcyclohexane-1,4-diamine;
N4-(2-(1H-indol-3-yl)-1-(1H-tetrazol-5-yl)ethyl)-N1,N1,N4-trimethyl-1-phenylcyclohexane-1,4-diamine;
N4-(2-(1H-indol-3-yl)-1-phenylethyl)-N1,N1,N4-trimethyl-1-phenylcyclohexane-1,4-diamine;
N4-(2-(1H-indol-3-yl)-1-(3-methyl-1,2,4-oxadiazol-5-yl)ethyl)-N1,N1,N4-trimethyl-1-phenylcyclohexane-1,4-diamine;
N4-(2-(1H-indol-3-yl)-1-(5-methyloxazol-2-yl)ethyl)-N1,N1,N4-trimethyl-1-phenyl-cyclohexane-1,4-diamine;
5-(1-((4-(dimethylamino)-4-phenylcyclohexyl)(methyl)amino)-2-(1H-indol-3-yl)ethyl)-1,3,4-oxadiazol-2(3H)-one;
2-((4-(dimethylamino)-4-phenylcyclohexyl)(methyl)amino)-3-(1H-indol-3-yl)-N,N-dimethylpropanamide;
N4-(2-(1H-indol-3-yl)-1-(3-methyl-1,2,4-oxadiazol-5-yl)ethyl)-1-(3-fluorophenyl)-N1,N1-dimethylcyclohexane-1,4-diamine;
N4-(2-(1H-indol-3-yl)-1-(5-methyloxazol-2-yl)ethyl)-1-(3-fluorophenyl)-N1,N1-dimethylcyclohexane-1,4-diamine;
N-(2-(1H-indol-3-yl)-1-(5-methyloxazol-2-yl)ethyl)-N-(4-(dimethylamino)-4-(3-fluorophenyl)cyclohexyl)cinnamic acid amide; and
N-(2-(1H-indol-3-yl)-1-(3-methyl-1,2,4-oxadiazol-5-yl)ethyl)-N-(4-(dimethylamino)-4-(3-fluorophenyl)cyclohexyl)cinnamic acid amide;
(R)—N4-(2-(1H-indol-3-yl)-1-(5-methyloxazol-2-yl)ethyl)-N1,N1-dimethyl-1-phenylcyclohexane-1,4-diamine;
(S)—N4-(2-(1H-indol-3-yl)-1-(4-methylthiazol-2-yl)ethyl)-N1,N1-dimethyl-1-phenylcyclohexane-1,4-diamine;
(R)—N4-(2-(1H-indol-3-yl)-1-(4-methylthiazol-2-yl)ethyl)-N1,N1-dimethyl-1-phenylcyclohexane-1,4-diamine;
N4-(2-(1H-indol-3-yl)-1-phenylethyl)-N1,N1-dimethyl-1-phenylcyclohexane-1,4-diamine dihydrochloride;
N-(2-(1H-indol-3-yl)-1-(1H-tetrazol-5-yl)ethyl)-N-(4-dimethylamino-4-phenylcyclohexyl)-2,2,2-trifluoroacetamide;
N4-(2-(1H-indol-3-yl)-1-(1H-tetrazol-5-yl)ethyl)-N1,N1-dimethyl-1-phenylcyclohexane-1,4-diamine;
or physiologically compatible salts and/or solvates thereof.

The compounds according to the invention act, for example, on the relevant ORL 1-receptor in association with different diseases, and therefore they are suitable as pharmaceutical active substance in a medication.

Therefore, the invention additionally relates to medications, which contain at least one compound according to the invention, as well as possibly suitable additives and/or adjuvants and/or possibly further active substances.

The compounds according to the invention have an affinity to the -opioid or to the ORL 1-receptor and are therefore suitable for drug development.

Besides at least one compound according to the invention, the medications according to the invention possibly contain suitable additives and/or adjuvants, hence also support materials, fillers, solvents, dilutants, colouring agents and/or binders, and can be administered as liquid medications in the form of injectable solutions, drops or juices, as semisolid medications in the form of granules, tablets, pellets, patches, capsules, plasters/spray plasters or aerosols. The selection of adjuvants etc. as well as the quantities thereof to be used are dependent on whether the medication is to be applied orally, perorally, parenterally, intravenously, intraperitoneally, intradermally, intramuscularly, intranasally, bucally, rectally or locally, e.g. onto the skin, mucous membranes or into the eyes. Preparations in the form of tablets, coated tablets, capsules, granules, drops, juices and syrups are suitable for oral application, solutions, suspensions, readily reconstituted dry preparations as well as sprays are suitable for parenteral, topical and inhalatory application. Compounds according to the invention in a depot, in dissolved form or in a plaster, possibly with the addition of skin-penetration promoters, are suitable preparations for percutaneous application. Preparation forms that may be applied orally or percutaneously can release the compounds according to the invention in a delayed manner. The compounds according to the invention can also be applied in parenteral long-term depot forms such as e.g. implants or implanted pumps. In principle, other additional active substances known to the skilled person can be added to the medications according to the invention.

The amount of active substance to be administered to the patient varies depending on the weight of the patient, on the type of application, the indication and the degree of severity of the disease. Usually, 0.00005 to 50 mg/kg, preferably 0.001 to 0.5 mg/kg, of at least one compound according to the invention are applied.

For all the above-mentioned forms of the medication according to the invention it is particularly preferred if, besides at least one compound according to the invention, the medication also contains a further active substance, in particular an opioid, preferably a strong opioid, in particular morphine, or an anaesthetic, preferably hexobarbital or halothane.

In a preferred form of the medication, a contained compound according to the invention is present in the form of pure diastereomer and/or enantiomer.

The ORL 1-receptor was identified in particular in the pain process. Compounds according to the invention can be used accordingly for the production of a medication for the treatment of pain, in particular of acute, neuropathic or chronic pain.

Therefore, the invention additionally relates to the use of a compound according to the invention for the production of a medication for the treatment of pain, in particular of acute, visceral, neuropathic or chronic pain.

The invention further relates to the use of a compound according to the invention for the treatment of anxiety conditions, stress and stress-related syndromes, depressive illnesses, epilepsy, Alzheimer's disease, senile dementia, general cognitive dysfunctions, learning and memory disabilities (as nootropic), withdrawal symptoms, alcohol and/or drug and/or medication misuse and/or dependence, sexual dysfunctions, cardiovascular diseases, hypotension, hypertension, tinitus, pruritus, migraine, hearing impairment, deficient intestinal motility, eating disorders, anorexia, bulimia, mobility disorders, diarrhoea, cachexia, urinary incontinence, or as muscle relaxant, anticonvulsive or anaesthetic, or for coadministration in the treatment with an opioid analgesic or with an anaesthetic, for diuresis or anti-natriuresis, anxiolysis, for modulating movement activity, for modulating neurotransmitter release and for treating neuro-degenerative diseases associated therewith, for treating withdrawal symptoms and/or for reducing the addiction potential of opioids.

In this case, it can be preferred in one of the above uses if a used compound is present as a pure diastereomer and/or enantiomer, as a racemate or as non-equimolar or equimolar mixture of the diastereomers and/or enantiomers.

The invention additionally relates to a method for treating, in particular in one of the aforementioned indications, a non-human mammal or human, which or who requires a treatment for pain, in particular chronic pain, by the administration of a therapeutically effective dose of a compound according to the invention or a medication according to the invention.

The invention further relates to a method for producing the compounds according to the invention as outlined in the following description and examples.

Synthesis of Compounds of Type 1 a) Method 1

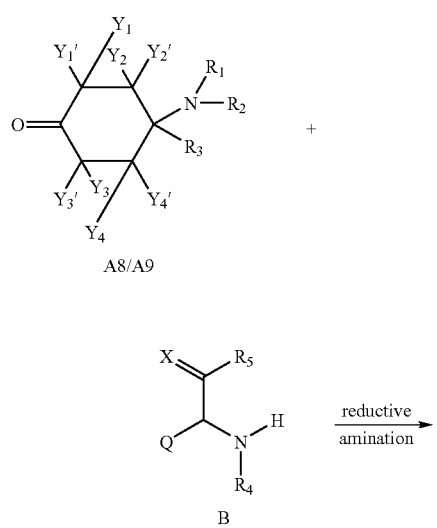

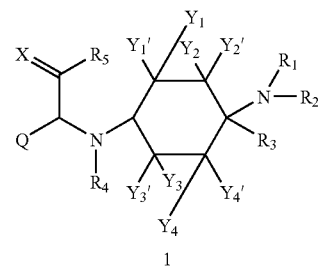

Ketones of the general formula A8/A9 can be converted to compounds of the general formula 1 by a reductive amination with amines of the general structure B in at least one organic solvent, preferably from the group comprising diethyl ether, methanol, ethanol, dichloroethane, dichloromethane and toluol, by adding at least one reducing agent, preferably from the group comprising borane-pyridine complex, sodium boron hydride, sodium triacetoxyboron hydride, sodium cyanoboron hydride and triethyl silane possibly in the presence of at least one acid, preferably selected from the group comprising formic acid, acetic acid, hydrochloric acid and trifluoroacetic acid at temperatures of preferably −70° C. to 150° C. possibly with microwave irradiation. An acylation, alkylation or sulphonation is possibly conducted in the case of compounds of the general formula 1 where $R_4$=H, or in the case of compounds where $R_4$=H protected by a protective group, a protective group is split off at least once and acylation, alkylation or sulphonation is possibly conducted.

b) Method 2

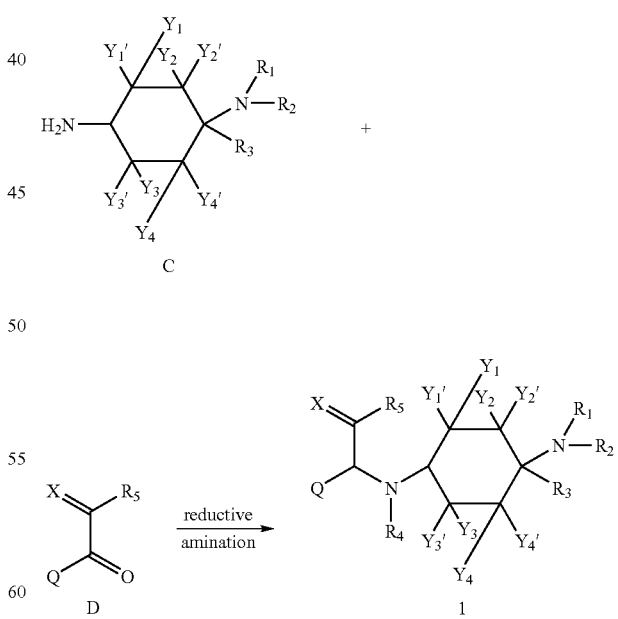

Alternatively, amines of the general structure C can be converted to compounds of the general formula 1 with ketones of the general structure D in the sense of a reductive amination (see above).

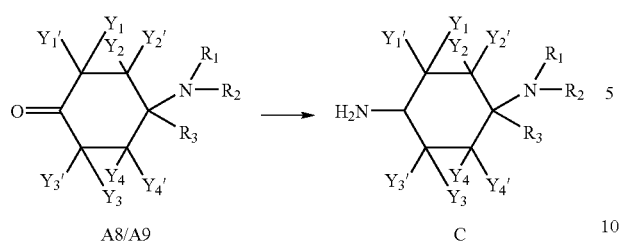

Amines of the general structure C can be obtained from ketones of the general structure A8/A9 using methods known to the person skilled in the art, e.g. by conversion into corresponding oximes and subsequent reduction.

Synthesis of the Ketone Unit A8/A9 a) Derivatisation in the 2,3,5 and/or 6 Position of Cyclohexane Dione Ketone Acetals

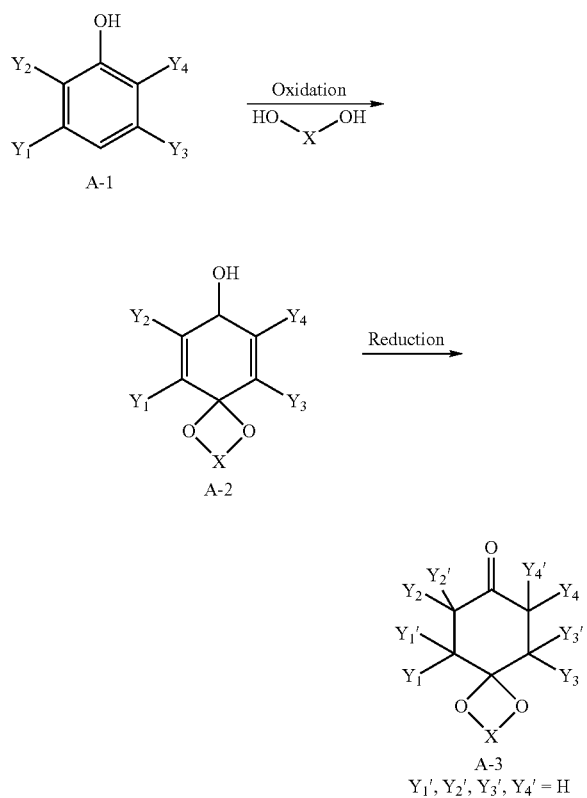

Substituted cyclohexane dione ketone acetals of the type A-3 can be synthesised from the known A-1 educts using methods known to the person skilled in the art. The oxidation of A-1 phenols by means of hypervalent iodine reagents to form the intermediate A-2 cyclohexadienone ketone acetals is described in the specialist literature (Rose et al., Can. J. Chem., 74, 1996, 1836). Compounds of formula A-3 can then be obtained from the corresponding A-2 ketone acetals using methods known to the skilled person by reduction in a hydrogen atmosphere and in the presence of metal catalysts, e.g. rhodium-based catalysts.

b) Derivatisation in the 2 Position of Cyclohexane Dione Ketone Acetals

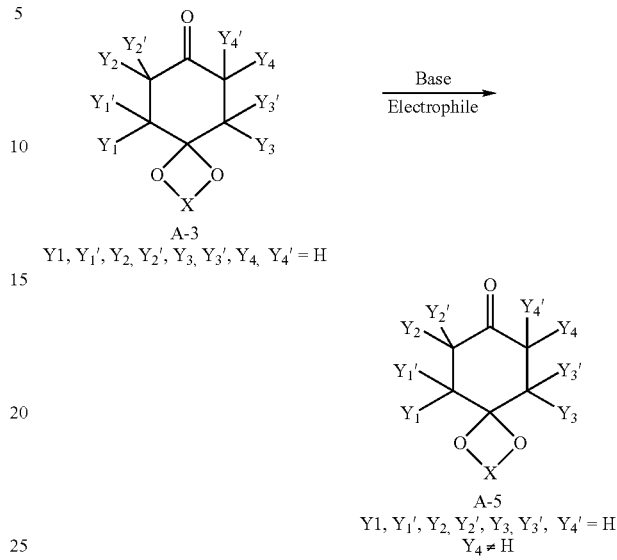

α-substituted cyclohexane dione ketone acetals of the general formula A-5 can be converted by converting the unsubstituted A-3 ketone acetals with a base, e.g. lithium diisopropylamide (LDA), lithium hexamethyl disilazide (LHMDS), potassium hexamethyl disilazide (KHMDS), sodium hydride (NaH), potassium hydride (KH), sodium methanolate (NaOMe), potassium tert-butoxylate ($K^1OBu$), amine bases such as e.g. diethylamine ($HNEt_2$), diisopropylethylamine (Hünig's base), piperidine, pyrrolidine, proline, and with the corresponding electrophiles e.g. of the type $Y_4$—X (with X=e.g. Br, I, OTos, OTf etc. and $Y_4$=e.g. alkyl, benzyl) in organic solvents or solvent mixtures, e.g. dichloromethane (DCM), dichloroethane (DCE), diethyl ether ($Et_2O$), tetrahydrofuran (THF), dimethoxyethane (DME), methanol (MeOH), ethanol (EtOH), dimethylformamide (DMF), dimethylsulphoxide (DMSO) at temperatures between −78° C. and 150° C. Moreover, the generated anion can be converted with corresponding Michael acceptor systems. The introduction of heteroatoms can occur by conversion with disulphur compounds ($Y_4$=S-alkyl or S-aryl), corresponding electrophilic fluorination reagents such as e.g. Selectfluor™ ($Y_4$=F), corresponding electrophilic amination reagents such as e.g. N-alkoxycarbonyl- or N-carboxamido-oxaziridines ($Y_4$=$NR_2$) or corresponding electrophilic hydroxylation reagents such as e.g. oxodiperoxy molybdenum(pyridine)(hexamethyl phosphorus triamide) complex (MOOPH ($Y_4$=OH). Aldol-type conversions can also occur in acid medium. Moreover, substituents; can be introduced by means of a Mannich reaction under acid conditions (camphorsulphonic acid, p-TosOH etc.).

The syntheses of the cyclohexanone derivatives with the general formula A-3 are known in the specialist literature (WO05066183, WO040043967, WO0290317, U.S. Pat. No. 4,065,573, Lednicer et al., J. Med. Chem., 23, 1980, 424-430.)

c) Synthesis of Amino Cyclohexanones
(1) Aminonitrile/Triazole Route

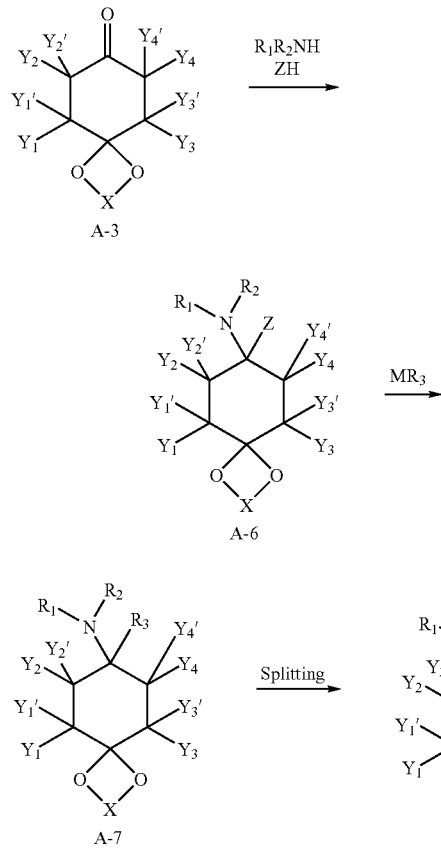

Structures of formula A-6 can be produced by reaction of A-3 ketones with amines and acid Z—H reactants. Suitable Z—H reactants are e.g. hydrogen cyanide, 1,2,3-triazole, benzotriazole or pyrazole.

A particularly preferred route to compounds of A-6 structure is the conversion of ketones with metal cyanides and the corresponding amine in the presence of acid, preferably in an alcohol, at temperatures of –40° to 60° C., preferably at room temperature with alkali metal cyanides in methanol.

A further particularly preferred route to compounds of A-6 structure is the conversion of ketones with 1,2,3-triazole and the corresponding amine in the presence ? under dehydrating conditions, preferably using a water separator at elevated temperature in an inert solvent, or using a molecular sieve or another dehydrating agent. A-6 analogous structures can be introduced in a similar manner with benzotriazole or pyrazole groups instead of triazole groups.

In general, A-7 ketone acetals can also be obtained by substituting suitable Z leaving groups in structures of formula A-6. Suitable leaving groups are preferably cyano groups; 1,2,3-triazol-1-yl groups. Further suitable leaving groups are 1H-benzo[d][1,2,3]triazol-1-yl groups and pyrazol-1-yl groups (Katritzky et al., Synthesis 1989, 66-69).

A particularly preferred route to compounds of A-7 structure is the conversion of A-6 aminonitriles with corresponding organometallic compounds, preferably Grignard compounds, preferably in ethers, preferably at room temperature. The organometallic compounds are either commercially available or can be produced using known methods. A further particularly preferred route to compounds of A-7 structure is the conversion of A-6 aminotriazoles with corresponding organometallic compounds, preferably Grignard compounds, preferably in ethers, preferably at RT.

The organometallic compounds are either commercially available or can be produced using methods known from specialist literature.

Compounds of formula A-8 can be released from corresponding A-7 ketone acetals or from their salts by deprotection by means of acids using methods known to the skilled person. In this case, X is selected from the group, alkyl, alkyl/alkylidene/alkylidene substituted with aryl or alkyl (saturated/unsaturated).

(2) Imine Route

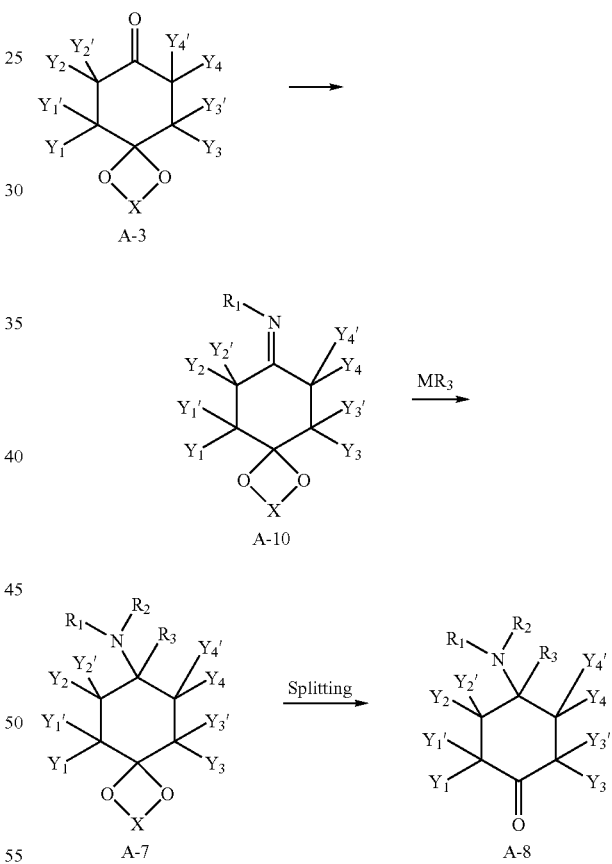

In the imine route, the A-10 imine is synthesised from an A-3 ketone precursor and is converted into the A-7 unit using an $MR_3$ nucleophile and further into A-8. The necessary A-10 imine units can be produced using a method known to the skilled person (Layer, Chem. Rev., 1963, 8, 489-510). Methods known from the specialist literature (e.g. Maddox et al., J. Med. Chem., 1965, 8, 230-235. Kudzma et al., J. Med. Chem., 1989, 32, 2534-2542.) are employed for addition of the $MR_3$ organometallic species to the A-10 imine.

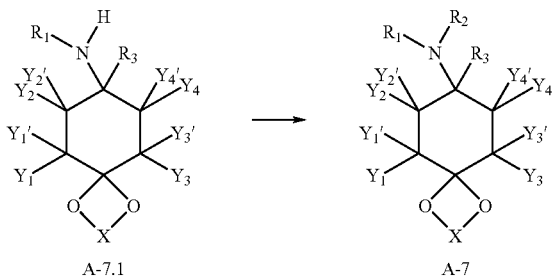

A-7.1   A-7

A-7.1 amino acetals with a maximum of one substituent on the nitrogen atom can be converted into corresponding A-7 amino acetals with one or two further substituents (R2≠H) on the nitrogen atom using methods known in principle to the skilled person, e.g. by reductive amination.

d) Derivatisation in the 2 Position of Amino Cyclohexanones

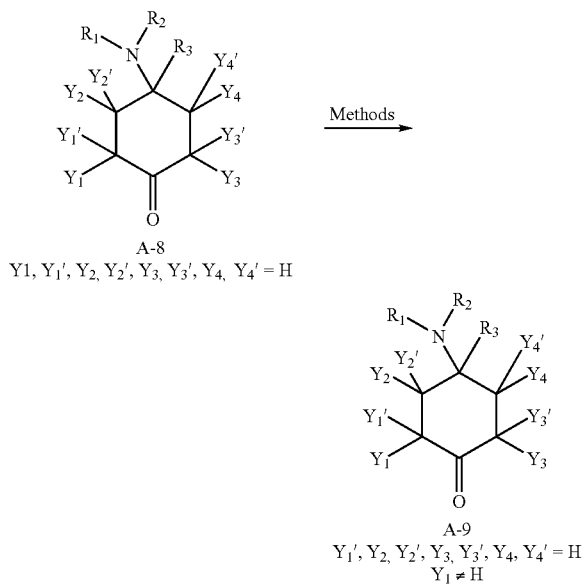

A-8
$Y_1, Y_1', Y_2, Y_2', Y_3, Y_3', Y_4, Y_4' = H$

A-9
$Y_1', Y_2, Y_2', Y_3, Y_3', Y_4, Y_4' = H$
$Y_1 \neq H$

Substituted amino cyclohexanones of type A-9 can be synthesised from the known A-8 educts using methods known to the person skilled in the art.

Method 1:

The α-arylation of A-8 ketones with the corresponding aryl halides, e.g. of type $Y_1$—X (where $Y_1$=aryl/hetaryl and X=Br, I) by palladium catalysis in the presence of suitable phosphine ligands such as e.g. xantphos, is described in the specialist literature (Elliott et al. Bioorg. Med. Chem. Lett.; EN; 16; 11; 2006; 2929; Dirat et al. Tetrahedron Lett.; EN; 47; 8; 2006; 1295.)

Method 2:

α-substituted amino cyclohexanones of type A-9 can be converted by converting unsubstituted A-8 ketone acetals with a base, e.g. lithium diisopropylamide (LDA), lithium hexamethyl disilazide (LHMDS), potassium hexamethyl disilazide (KHMDS), sodium hydride (NaH), potassium hydride (KH), sodium methanolate (NaOMe), potassium tert-butoxylate ($K^1$OBu), amine bases such as e.g. diethylamine (HNEt$_2$), diisopropylethylamine (Hünig's base), piperidine, pyrrolidine, proline, and with the corresponding electrophiles e.g. of the type $Y_4$—X (where X=e.g. Br, I, OTos, OTf etc.) in organic solvents or solvent mixtures, e.g. dichloromethane (DCM), dichloroethane (DCE), diethyl ether (Et$_2$O), tetrahydrofuran (THF), dimethoxyethane (DME), methanol (MeOH), ethanol (EtOH), dimethylformamide (DMF), dimethylsulphoxide (DMSO) at temperatures between −78° C. and 150° C. Moreover, the generated anion can be converted with corresponding Michael acceptor systems. The introduction of heteroatoms can occur by conversion with disulphur compounds ($Y_4$=S-alkyl or S-aryl), corresponding electrophilic fluorination reagents such as e.g. Selectfluor™ ($Y_4$=F), corresponding electrophilic amination reagents such as e.g. N-alkoxycarbonyl- or N-carboxamido-oxaziridines ($Y_4$=NR$_2$) or corresponding electrophilic hydroxylation reagents such as e.g. oxodiperoxy molybdenum(pyridine)(hexamethyl phosphorus triamide) complex (MOOPH ($Y_4$=OH). Aldol-type conversions can also occur in acid medium. Moreover, substituents can be introduced by means of a Mannich reaction under acid conditions (camphorsulphonic acid, p-TosOH etc.).

Synthesis of Amine Units of Type B a) B.1 Amine Units for the Synthesis of Compounds of Type 1-b

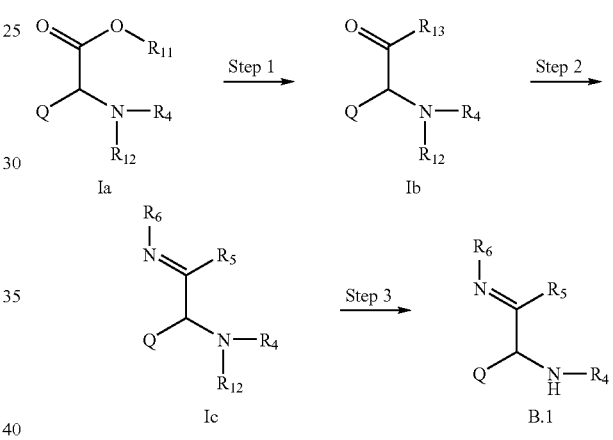

Ia   Ib

Ic   B.1

In step 1 alpha-amino carboxylic acid derivatives of the general formula Ia that are commercially available or known from specialist literature, in which R$_{11}$ represents hydrogen, alkyl, aryl or residues that usually serve to activate carboxylic acids (e.g. N-succinimidyl or chloride) and R$_{12}$ represents typical amine protective groups (e.g. tert-butoxycarbonyl or benzyloxycarbonyl), are converted into alpha-amino carboxylic acid derivatives of formula Ib, in which R$_{13}$ represents e.g. the following residues: —NH$_2$, —NH—NH$_2$, —NH—CH$_2$—C≡CH, —NH—CH$_2$—CH$_2$—OH, —O—N=C(NH$_2$)—CH$_3$.

In step 2 compounds of the general formula Ic are obtained from compounds of the general formula Ib by converting compounds of the general formula Ib to aromatic and non-aromatic heterocycles of the general formula Ic in one or more steps. Thus, the corresponding nitriles are obtained e.g. from compounds of the general formula Ib where R$_{13}$ is —NH$_2$ after dehydration using usual reagents such as e.g. trifluoroacetic anhydride, and said nitriles are converted to 1H-tetrazol-5-yl derivatives by reacting with azides, to 5-methyl-[1,2,4]-oxadiazol-3-yl derivatives by reacting with hydroxylamine and reaction of the intermediate with acetic anhydride or to [1,2,4]oxadiazol-5-yl derivatives by reacting with a C1-unit such as e.g. N,N-dimethylformamide dimethylacetal and further reaction of the intermediate with hydroxylamine. 3H-[1,3,4]oxadiazol-2-on-5-yl derivatives are obtained from compounds of the general formula Ib where $R_{13}$ is —NH—NH$_2$ after reacting with C1-units such as e.g. phosgene or N,N'-carbonyldiimidazole. 5-methyloxazol-2-yl derivatives are obtained from compounds of the general formula Ib where $R_{13}$ is —NH—CH$_2$—C≡CH by the action of catalytic quantities of metal salts such as e.g. gold(III) or mercury(II) salts.

Oxazolin-2-yl derivatives, which react by oxidation to form oxazoles, are obtained from compounds of the general formula Ib where $R_{13}$ is NH—CH$_2$—CH$_2$—OH by dehydration using usual reagents such as e.g. N,N-diethylamino sulphur trifluoride or methoxycarbonyl-sulphamoyl-triethylammonium hydroxide (Burgess reagent). 3-methyl-[1,2,4]oxadiazol-5-yl derivatives are formed from compounds of the general formula Ib where $R_{13}$ is —O—N=C(NH$_2$)—CH$_3$ after dehydration in the presence of e.g. a molecular sieve.

The syntheses of heterocycles using the above-described paths are known in specialist literature (V. Bavetsias et al, J. Med. Chem. 43, 2000, 1910-1926; A. Hamze et al., J. Org. Chem. 68, 2003, 7316-7321; S. Lee et al., Bull. Korean Chem. Soc. 25, 2004, 207-212; A. S. K. Hashmi et al., Org. Lett. 6, 2004, 4391-4394; T. Morwick et al., Org. Lett. 4, 2002, 2665-2668; K. Thompson et al., J. Med. Chem. 41, 1998, 3923-3927).

For Explanation of Step 2

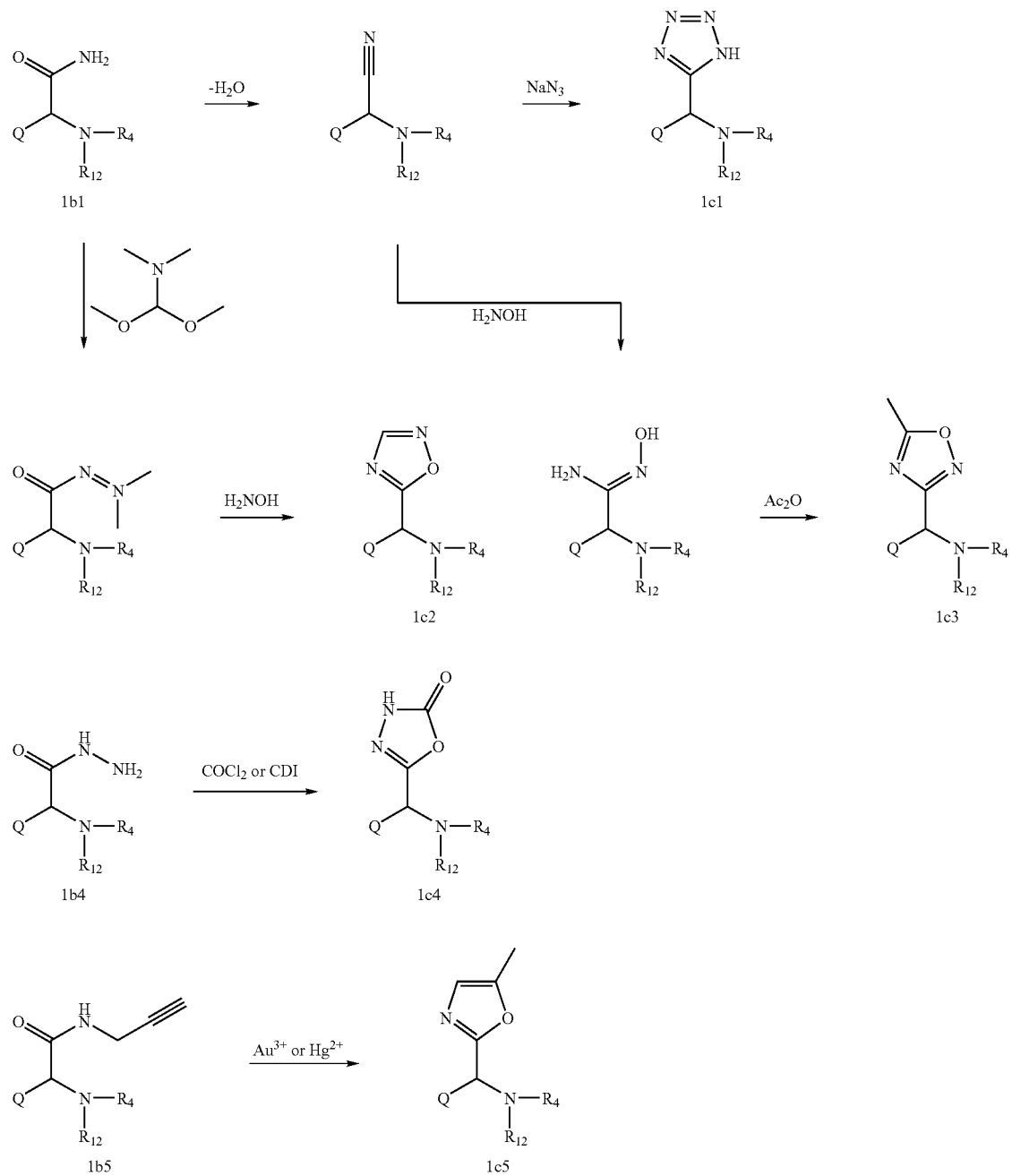

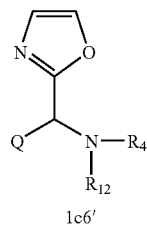
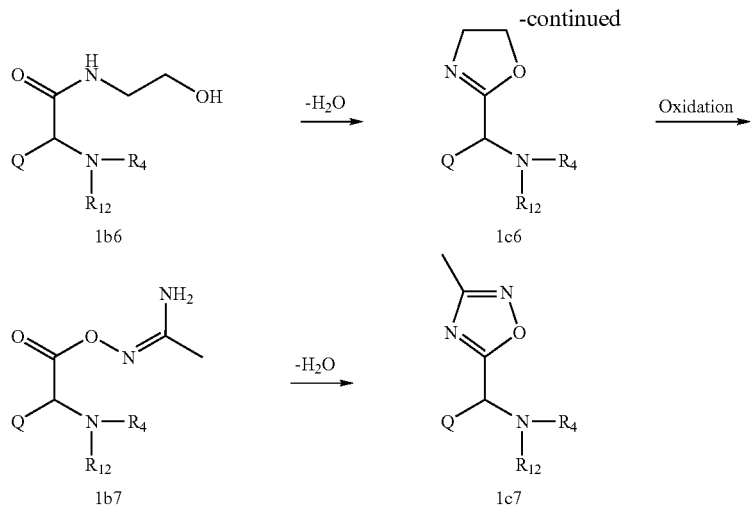

In step 3 the protective groups are split off from the compounds of the general formula Ic in the usual manner, as a result of which the compounds of the general formula B.1 are obtained.

b) B-2 Amine Units for the Synthesis of Compounds of Type 1-2

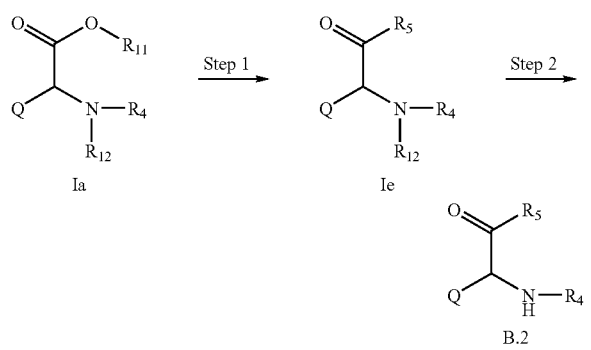

In step 1 alpha-amino carboxylic acid derivatives of the general formula Ia that are commercially available or known from specialist literature, in which $R_{11}$ represents hydrogen, alkyl, aryl or residues that usually serve to activate carboxylic acids (e.g. N-succinimidyl or chloride) and $R_{12}$ represents typical amine protective groups (e.g. tert-butoxycarbonyl or benzyloxycarbonyl), are converted into alpha-amino carboxylic acid derivatives of formula Ie, in which $R_5$ represents, e.g. the following residues: —$NH_2$, —NHMe, —$NMe_2$.

In step 2 the protective groups are split off from the compounds of the general formula Ie in the usual manner, as a result of which the compounds of the general formula B.2 are obtained.

With respect to further details on the synthesis of the compounds according to the invention, reference can be made to the following in their full scope: WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

EXAMPLES

The following examples serve to explain the invention in more detail, while not restricting it.

The yields of the compounds produced are not optimised. All temperatures are uncorrected. The term "ether" means diethyl ether, "EE" ethyl acetate and "DCM" dichloromethane. The term "equivalents" means substance amount equivalents, "mp" melting point or melting range, "decomp." decomposition, "RT" room temperature, "abs." absolute (free from water), "rac." racemic, "conc." concentrated, "min" minutes, "h" hours, "d" days, "% vol." percent by volume, "% m" percent by mass and "M" is a concentration detail in mol/l.

Silica gel 60 (0.040-0.063 mm) from E. Merck, Darmstadt was used as the stationary phase for the column chromatography. The thin-film chromatography tests were conducted with silica gel 60 F 254 HPTLC chromatoplates from E. Merck, Darmstadt. The mixture ratios of mobile solvents for chromatography tests are always given in volume/volume.

Example 1 and Example 2

Step 1

(S)-2-(4-(dimethylamino)-4-phenylcyclohexylamino)-3-(1H-indol-3-yl)propanamide (polar and non-polar diastereomer)

The hydrochloride of L-tryptophanamide (1.49 g, 6.3 mmol) was vigorously stirred with 1,2-dichloroethane (30 ml), tetrahydrofuran (20 ml) and saturated $NaHCO_3$ solution (40 ml) for 15 min and the aqueous phase was then immediately extracted with a tetrahydrofuran/ethyl acetate mixture (1:3.5×40 ml). After drying with $Na_2SO_4$ the organic phase was concentrated to low volume. The released base (1.3 g, 6.3 mmol) and 4-(dimethylamino)-4-phenylcyclohexanone (1.3 g, 6.3 mmol) were dissolved in tetrahydrofuran (40 ml) and 1,2-dichloroethane (30 ml) in argon. Glacial acetic acid (0.37 ml, 6.3 mmol) and $Na_2SO_4$ (3.2 g) were added to the clear solution. After a reaction time of 15 min the reaction mixture was mixed with NaBH(OAc)$_3$ (2 g, 9 mmol) and stirred for 2 d at room temperature. For work up of the batch the mixture was mixed with saturated NaHCO₃ solution (60 ml) and stirred for 15 min. The aqueous phase was extracted with dichloromethane (2×40 ml). The combined organic phases were concentrated to low volume after drying, and a light brown oil was obtained. The chromatographic separation of the substance mixture on silica gel 60 (50 g) was conducted with ethyl acetate/methanol (1:1).

Yield (non-polar diastereomer): 25% (631 mg), beige-coloured solid

Yield (polar diastereomer): 298' mg (12% ), beige-coloured solid

Step 2

(S)-2-(4-(dimethylamino)-4-phenylcyclohexylamino)-3-(1H-indol-3-yl)propanamide; dihydrochloride (Example 1, non-polar diastereomer)

The more non-polar diastereomer from step 1 (600 mg, 1.4 mmol) was dissolved in ethyl methyl ketone (1000 ml) and mixed with Me₃SiCl (0.5 ml, 3.7 mmol). After 1 h a white crystalline solid was aspirated.

Yield: 340 mg (46%)
Melting point: 181-214° C.
13C NMR (101 MHz, DMSO-D6) δ ppm: 22.1, 23.8, 25.0, 26.2, 38.1, 51.2, 58.0, 67.7, 107.2, 111.3, 118.4, 118.5, 120.9, 124.2, 127.2, 128.8, 129.5, 132.6, 135.9, 169.0

(S)-2-(4-(dimethylamino)-4-phenylcyclohexylamino)-3-(1H-indol-3-yl)propanamide; dihydrochloride (Example 2, polar diastereomer)

Me₃SiCl (0.23 ml, 1.7 mmol) was added to a solution of the more polar diastereomer from step 1 (280 mg, 0.69 mmol) in ethyl methyl ketone (20 ml). The solid was aspirated after a reaction time of 1 h.

Yield: 326 (93%)
Melting point: 201-210° C.
13C NMR (101 MHz, DMSO-D6) δ ppm: 23.9, 25.4, 26.2, 28.2, 28.3, 37.2, 54.4, 57.6; 67.6, 106.9, 111.3, 118.3, 118.4, 120.9, 124.3, 127.1, 129.1, 129.6, 135.9, 169.1

Example 3 and Example 4

Step 1

2-(4-(dimethylamino)-4-phenylcyclohexylamino)-3-(1H-indol-3-yl)propanamide dihydrochloride (polar and non-polar diastereomer)

D,L-tryptophanamide hydrochloride (1.49 g, 6.25 mmol) was vigorously stirred with 1,2-dichloroethane (30 ml), tetrahydrofuran (20 ml) and saturated NaHCO₃ solution (40 ml) for 15 min and the aqueous phase was then immediately extracted with a tetrahydrofuran/ethyl acetate mixture (1:3.5×40 ml). After drying with Na₂SO₄ the organic phase was concentrated to low volume. The released base (1.03 g, 5.06 mmol) and 4-(dimethylamino)-4-phenylcyclohexanone (1.09 g, 5.06 mmol) were dissolved in tetrahydrofuran (40 ml) and 1,2-dichloroethane (30 ml) in argon. Glacial acetic acid (0.291 ml, 5.06 mmol) and Na₂SO₄ (2.53 g) were added to the clear solution. After a reaction time of 15 min the reaction mixture was mixed with NaBH(OAc)₃ (1.52 g, 7.08 mmol) and stirred for 2 d at room temperature. For work up of the batch the mixture was mixed with saturated NaHCO₃ solution (60 ml) and stirred for 15 min. The aqueous phase was extracted with dichloromethane (2×40 ml). The combined organic phases were concentrated to low volume after drying, and a light brown oil was obtained. The chromatographic separation of the substance mixture on silica gel 60 (150 g) was conducted with ethyl acetate/methanol (1:1).

Yield (non-polar diastereomer): 821 mg (41%), beige-coloured solid

Yield (polar diastereomer): 377 mg (19%), beige-coloured solid 2-(4-(dimethylamino)-4-phenylcyclohexylamino)-3-(1H-indol-3-yl)propanamide dihydrochloride (Example 3, non-polar diastereomer)

The non-polar diastereomer from step 1 (870 mg, 2.1 mmol) was dissolved in ethyl methyl ketone (50 ml) and mixed with Me₃SiCl (0.73 ml, 5.3 mmol). The precipitated solid was aspirated after 1 h.

Yield: 900 mg (93%), white crystalline solid
Melting point: 227-233° C.
13C NMR (101 MHz, DMSO-D6) δ ppm: 22.1, 23.8, 24.9, 26.2, 38.1, 51.2, 58.0, 67.7, 107.3, 111.3, 118.4, 118.5, 120.9, 124.2, 127.2, 128.8, 129.5, 132.6, 135.9, 169.0

2-(4-(dimethylamino)-4-phenylcyclohexylamino)-3-(1H-indol-3-yl)propanamide; dihydrochloride (Example 4, polar diastereomer)

Me₃SiCl (0.3 ml, 2.2 mmol) was added to a solution of the more polar diastereomer from step 1 (360 mg, 0.89 mmol) in ethyl methyl ketone (250 ml). The precipitated solid was aspirated after a reaction time of 1 h.

Yield: 444 mg (100%) Melting point: 201-210° C.
13C NMR (101 MHz, DMSO-D6) δ ppm: 24.0, 25.4, 26.2, 28.2, 28.3, 37.2, 54.3, 57.6, 67.6, 107.0, 111.3, 118.3, 118.4, 120.9, 124.3, 127.1, 129.1, 129.6, 129.7, 135.9, 169.1

Example 5 and Example 6

Step 1

(S)-benzyl 1-(dimethylamino)-3-(1H-indol-3-yl)-1-oxopropan-2-yl carbamate (S)-2,5-dioxopyrrolidin-1-yl 2-(benzyloxycarbonylamino)-3-(1H-indol-3-yl)propanoate (2 g, 4.6 mmol) was dissolved in tetrahydrofuran (60 ml) in argon. Dimethylamine (2M in THF, 4.6 ml, 9.2 mmol) was added to the clear solution. A white precipitate separated out immediately after the addition. The reaction mixture was stirred for 24 h at room temperature. For work up the batch was adjusted to pH 1 with 2N HCl. The aqueous mixture was extracted with ethyl acetate (3×40 ml). The combined organic phases were washed with saturated sodium hydrogencarbonate solution (1×40 ml) and after drying with Na₂SO₄ were concentrated to low volume. The raw product was further processed in the next reaction without any further purification. Yield: 1.6 g (95%)

Step 2

(S)-2-amino-3-(1H-indol-3-yl)-N,N-dimethylpropanamide (S)-benzyl 1-(dimethylamino)-3-(1H-indol-3-yl)-1-oxopropan-2-yl carbamate (1.88 g, 5.14 mmol) was mixed in abs. methanol (60 ml) with palladium as catalyst (Pd/C, 5%, 800 mg) and hydrogenated for 2 h at RT (hydrogen pressure: 3 bar). The catalyst was removed via a fritted glass filter provided with a 1 cm high layer of celite. The fritted glass filter was washed thoroughly with methanol (400 ml). The solvent was distilled off in a vacuum.

Yield: 1 g (84%)

Step 3

(S)-2-(4-(dimethylamino)-4-phenylcyclohexylamino)-3-(1H-indol-3-yl)-N,N-dimethylpropanamide (polar and non-polar diastereomer)

4-(dimethylamino)-4-phenylcyclohexanone (1.1 g, 5.41 mmol) was dissolved in a mixture of 1,2-dichloroethane (30 ml) and tetrahydrofuran (40 ml) in argon, mixed with (S)-2-amino-3-(1H-indol-3-yl)-N,N-dimethylpropanamide (1 g, 4.3 mmol), acetic acid (0.31 ml, 5.41 mmol) and $Na_2SO_4$ (2.7 g). The mixture was stirred for 15 min at RT and then mixed with sodium triacetoxyboron hydride (1.65 g, 7.57 mmol) and stirred for 48 hours. For work up of the batch the mixture was mixed with saturated $NaHCO_3$ solution (60 ml) and stirred for 15 min. The aqueous phase was extracted with dichloromethane (2×40 ml). The combined organic phases were concentrated to low volume after drying and a light brown oil was obtained. The chromatographic separation of the substance mixture on silica gel 60 (100 g) was conducted with ethyl acetate/methanol (1:1).

Yield (non-polar diastereomer): 250 mg (11%), beige-coloured solid

Yield (polar diastereomer): 430 mg (18%), beige-coloured solid

Step 4

(S)-2-(4-(dimethylamino)-4-phenylcyclohexylamino)-3-(1H-indol-3-yl)-N,N-dimethylpropanamide dihydrochloride (Example 5, non-polar diastereomer)

(S)-2-(4-(dimethylamino)-4-phenylcyclohexylamino)-3-(1H-indol-3-yl)-N,N-dimethylpropanamide (240 mg, 0.55 mmol, non-polar diastereomer from step 3) was dissolved in ethyl methyl ketone (10 ml) and mixed with $Me_3SiCl$ (0.18 ml, 1.39 mmol). The white crystalline solid was aspirated after 1 h.

Yield: 160 mg (54%) Melting point: 189-204° C.

13C NMR (101 MHz, DMSO-D6) δ ppm: 22.7, 24.0, 24.8, 25.0, 26.5, 35.4, 36.3, 38.8, 51.5, 55.1, 67.7, 106.6, 111.5, 118.1, 118.5, 121.2, 124.5, 127.0, 128.8, 128.9, 129.4, 132.7, 135.9, 167.6

(S)-2-(4-(dimethylamino)-4-phenylcyclohexylamino)-3-(1H-indol-3-yl)-N,N-dimethylpropanamide dihydrochloride (Example 6, polar diastereomer)

$Me_3SiCl$ (0.3 ml, 2.4 mmol) was added to a solution of (S)-2-(4-(dimethylamino)-4-phenylcyclohexylamino)-3-(1H-indol-3-yl)-N,N-dimethylpropanamide (420 mg, 0.9 mmol, polar diastereomer from step 3) in ethyl methyl ketone (10 ml). The solid was aspirated after a reaction time of 1 h.

Yield: 460 mg (93%)

Melting point: 199-212° C.

13C NMR (101 MHz, DMSO-D6) δ ppm: 24.5, 25.2, 26.6, 28.3, 28.6, 35.3, 36.1, 37.2, 54.4, 54.5, 67.5, 106.3, 111.5, 117.9, 118.5, 121.1, 124.6, 127.0, 129.1, 129.5, 129.6, 135.9, 167.6

Example 7 and Example 8

Step 1

(S)-benzyl 3-(1H-indol-3-yl)-1-(methylamino)-1-oxopropan-2-yl carbamate (S)-2,5-dioxopyrrolidin-1-yl 2-(benzyloxycarbonylamino)-3-(1H-indol-3-yl)propanoate (1.5 g, 3.4 mmol) was dissolved in tetrahydrofuran (10 ml) in argon. Methylamine (2M in THF, 3.4 ml, 6.88 mmol) was added to this clear solution. A white precipitate separated out immediately after the addition. The reaction mixture was stirred for 24 h at room temperature. For work up the batch was adjusted to pH 1 with 2N HCl. The aqueous mixture was extracted with ethyl acetate (3×40 ml). The combined organic phases were washed with saturated sodium hydrogencarbonate solution (1×40 ml) and after drying with $Na_2SO_4$ were concentrated to low volume. The raw product was further processed in the next reaction without any further purification. Yield: 1.19 g (100%)

Step 2

(S)-2-amino-3-(1H-indol-3-yl)-N-methylpropanamide (S)-benzyl 3-(1H-indol-3-yl)-1-(methylamino)-1-oxopropan-2-yl carbamate (187 mg, 0.5 mmol) was mixed in abs. methanol (30 ml) with palladium as catalyst (Pd/C, 5%, 80 mg) and hydrogenated for 2 h at RT (hydrogen pressure: 3 bar). The catalyst was removed via a fritted glass filter provided with a 1 cm high layer of celite. The fritted glass filter was washed thoroughly with methanol (200 ml). The solvent was distilled off in a vacuum.

Yield: 108 mg (99%)

Step 3

(S)-2-(4-(dimethylamino)-4-phenylcyclohexylamino)-3-(1H-indol-3-yl)-N,N-methylpropanamide (polar and non-polar diastereomer)

4-(dimethylamino)-4-phenylcyclohexanone (781 mg, 3.6 mmol) was dissolved in a mixture of 1,2-dichloroethane (20 ml) and tetrahydrofuran (30 ml) in argon, mixed with (S)-2-amino-3-(1H-indol-3-yl)-N,N-methylpropanamide (790 mg, 3.6 mmol), acetic acid (0.2 ml, 3.6 mmol) and $Na_2SO_4$ (1.8 g). The mixture was stirred for 15 min at RT and then mixed with sodium triacetoxyboron hydride (1.1 g, 5.04 mmol). After stirring for 48 hours at RT, no further starting product could be detected by thin-film chromatography. For work up of the batch the mixture was mixed with saturated $NaHCO_3$ solution (60 ml) and stirred for 15 min. The aqueous phase was extracted with dichloromethane (2×40 ml). The combined organic phases were concentrated to low volume after drying and a light brown oil was obtained. The chromatographic separation of the substance mixture on silica gel 60 (100 g) was conducted with ethyl acetate/methanol (1:1).

Yield (non-polar diastereomer): 500 mg (33%), beige-coloured solid

Yield (polar diastereomer): 217 mg (14%), beige-coloured solid

((S)-2-(4-(dimethylamino)-4-phenylcyclohexylamino)-3-(1H-indol-3-yl)-N-methylpropanamide dihydrochloride (Example 7, non-polar diastereomer)

(S)-2-(4-(dimethylamino)-4-phenylcyclohexylamino)-3-(1H-indol-3-yl)-N-methylpropanamide (480 mg, 1.15 mmol, non-polar diastereomer from step 3) was dissolved in ethyl methyl ketone (50 ml) and mixed with Me$_3$SiCl (0.39 ml, 2.8 mmol). The solid was aspirated after 1 h.

Yield: 570 mg (96%), white crystalline
Melting point: 238-240° C.
13C NMR (101 MHz, DMSO-D6) δ ppm: 22.2, 24.0, 24.7, 25.5, 26.1, 38.1, 51.0, 58.6, 67.8, 107.4, 111.4, 118.4, 118.5, 121.0, 124.0, 127.1, 128.9, 129.5, 132.6, 135.9, 167.5

((S)-2-(4-(dimethylamino)-4-phenylcyclohexylamino)-3-(1H-indol-3-yl)-N-methylpropanamide dihydrochloride (Example 8, polar diastereomer)

Me$_3$SiCl (0.17 ml, 1.26 mmol) was added to a solution of (S)-2-(4-(dimethylamino)-4-phenylcyclohexylamino)-3-(1H-indol-3-yl)-N-methylpropanamide (210 mg, 0.5 mmol, polar diastereomer from step 3) in ethyl methyl ketone (20 ml). The solid was aspirated after a reaction time of 1 h.

Yield: 240 mg (97%)
Melting point: 199-212° C.
13C NMR (101 MHz, DMSO-D6) δ ppm: 24.1, 25.3, 25.6, 26.3, 28.2, 28.2, 37.2, 54.1, 57.8, 67.6, 107.0, 111.4, 118.2, 118.4, 120.9, 124.2, 127.0, 129.1, 129.6, 129.8, 135.9, 167.6

Example 9 and Example 10

Step 1

(S)-benzyl 1-hydrazinyl-3-(1H-indol-3-yl)-1-oxopropan-2-yl carbamate

A solution of (S)-2-(benzyloxycarbonylamino)-3-(1H-indol-3-yl)propionic acid (5.00 g, 15 mmol) in anhydrous tetrahydrofuran (100 mL) was mixed with 1,1'-carbonyldiimidazole (2.91 g, 18 mmol) and stirred for 2 h at room temperature. After the gas development had ended a 1M solution of hydrazine in tetrahydrofuran (75 mL, 75 mmol) was added in drops and the mixture stirred for 2 days at room temperature. The separated precipitate was filtered off and dried.

Yield: 1.57 g (30%), white solid
Melting point: 204-208° C.
1H-NMR (DMSO-d6): 2.80 (d, 1H, J=9.4, 14.4 Hz); 3.04 (d, 1H, J=14.7, 4.9 Hz); 4.21 (d, 2H, J=3.0 Hz); 4.23-4.28 (m, 1H); 4.93 (d, 2H, J=1.9 Hz); 6.97 (t, 1H, J=7.4 Hz); 7.06 (dt, 1H, J=7.0, 1.1 Hz); 7.14 (d, 1H, J=2.1 Hz); 7.23-7.37 (m, 6H); 7.40 (d, 1H, J=8.4 Hz); 7.62 (d, 1H, J=7.7 Hz); 9.24 (t, 1H, J=3.3 Hz); 10.79 (s, 1H).
13C-NMR (DMSO-d6): 28.0; 54.1; 65.2; 110.0; 111.2; 118.2; 118.4; 120.8; 123.7; 126.7; 127.2; 127.4; 127.6; 128.2; 136.0; 137.0; 155.6; 171.0.

Step 2

(S)-benzyl 2-(1H-indol-3-yl)-1-(5-oxo-4,5-dihydro-1,3,4-oxadiazol-2-yl)ethyl carbamate A solution of (S)-benzyl 1-hydrazinyl-3-(1H-indol-3-yl)-1-oxopropan-2-yl carbamate (1.57 g, 4.4 mmol) in anhydrous tetrahydrofuran (220 mL) was mixed with 1,1'-carbonyldiimidazole (848 mg, 5.23 mmol) and triethylamine (529 mg, 725 µL, 5.23 mmol) and stirred overnight at room temperature. The reaction mixture was then concentrated to low volume in a vacuum and the residue (3.20 g) purified by flash chromatography (200 g, 20×5.7 cm) with chloroform/methanol (95:5).

Yield: 1.41 g (85%), white solid
Melting point: 82-87° C.
1H-NMR (DMSO-d6): 3.12 (dd, 1H, J=14.5, 8.4 Hz); 3.22 (dd, 1H, J=14.6, 6.9 Hz); 4.73 (q, 1H, J=8.1 Hz); 5.00 (s, 2H); 6.96 (t, 1H, J=7.4 Hz); 7.08 (dt, 1H, J=7.1, 0.9 Hz); 7.14 (d, 1H, J=2.3 Hz); 7.23-7.37 (m, 6H); 7.51 (d, 1H, J=7.8 Hz); 8.03 (d, 1H, J=8.0 Hz); 10.85 (s, 1H); 12.16 (brs, 1H).
13C-NMR (DMSO-d6): 27.1; 48.9; 65.5; 109.0; 111.4; 117.9; 118.4; 120.9; 123.8; 127.0; 127.6; 127.7; 128.3; 136.0; 136.7; 154.7; 155.6; 156.4.

Step 3

(S)-5-(1-amino-2-(1H-indol-3-yl)ethyl)-1,3,4-oxadiazol-2(3H)-one

A solution of (S)-benzyl 2-(1H-indol-3-yl)-1-(5-oxo-4,5-dihydro-1,3,4-oxadiazol-2-yl)ethyl-carbamate (1.41 g, 3.73 mmol) in anhydrous tetrahydrofuran (100 mL) was mixed with 10% palladium on activated carbon (160 mg) and hydrogenated for 24 h at room temperature and at 3 bar. A further portion of 20% palladium on activated carbon (160 mg) was added and the mixture hydrogenated for a further 24 h at 3 bar and 40° C. The catalyst was then filtered off, the filtrate concentrated to low volume in a vacuum and the residue (1.24 g) purified by flash chromatography (100 g, 20×4.0 cm) with chloroform/methanol (95:5).

Yield: 536 mg (59%), white solid
Melting point: 79-85° C.
1H-NMR (DMSO-d6): 3.01 (dd, 1H, J=14.3, 6.6 Hz); 3.09 (dd, 1H, J=14.2, 7.5 Hz); 3.96 (t, 1H, J=7.0 Hz); 6.96 (dt, 1H, J=7.0, 1.0 Hz); 7.05 (dt, 1H, J=8.1, 1.0 Hz); 7.11 (d, 1H, J=2.3 Hz); 7.32 (d, 1H, J=8.0 Hz); 7.47 (d, 1H, J=7.8 Hz); 10.85 (s, 1H). 13C-NMR (DMSO-d6): 30.4; 49.5; 109.6; 111.4; 117.9; 118.3; 120.8; 123.6; 127.2; 136.0; 155.0; 159.6.

5-((S)-1-(4-(dimethylamino)-4-phenylcyclohexylamino)-2-(1H-indol-3-yl)ethyl)-1,3,4-oxadiazol-2(3H)-one hydrochloride (1:1) (Example 9, non-polar diastereomer) and 5-((S)-1-(4-(dimethylamino)-4-phenylcyclohexylamino)-2-(1H-indol-3-yl)ethyl)-1,3,4-oxadiazol-2(3H)-one (Example 10, polar diastereomer)

A solution of (S)-5-(1-amino-2-(1H-indol-3-yl)ethyl)-1,3,4-oxadiazol-2(3H)-one (485 mg, 1.98 mmol) and 4-dimethylamino-4-phenyl cyclohexanone (430 mg, 1.98 mmol) in anhydrous tetrahydrofuran (40 mL) was mixed with sodium sulphate (1.00 g) and stirred for 2 h at room temperature. After adding acetic acid (297 mg, 283 µL, 4.95 mmol) sodium triacetoxyboron hydride (633 mg, 2.97 mmol) was added and the mixture was stirred overnight at room temperature. The solvent was then removed in a vacuum, the residue mixed with 1 M potassium carbonate solution (50 mL) and extracted with ethyl acetate (3×50 mL). The organic phase was dried with sodium sulphate and concentrated to low volume in a vacuum. The raw product (780 mg) was purified by flash chromatography (38 g, 20×2.5 cm) with ethyl acetate/methanol (9:1) and 1% triethylamine.

Yield (Example 10, polar diastereomer): 158 mg (18%), white solid

Melting point: 115-121° C.

1H-NMR (DMSO-d6): 1.45-1.70 (m, 3H); 1.75-1.90 (m, 2H); 1.90 (s, 6H); 2.40-2.48 (m, 3H); 2.50-2.56 (m, 2H); 2.98-3.03 (m, 2H); 3.84 (t, 1H, J=7.3 Hz); 6.91-6.96 (m, 1H); 7.01-7.06 (m, 2H); 7.24 (t, 1H, J=7.1 Hz); 7.27-7.41 (m, 6H); 10.8 (s, 1H).

13C-NMR (DMSO-d6): 28.1; 28.9; 29.4; 30.5; 30.7; 38.0; 53.6; 54.8; 60.7; 109.5; 111.4; 117.7; 118.3; 120.8; 123.4; 126.1; 127.0; 127.5; 127.7; 136.0; 136.9; 154.9; 158.1.

$[\alpha]D24=-7.1$ (c 1.0, MeOH)

The fraction with the non-polar diastereomer was purified once again with chloroform/methanol (5:1). The hydrochloride was obtained.

Yield (Example 9, non-polar diastereomer): 426 mg (45%), white solid

Melting point: 152-161° C.

1H-NMR (DMSO-d6): 1.50-2.00 (m, 5H); 2.10-2.45 (br s, 10H); 2.50-2.70 (br s, 1H); 3.05-3.20 (m, 2H); 3.88 (br s, 1H); 6.95-7.02 (m, 1H); 7.03-7.10 (m, 1H); 7.17 (br s, 1H); 7.31-7.36 (m, 1H); 7.50 (br d, 4H, J=7.7 Hz); 7.63 (br s, 2H); 9.80-10.20 (br s, 1H); 10.89 (s, 1H); 12.00 (s, 1H).

13C-NMR (DMSO-d6): 25.4; 27.7; 28.8; 37.1; 47.8; 53.4; 54.8; 109.5; 117.8; 118.4; 120.8; 123.7; 128.5 (very wide); 136.0; 154.8; 157.8.

$[\alpha]D24=-12.3$ (c 1.0, MeOH);

Example 11

Step 1

N'-hydroxyacetimidamide

A solution of 50% hydroxylamine in water (3.7 mL, 56 mmol) was mixed with acetonitrile (30 mL) and stirred for 24 h at 90° C. The reaction solution was then cooled to 4° C. and the product was crystallised out, filtered off and dried in a vacuum.

Yield: 2.66 g (64%), white needles

Melting point: 137° C.

1H-NMR (400 MHz, CDCl3): 1.83 (s, 3H), 4.53 (br s, 3H).

13C-NMR (100 MHz, CDCl3): 16.9; 151.1.

Step 2

(S)-tert-butyl 1-(1-aminoethylidene-aminooxy)-3-(1H-indol-3-yl)-1-oxopropan-2-yl carbamate A solution of N'-hydroxyacetimidamide (500 mg, 6.74 mmol) and (S)-2-(tert-butoxycarbonylamino)-3-(1H-indol-3-yl)propionic acid (1.7 g, 5.6 mmol) in dichloromethane/N,N-dimethylformamide (30 mL, 9:1) was mixed with 1-hydroxybenzotriazole hydrate (910 mg, 6.74 mmol) and 1,3-dicyclohexylcarbodiimide (1.39 g, 6.74 mmol) at −10° C. and stirred for 20 min at this temperature. The mixture was then stirred for 2 h at room temperature. The reaction mixture was concentrated to low volume in a vacuum and the residue taken up in ethyl acetate. The organic phase was washed with sodium hydrogencarbonate solution (2×30 mL), water (30 mL) and ammonium chloride solution (2×30 mL) and dried with magnesium sulphate.

Yield: 849 mg (42%), colourless solid

Melting point: 75-78° C.

1H-NMR (300 MHz, DMSO-d6): 1.33 (s, 9H), 1.76 (s, 3H), 2.98 (dd, J=14.5, 9.1 Hz, 1H), 3.15 (dd, J=14.5, 5.4 Hz, 1H), 4.38 (dt, J=8.9, 5.4 Hz, 1H), 6.36 (br s, 2H), 6.98 (t, J=6.9 Hz, 1H), 7.06 (t, J=6.9 Hz, 1H), 7.13 (d, J=2.2 Hz, 1H), 7.24 (d, J=8.3 Hz, 1H), 7.33 (d, J=7.9 Hz, 1H), 7.58 (d, J=7.8 Hz, 1H), 10.84 (s, 1H).

13C-NMR (100 MHz, DMSO-d6): 16.4; 27.7; 28.7; 54.6; 79.5; 110.2; 112.0; 118.9; 119.3; 121.8; 124.1; 127.6; 136.5; 156.3; 157.6; 170.5.

Step 3

(S)-tert-butyl 2-(1H-indol-yl)-1-(3-methyl-1,2,4-oxadiazol-5-yl)ethyl carbamate

A solution of (S)-tert-butyl 1-(1-aminoethylidene-aminooxy)-3-(1H-indol-3-yl)-1-oxopropan-2-yl carbamate (1.37 g, 4.0 mmol) in acetonitrile (40 mL) was mixed with molecular sieve 4 Å (500 mg) and stirred for 16 h at 120° C. in a Teflon pressure vessel. The molecular sieve was then filtered off and the filtrate concentrated to low volume in a vacuum. The residue was purified by flash chromatography (200 g, 20×3.6 cm) with chloroform/methanol/triethylamine (10:0.2:0.01).

Yield: 879 mg (63%), colourless solid

Melting point: 45° C.

1H-NMR (300 MHz, DMSO-d6): 1.33 (s, 9H), 2.31 (s, 3H), 3.22 (dd, J=14.6, 8.4 Hz, 1H), 3.27 (dd, J=15.0, 6.7 Hz, 1H), 4.99 (q, J=7.7 Hz, 1H), 6.98 (t, J=6.8 Hz, 1H), 7.07 (t, J=6.9 Hz, 1H), 7.12 (d, J=2.1 Hz, 1H), 7.33 (d, J=7.9 Hz, 1H), 7.49 (d, J=7.7 Hz, 1H), 7.74 (d, J=7.9 Hz, 1H), 10.87 (s, 1H).

Step 4

(S)-2-(1H-indol-3-yl)-1-(3-methyl-1,2,4-oxadiazol-5-yl)ethanamine

A solution of (S)-tert-butyl 2-(1H-indol-3-yl)-1-(3-methyl-1,2,4-oxadiazol-5-yl)ethyl carbamate (879 mg, 2.6 mmol) in dichloromethane (6 mL) was mixed with trifluoroacetic acid (3 mL) and stirred for 30 min at room temperature. The reaction mixture was then concentrated to low volume in a vacuum, as a result of which the title compound was obtained as trifluoroacetate.

Yield: 940 mg (100%), brown oil

1H-NMR (300 MHz, DMSO-d6): 2.30 (s, 3H), 3.40 (dd, J=14.6, 8.4 Hz, 1H), 3.47 (dd, J=15.1, 5.8 Hz, 1H), 5.06 (dd, J=8.3, 5.8 Hz, 1H), 6.98 (t, J=6.9 Hz, 1H), 7.09 (t, J=7.0 Hz, 1H), 7.13 (dd, J=5.4, 3.0 Hz, 1H), 7.36 (d, J=8.0 Hz, 1H), 7.41 (d, J=7.8 Hz, 1H), 9.01 (s, 3H), 11.05 (s, 1H).

To release the base the trifluoroacetate was dissolved in dichloromethane (30 mL) and washed with a saturated potassium carbonate solution (3×20 mL). The organic phases was dried with sodium sulphate and concentrated to low volume in a vacuum.

Yield: 640 mg (100%)

N4-((S)-2-(1H-indol-3-yl)-1-(3-methyl-1,2,4-oxadiazol-5-yl)ethyl)-N1,N1-dimethyl-1-phenylcyclohexane-1,4-diamine (Example 11, diastereomer mixture)

A solution of (S)-2-(1H-indol-3-yl)-1-(3-methyl-1,2,4-oxadiazol-5-yl)ethanamine (180 mg, 0.74 mmol) and 4-dimethylamino-4-phenylcyclohexanone (161 mg, 0.74 mmol) in anhydrous tetrahydrofuran (20 mL) was mixed with sodium sulphate (500 mg) and stirred for 2 h at room temperature. After adding acetic acid (111 mg, 1.85 mmol) sodium triacetoxyboron hydride (235 mg, 1.11 mmol) was added and the reaction mixture stirred for 72 h at room temperature. The solvent was removed in a vacuum, the residue mixed with 1M potassium carbonate solution (50 mL) and extracted with ethyl acetate (3×50 mL). The combined organic phases were dried with sodium sulphate and concentrated to low volume in a vacuum. The raw product was purified by flash chromatography (80 g, 20×1.6 cm) with chloroform/methanol/triethylamine (10:0.2:0.1→10:0.5:0.1). Since the product was formed as hydrochloride, the residue was dissolved in ethyl acetate (30 mL) and washed with saturated potassium carbonate solution (40 mL). The aqueous phase was extracted with ethyl acetate (3×40 mL) and the combined organic phases were dried with sodium sulphate.

Yield (diastereomer mixture, approx. 2:1): 195 mg (59%), colourless solid

Melting point: 47-52° C.

1H-NMR (400 MHz, DMSO-d6): 1.29-1.64 (m, 9H), 1.87 (s, 2H), 1.88 (s, 4H), 2.24 (s, 1H), 2.25 (s, 2H), 2.35 (d, J=8.4 Hz, 0.33H), 2.42 (d, J=12.4 Hz, 0.67H), 3.12 (d, J=7.4 Hz, 0.67H), 3.22 (d, J=6.2 Hz, 1.33H), 4.27 (q, J=7.5 Hz, 0.33H), 4.38 (q, J=7.5 Hz, 0.67H), 6.92 (t, J=6.9 Hz, 0.33H), 6.94-6.99 (m, 0.67H), 6.99-7.03 (m, 0.33H), 7.04-7.08 (m, 1H), 7.13-7.25 (m, 3H), 7.25-7.39 (m, 3.33H), 7.43 (d, J=7.85 Hz, 1.33H), 10.77 (s, 0.33H), 10.83 (s, 0.67H).

13C-NMR (100 MHz, DMSO-d6): 11.1; 24.4; 25.3; 26.8; 28.0; 28.3; 29.4; 30.2Ä; 30.4; 30.5; 30.7; 37.4; 38.0; 53.0; 53.2; 53.3; 53.8; 58.6; 60.7; 109.3; 109.4; 111.3; 111.4; 117.8; 117.9; 118.3; 118.3; 120.8; 120.9; 123.4; 123.5; 126.1; 126.7; 126.9; 127.0; 127.0; 127.2; 127.5; 127.6; 128.1; 128.8; 135.9; 136.0; 138.7; 166.3; 181.3; 181.4.

Example 12 and Example 13

Step 1

(R)-benzyl 1-hydrazinyl-3-(1H-indol-3-yl)-1-oxopropan-2-yl carbamate

A solution of (R)-2-(benzyloxycarbonylamino)-3-(1H-indol-3-yl)propionic acid (6.76 g, 20 mmol) in anhydrous tetrahydrofuran (100 mL) was mixed with 1,1'-carbonyldiimidazole (3.89 g, 24 mmol) and stirred for 2 h at room temperature. After gas development had ended a 1M solution of hydrazine in tetrahydrofuran (100 mL, 100 mmol) was added in drops and stirred for 18 h at room temperature. The separated precipitate was filtered off.

Yield: 2.42 g (34%), white solid

Melting point: 205-210° C.

1H-NMR (DMSO-d6): 2.91 (dd, 1H, J=14.2, 9.2 Hz); 3.04 (dd, 1H, J=14.4, 5.5 Hz); 4.20-4.27 (m, 1H); 4.93 (d, 1H, J=3.1 Hz); 6.97 (t, 2H, J=7.6 Hz); 7.05 (t, 1H, J=7.1 Hz); 7.14 (d, 1H, J=2.1 Hz); 7.24-7.40 (m, 6H); 7.61 (d, 1H, J=7.6 Hz); 9.22 (s, 1H); 10.79 (s, 1H). 3H with a wide signal of 3.5-5.0 ppm.

Step 2

(R)-benzyl 2-(1H-indol-3-yl)-1-(5-oxo-4,5-dihydro-1,3,4-oxadiazol-2-yl)ethyl carbamate A solution of (R)-benzyl 1-hydrazinyl-3-(1H-indol-3-yl)-1-oxopropan-2-yl carbamate (2.42 g 6.86 mmol) in anhydrous tetrahydrofuran (100 mL) was mixed with 1,1'-carbonyldiimidazole (1.31 g, 8.08 mmol) and triethylamine (817 mg, 1.12 mL, 8.08 mmol) and stirred for 2 days at room temperature. The reaction mixture was then concentrated to low volume in a vacuum and the residue (4.50 g) purified by flash chromatography (100 g, 20×4.0 cm) with chloroform/methanol (9:1).

Yield: 2.30 g (88%), white solid

Melting point: 81-88° C.

1H-NMR (DMSO-d6): 3.13 (dd, 1H, J=14.5, 8.3 Hz); 3.23 (dd, 1H, J=14.5, 6.9 Hz); 4.73 (q, 1H, J=8.2 Hz); 5.00 (s, 2H); 6.98 (t, 1H, J=7.6 Hz); 7.07 (dt, 1H, J=7.5, 1.0 Hz); 7.15 (d, 1H, J=2.2 Hz); 7.25-7.40 (m, 6H); 7.52 (d, 1H, J=7.8 Hz); 8.05 (d, 1H, J=7.8 Hz); 10.88 (s, 1H); 12.18 (br s, 1H).

13C-NMR (DMSO-d6): 27.1; 48.9; 65.5; 109.0; 111.4; 117.9; 118.4; 120.9; 123.8; 127.0; 127.6; 127.7; 128.3; 136.0; 136.7; 154.7; 155.5; 156.4.

Step 3

(R)-5-(1-amino-2-(1H-indol-3-yl)ethyl)-1,3,4-oxadiazol-2(3H)-one

A solution of (R)-Benzyl 2-(1H-indol-3-yl)-1-(5-oxo-4,5-dihydro-1,3,4-oxadiazol-2-yl)ethyl carbamate (2.00 g, 5.3 mmol) in anhydrous tetrahydrofuran (100 mL) was mixed with 20% palladium hydroxide on activated carbon (230 mg) and hydrogenated for 5 h at 40° C. and 3 bar. Catalyst (200 mg) was once again added and the mixture hydrogenated for a further 18 h at 40° C. and 6 bar. Methanol (50 mL) was then added and the mixture hydrogenated for a further 24 h at 40° C. and 6 bar. The catalyst was filtered off, the filtrate concentrated to low volume in a vacuum and the residue (1.43 g) purified by flash chromatography (100 g, 20×4.0 cm) with chloroform/methanol (9:1).

Yield: 684 mg (53%), yellowish solid

Melting point: 66-80° C.

1H-NMR (DMSO-d6): 3.01 (dd, 1H, J=14.5, 6.5 Hz); 3.09 (dd, 1H, J=14.3, 7.4 Hz); 3.97 (t, 1H, J=7.0 Hz); 6.96 (ddd, 1H, J=8.0, 7.0, 1.0 Hz); 7.06 (ddd, 1H, J=8.1, 7.0, 1.2 Hz); 7.12 (d, 1H, J=2.4 Hz); 7.33 (td, 1H, J=8.1, 0.9 Hz); 7.47 (d, 1H, J=8.0 Hz); 10.84 (s, 1H).

Three exchangeable protons could not be identified.

13C-NMR (DMSO-d6): 30.4; 49.5; 109.6; 111.4; 118.0; 118.3; 120.8; 123.6; 127.2; 136.0; 155.0; 159.6.

5-((R)-1-(4-(dimethylamino)-4-phenylcyclohexylamino)-2-(1H-indol-3-yl)ethyl)-1,3,4-oxadiazol-2(3H)-one (Example 12, non-polar diastereomer) and (Example 13, polar diastereomer)

A solution of (R)-5-(1-amino-2-(1H-indol-3-yl)ethyl)-1,3,4-oxadiazol-2(3H)-one (673 mg, 2.75 mmol) and 4-dimethylamino-4-phenyl-cyclohexanone (597 mg, 2.75 mmol) in anhydrous tetrahydrofuran (100 mL) was mixed with sodium sulphate (1.00 g) and stirred for 4 h at room temperature. After adding acetic acid (412 mg, 393 µL, 6.87 mmol) sodium triacetoxyboron hydride (878 mg, 4.12 mmol) was added and the mixture stirred for 2 days at room temperature. The solvent was then concentrated to low volume in a vacuum, the residue mixed with 1M potassium carbonate solution (50 mL) and extracted with ethyl acetate (3×30 mL). The organic phase was dried with sodium sulphate and concentrated to low volume in a vacuum. The raw product (1.15 g) was purified by flash chromatography (IOg, 20×4.0 cm) with ethyl acetate/methanol (9:1) and 1% triethylamine.

The more non-polar product (635 mg) obtained was purified once again by flash chromatography (38 g, 20×2.5 cm) with chloroform/methanol (5:1). The isolated substance (571 mg) was taken up in 1 M potassium carbonate solution (20 mL) and extracted with ethyl acetate (6×10 mL). The combined organic phases were dried with sodium sulphate and concentrated to low volume in a vacuum.

Yield (Example 12, non-polar diastereomer): 423 mg (35%), white foam

Melting point: 110-113° C.

1H-NMR (DMSO-d6): 1.30-1.65 (m, 6H); 1.89 (s, 6H); 2.11 (br s, 1H); 2.38-2.48 (m, 2H); 3.07-3.12 (m, 2H); 3.94 (br s, 1H); 6.97 (dd, 1H, J=7.9, 7.1, 1.1 Hz); 7.02-7.09 (m, 1H); 7.12 (d, 1H, J=2.3 Hz); 7.18-7.36 (m, 6H); 7.47 (s, 1H, J=7.8 Hz); 10.85 (s, 1H); 11.90 (br s, 1H). 13C-NMR (DMSO-d6): 20.7; 26.8; 28.3; 29.1; 30.1; 31.1; 53.4; 109.6; 111.4; 117.8; 118.4; 120.9; 123.6; 126.9; 127.1; 127.3; 136.0; 154.9; 158.2.

[α]D24=+9.5 (c 1.0, MeOH)

The more polar product (183 mg (15%)) obtained was taken up in 1M potassium carbonate solution (10 mL) and the aqueous phase extracted with ethyl acetate (6×5 mL). The combined organic phases were dried with sodium sulphate and concentrated to low volume in a vacuum.

Yield (Example 13, polar diastereomer): 98 mg (8%), white solid

Melting point: 90-105° C.

1H-NMR (DMSO-d6): 0.80-1.00 (m, 2H); 1.40-1.82 (m, 6H); 1.88 (s, 6H); 2.40-2.47 (m, 2H); 2.98 (d, 2H, J=7.3 Hz); 3.82 (br s, 1H); 6.93 (ddd, 1H, J=7.9, 7.1, 1.0 Hz); 6.95-7.06 (m, 2H); 7.21-7.41 (m, 7H); 10.78 (s, 1H, ); 11.95 (br s, 1H). 13C-NMR (DMSO-d6): 20.7; 28.1; 28.9; 29.4; 30.5; 37.9; 53.5; 109.5; 111.4; 117.7; 118.3; 120.8; 123.4; 126.5; 127.0; 127.7; 127.9; 136.0; 154.9; 158.1.

[α]D24=+4.4 (c 1.0, MeOH)

Example 14 and Example 15

Step 1

(R)-tert-butyl 1-(1-aminoethylidene-aminooxy)-3-(1H-indol-3-yl)-1-oxopropan-2-yl carbamate N'-hydroxyacetimidamide (400 mg, 5.39 mmol, for production cf. step 1 from Ex. 11) and (R)-2-(tert-butoxycarbonylamino)-3-(1H-indol-3-yl)propionic acid (1.36 g, 4.48 mmol) were converted in the same manner as in Example 11 (step 2).

Yield: 1.91 g (98%)

Melting point: 70-75° C.

1H-NMR (300 MHz, DMSO-d6): 1.33 (s, 9H), 1.76 (s, 3H), 2.99 (dd, J=14.2, 9.1 Hz, 1H), 3.16 (dd, J=14.5, 5.1 Hz, 1H), 4.38 (dt, J=8.7, 5.3 Hz, 1H), 6.37 (br s, 2H), 6.98 (t, J=6.9 Hz, 1H), 7.07 (t, J=6.9 Hz, 1H), 7.14 (d, J=2.2 Hz, 1H), 7.24 (d, J=8.4 Hz, 1H), 7.33 (d, J=7.9 Hz, 1H), 7.58 (d, J=7.7 Hz, 1H), 10.84 (s, 1H).

Step 2

(R)-tert-butyl 2-(1H-indol-3-yl)-1-(3-methyl-1,2,4-oxadiazol-5-yl)ethyl carbamate A solution of (R)-tert-butyl 1-(1-aminoethylidene-aminooxy)-3-(1H-indol-3-yl)-1-oxopropan-2-yl carbamate (1.91 g, 5.3 mmol) in acetonitrile (40 mL) was mixed with molecular sieve 4 Å (1 g) and stirred for 48 h at 120° C. in a Teflon pressure vessel. The molecular sieve was then filtered off and the filtrate concentrated to low volume in a vacuum. The residue was purified by flash chromatography (200 g, 20×3.6 cm) with chloroform/methanol/triethylamine (10:0.2:0.01).

Yield: 1.81 g (100%)

Step 3

(R)-2-(1H-indol-3-yl)-1-(3-methyl-1,2,4-oxadiazol-5-yl)ethanamine

A solution of (R)-tert-butyl 2-(1H-indol-3-yl)-1-(3-methyl-1,2,4-oxadiazol-5-yl)ethyl carbamate in dichloromethane (10 mL) was mixed with trifluoroacetic acid (6 mL) and stirred for 5 h at room temperature. The reaction mixture was then concentrated to low volume in a vacuum. The residue was dissolved in dichloromethane (30 mL) and washed with saturated potassium carbonate solution (3×20 mL). The organic phase was dried with sodium sulphate and concentrated to low volume in a vacuum. The residue was purified by flash chromatography (200 g, 20×3.6 cm) with chloroform/methanol/triethylamine (10:0.2:0.1).

Yield: 727 mg (100%), brownish oil

1H-NMR (300 MHz, DMSO-d6: 2.27 (s, 5H), 3.13 (dd, J=14.3, 6.6 Hz, 1H), 3.21 (dd, J=14.2, 7.2 Hz, 1H), 4.36 (t, J=6.8 Hz, 1H), 6.95 (t, J=6.9 Hz, 1H), 7.05 (t, J=6.9 Hz, 2H), 7.31 (d, J=8.0 Hz, 1H), 7.44 (d, J=7.6 Hz, 1H), 10.84 (s, 1H).

N4-((R)-2-(1H-indol-3-yl)-1-(3-methyl-1,2,4-oxadiazol-5-yl)ethyl)-N1,N1-dimethyl-1-phenylcyclohexane-1,4-diamine (Example 14, non-polar diastereomer) and (Example 15, polar diastereomer)

A solution of (R)-2-(1H-Indol-3-yl)-1-(3-methyl-1,2,4-oxadiazol-5-yl)ethanamine (400 mg, 1.65 mmol) and 4-dimethylamino-4-phenylcyclohexanone (358.7 g, 1.65 mmol) in anhydrous tetrahydrofuran (50 mL) was mixed with sodium sulphate (1.1 g) and stirred for 2 h at room temperature. After adding acetic acid (248 mg, 4.1 mmol) sodium triacetoxyboron hydride (524 mg, 2.47 mmol) was added and the reaction mixture stirred for 16 h at room temperature. The solvent was removed in a vacuum, the residue mixed with 1M potassium carbonate solution (50 mL) and extracted with ethyl acetate (3×50 mL). The combined organic phases were dried with sodium sulphate and concentrated to low volume in a vacuum. The raw product was purified by flash chromatography (400 g, 20×5.6 cm) with ethyl acetate/isopropanol/triethylamine (10:0.3:0.01→5:1:0.1).

Yield (Example 14, non-polar diastereomer): 315 mg (43%), colourless solid

Melting point: 52-54° C.

1H-NMR (400 MHz, DMSO-d6): 1.39 (t, J=14.5 Hz, 2H), 1.48 (t, J=11.0, 2H), 1.58 (d, J=12.0 Hz, 2H), 1.89 (s, 6H), 2.25 (s, 3H), 2.36 (dd, J=9.2, 5.0 Hz, 2H), 2.42 (d, J=13.0 Hz, 2H), 3.22 (d, J=6.6 Hz, 2H), 4.38 (t, J=7.0 Hz, 1H), 6.97 (ddd, J=7.9, 7.0, 1.0, Hz, 1H), 7.05 (ddd, J=8.2, 7.2, 1.1 Hz, 2H), 7.21 (t, J=6.9 Hz, 1H), 7.25-7.34 (m, 5H), 7.44 (d, J=7.9 Hz, 1H), 10.81 (s, 1H).

13C-NMR (100 MHz, DMSO-d6): 11.0; 26.8; 28.3; 30.4; 37.4; 53.1; 53.2; 58.6; 109.4; 111.3; 117.8; 118.3; 120.8; 123.5; 126.1; 126.6; 127.1; 0; 127.2; 136.0; 138.8; 166.0; 181.4.

Yield (Example 15, polar diastereomer): 98 mg (13%), colourless solid

Melting point: 62-64° C.

1H-NMR (300 MHz, DMSO-d6): 0.90 (q, J=9.8 Hz, 3H), 1.53 (m, 3H), 1.80 (d, J=13.1 Hz, 2H), 1.92 (s, 6H), 2.24 (s, 3H), 2.32-2.47 (m, 2H), 3.12 (d, J=7.2 Hz, 2H), 4.27 (t, J=7.0 Hz, 1H), 6.92 (td, J=6.8, 4.1 Hz, 2H), 7.02 (t, J=6.9 Hz, 1H), 7.22-7.43 (m, 7H), 10.77 (s, 1H).

13C-NMR (100 MHz, DMSO-d6): 11.0; 28.0; 29.3; 30.2; 30.4; 30.5; 37.9; 53.2; 53.7; 54.8; 109.3; 111.3; 117.8; 118.3; 120.8; 123.4; 126.3; 126.9; 127.4; 127.6; 127.8; 135.9; 166.3; 181.3.

Example 16 and Example 17

Step 1

(S)-tert-butyl 2-(1H-indol-3-yl)-3-oxo-3-(prop-2-ynylamino)propyl carbamate

A solution of (S)-3-(tert-butoxycarbonylamino)-2-(1H-indol-3-yl)propionic acid (1.0 g, 3.3 mmol) in THF (7 mL) was mixed in portions with carbonyldiimidazole (535 mg, 3.3 mmol) at room temperature and stirred for 2 h at room temperature before propargylamine (270 mg, 5.0 mmol) was added in drops. After 1 h at room temperature, the mixture was diluted with diethyl ether (80 mL), washed with saturated sodium hydrogencarbonate solution (2×20 mL) and dried with sodium sulphate. The solvent was removed in a vacuum and the residue recrystallised from diethyl ether.

Yield: 890 mg (79%), white solid

1H-NMR (CDCl3): 1.42 (9H, s); 2.14 (1H, t, J=2.4 Hz); 3.15-3.33 (2H, m); 3.93 (2H, br s); 4.43 (1H, br s); 5.10 (1H, br s); 6.00 (1H, br s); 7.06 (1H, d, J=2 Hz); 7.14 (1H, m); 7.21 (1H, m); 7.37 (1H, d, J=8 Hz); 7.65 (1H, d, J=8 Hz); 8.10 (1H, br s).

Step 2

(S)-tert-butyl 2-(1H-indol-3-yl)-2-(5-methyloxazol-2-yl)ethyl carbamate

A solution of gold(III) chloride (45 mg, 0.15 mmol) in acetonitrile (2 mL) was mixed with a solution of (S)-tert-butyl 2-(1H-indol-3-yl)-3-oxo-3-(prop-2-ynylamino)propyl carbamate (512 mg, 1.5 mmol) in acetonitrile (6 mL) at room temperature and stirred for 18 h at 50° C. The solvent was removed in a vacuum and the residue was purified by flash chromatography (20 g, 16×2.5 cm) with ethyl acetate/cyclohexane (1:1).

Yield: 330 mg (64%)

1H-NMR (CDCl3): 1.41 (9H, s); 2.23 (3H, s); 3.38 (2H, m); 5.20 (2H, br s); 6.61 (1H, s); 6.90 (1H, s); 7.07 (1H, t, J=7.6 Hz); 7.16 (1H, t, J=7.6 Hz); 7.32 (1H, d, J=8 Hz); 7.43 (1H, d, J=8 Hz); 8.06 (1H, br s).

Step 3

(S)-2-(1H-indol-3-yl)-2-(5-methyloxazol-2-yl)ethanamine

A solution of (S)-tert-butyl 2-(1H-indol-3-yl)-2-(5-methyloxazol-2-yl)ethyl carbamate (320 mg, 0.93 mmol) in dichloromethane (10 mL) was mixed in drops with trifluoroacetic acid (1.5 mL, 20 mmol) at 0° C. and stirred for 3 h at room temperature. The mixture was then diluted with dichloromethane (80 mL), washed with saturated sodium hydrogencarbonate solution (30 mL), dried with sodium sulphate and the solvent removed in a vacuum.

Yield: 220 mg (98%), brown oil

1H-NMR (CDCl3): 2.09 (2H, br s); 2.29 (3H, s); 3.18 (1H, dd, J=14.4 and 8.4 Hz); 3.42 (1H, dd, J=14.4 and 5 Hz); 4.38 (1H, m); 6.61 (1H, s); 7.05 (1H, s); 7.10 (1H, m); 7.19 (1H, m); 7.35 (1H, d, J=8 Hz); 7.55 (1H, d, J=8 Hz); 8.09 (1H, br s).

N4-((S)-2-(1H-indol-3-yl)-1-(5-methyloxazol-2-yl)ethyl)-N1,N1-dimethyl-1-phenylcyclohexane-1,4-diamine (Example 16, non-polar diastereomer) and (Example 17, polar diastereomer)

A solution of (S)-2-(1H-Indol-3-yl)-2-(5-methyloxazol-2-yl)ethanamine (220 mg, 0.91 mmol) and 4-dimethylamino-4-phenylcyclohexanone (218 mg, 1.0 mmol) in 1,2-dichloroethane (15 mL) was mixed with powdered sodium triacetoxyboron hydride (290 mg, 1.37 mmol) and acetic acid (100 mg, 1.67 mmol) and stirred for 18 h at room temperature. The mixture was then diluted with ethyl acetate (80 mL), washed with saturated sodium hydrogencarbonate solution (20 mL) and dried with sodium sulphate. The solvent was removed in a vacuum and the residue was purified by flash chromatography (15 g, 12×2.5 cm) with methanol/dichloromethane (1:4).

Yield (Example 16, non-polar diastereomer): 145 mg (36%), white solid

Melting point: 65-70° C.

αD20: −11° (c 0.2, MeOH).

1H NMR (CDCl3): δ 1.40-1.60 (6H, s); 1.90-2.20 (8H, m); 2.25 (3H, s); 2.35-2.47 (2H, m); 3.22-3.33 (2H, m); 4.27 (1H, m); 6.60 (1H, s); 7.10 (1H, t, J=7.6 Hz); 7.18 (1H, t, J=7.6 Hz); 7.26-7.37 (7H, m); 7.57 (1H, d, J=8 Hz); 8.20 (1H, br s).

13C NMR (CDCl3): δ 165.1; 148.5; 137.7; 136.2; 127.6; 127.5; 127.3; 126.8; 123.3; 122.3; 121.8; 119.2; 118.7; 111.6; 111.0; 60.9; 54.2; 52.2; 37.6; 31.1; 30.0; 29.5; 28.9; 26.6; 10.9.

Yield (Example 17, polar diastereomer): 100 mg (25%), white solid

Melting point: 70-75° C.

αD60: −7° (c 0.2, MeOH).

1H NMR (CDCl3): δ 1.00 (2H, m); 1.63 (1H, m); 1.82 (1H, m); 2.08 (6H, br s); 2.22 (3H, s), 2.40-2.80 (6H, m); 3.18 (2H, m); 4.22 (1H, t, J=7 Hz); 6.60 (1H, s); 6.90 (1H, s); 7.06 (1H, t, J=7.6 Hz); 7.17 (1H, t, J=7.6 Hz); 7.26-7.36 (6H, m); 7.45 (1H, d, J=8 Hz); 7.96 (1H, br s).

13C NMR (CDCl3): δ 164.9; 148.4; 136.1; 135.6; 128.2; 128.0; 127.5; 126.8; 122.7; 122.4; 121.9; 119.3; 118.6; 111.5; 111.0; 62.3; 54.8; 54.6; 38.1; 31.5; 31.3; 31.0; 30.0; 28.9; 10.9.

Example 18 and Example 19

Step 1

(R)-tert-butyl-3-(1H-indol-3-yl)-1-oxo-1-(prop-2-ynylamino)propan-2-yl carbamate A solution of (R)-2-(tert-butoxycarbonylamino)-3-(1H-indol-3-yl)propionic acid (3.0 g, 9.9 mmol) in THF (20 mL) was mixed in portions with N,N'-carbonyldiimidazole (1.62 g, 10 mmol) at room temperature and stirred for 2 h at room temperature before propargylamine (826 mg, 15 mmol) was added in drops. After 1 h at room temperature, the mixture was diluted with diethyl ether (200 mL), washed with saturated sodium hydrogencarbonate solution (2×50 mL) and dried with sodium sulphate. The solvent was removed in a vacuum and the residue was recrystallised from diethyl ether.

Yield: 2.3 g (68%), white solid

Melting point: 105-108° C.

1H-NMR (CDCl3): 1.42 (9H, s); 2.14 (1H, t, J=2.4 Hz); 3.15-3.33 (2H, m); 3.93 (2H, br s); 4.43 (1H, br s); 5.10 (1H, br s); 6.00 (1H, br s); 7.06 (1H, d, J=2 Hz); 7.14 (1H, m); 7.21 (1H, m); 7.37 (1H, d, J=8 Hz); 7.65 (1H, d, J=8 Hz); 8.14 (1H, br s).

Step 2

(R)-tert-butyl-2-(1H-indol-3-yl)-1-(5-methyloxazol-2-yl)ethyl carbamate

A solution of (R)-tert-butyl-3-(1H-indol-3-yl)-1-oxo-1-(prop-2-ynylamino)propan-2-yl carbamate (2.20 g, 6.44 mmol) in acetonitrile (25 mL) was mixed with gold(III) chloride (190 mg, 0.63 mmol) at room temperature and stirred for 18 h at 50° C. The solvent was removed in a vacuum and the residue was purified by flash chromatography (60 g, 15×4 cm) with ethyl acetate/cyclohexane (1:1).

Yield: 1.30 g (59%), brownish solid
Melting point: 110-112° C.
1H-NMR (CDCl3): 1.41 (9H, s); 2.23 (3H, s); 3.38 (2H, m); 5.20 (2H, br s); 6.61 (1H, s); 6.90 (1H, s); 7.07 (1H, t, J=7.6 Hz); 7.16 (1H, t, J=7.6 Hz); 7.32 (1H, d, J=8 Hz); 7.43 (1H, d, J=8 Hz); 8.00 (1H, br s).

Step 3

(R)-2-(1H-indol-3-yl)-1-(5-methyloxazol-2-yl)ethylamine

A solution of (R)-tert-butyl-2-(1H-indol-3-yl)-1-(5-methyloxazol-2-yl)ethyl carbamate (1.0 g, 2.9 mmol) in dichloromethane (30 mL) was mixed in drops with trifluoroacetic acid (6 mL, 81 mmol) at 0° C. and stirred for 1 h at room temperature. The volatile constituents were then removed in a vacuum and the residue mixed with saturated sodium hydrogencarbonate solution (20 mL). After extraction with dichloromethane (3×20 mL) the organic phase was dried with sodium sulphate and the solvent removed in a vacuum.

Yield: 560 mg (80%), brown oil
1H-NMR (CDCl3): 2.09 (2H, br s); 2.29 (3H, s); 3.18 (1H, dd, J=14.4 and 8:4 Hz); 3.42 (1H, dd, J=14.4 and 5 Hz); 4.38 (1H, m); 6.61 (1H, s); 7.05 (1H, s); 7.10 (1H, m); 7.19 (1H, m); 7.35 (1H, d, J=8 Hz); 7.55 (1H, d, J=8 Hz); 8.09 (1H, brs).

Step 4

(R)—N$^4$-(2-(1H-indol-3-yl)-1-(5-methyloxazol-2-yl)ethyl)-N$^1$,N$^1$-dimethyl-1-phenylcyclohexane-1,4-diamine (Example 18, polar diastereomer and Example 19, non-polar diastereomer)

A solution of (R)-2-(1H-indol-3-yl)-1-(5-methyloxazol-2-yl)ethylamine (240 mg, 1.0 mmol) and 4-dimethylamino-4-phenylcyclohexanone (218 mg, 1.0 mmol) in 1,2-dichloroethane (15 mL) was mixed with powdered sodium triacetoxyboron hydride (317 mg, 1.5 mmol) and acetic acid (120 mg, 2.0 mmol) and stirred for 18 h at room temperature. The mixture was then diluted with ethyl acetate (80 mL), washed with sodium hydrogencarbonate solution (20 mL) and dried with sodium sulphate. The solvent was removed in a vacuum and the residue purified by flash chromatography (15 g, 12×2.5 cm) with methanol/dichloromethane (1:4).

Example 18

Polar Diastereomer

Yield: 120 mg (27%), white solid
Melting point: 70-75° C.
$[\alpha]_D^{20}$: +11° (c 0.2, MeOH).
$^1$H-NMR (CDCl$_3$): 1.00 (2H, m); 1.63 (1H, m); 1.82 (1H, m); 2.08 (6H, br s); 2.22 (3H, s), 2.40-2.80 (6H, m); 3.18 (2H, m); 4.22 (1H, t, J=7 Hz); 6.60 (1H, s); 6.90 (1H, s); 7.06 (1H, t, J=7.6 Hz); 7.17 (1H, t, J=7.6 Hz); 7.26-7.36 (6H, m); 7.45 (1H, d, J=8 Hz); 7.96 (1H, br s).
$^{13}$C-NMR (CDCl$_3$): 164.9; 148.4; 136.1; 135.6; 128.2; 128.0; 127.5; 126.8; 122.7; 122.4; 121.9; 119.3; 118.6; 111.5; 111.0; 62.3; 54.8; 54.6; 38.1; 31.5; 31.3; 31.0; 30.0; 28.9; 10.9.
LC-MS (method 8): m/z: [M+H]$^+$=443.3, R$_1$=1.5 min.

Example 19

Non-Polar Diastereoisomer

Yield: 170 mg (38%), white solid
Melting point: 65-70° C.
$[\alpha]_D^{20}$: +14° (c 0.2, MeOH).
$^1$H-NMR (CDCl$_3$): 1.40-1.60 (6H, s); 1.90-2.20 (8H, m); 2.25 (3H, s); 2.35-2.47 (2H, m); 3.22-3.33 (2H, m); 4.27 (1H, m); 6.60 (1H, s); 7.10 (1H, t, J=7.6 Hz); 7.18 (1H, t, J=7.6 Hz); 7.26-7.37 (7H, m); 7.57 (1H, d, J=8 Hz); 8.20 (1H, br s).
$^{13}$C-NMR (CDCl$_3$): 165.1; 148.5; 137.7; 136.2; 127.6; 127.5; 127.3; 126.8; 123.3; 122.3; 121.8; 119.2; 118.7; 111.6; 111.2; 60.9; 54.2; 52.2; 37.6; 31.1; 30.0; 29.5; 28.9; 26.6; 10.9.
LC-MS (method 8): m/z: [M+H]$^+$=443.3, R$_t$=2.35 min.

Example 20 and Example 21

Step 1

(S)-tert-butyl-1-amino-3-(1H-indol-3-yl)-1-thioxopropan-2-yl carbamate

A solution of (S)-tert-butyl-1-amino-3-(1H-indol-3-yl)-1-oxopropan-2-yl carbamate (500 mg, 1.6 mmol) in anhydrous 1,2-dimethoxyethane (10 mL) was mixed in portions with sodium hydrogencarbonate (520 mg, 6.2 mmol) and diphosphorus pentasulphide (730 mg, 3.2 mmol) and stirred overnight at room temperature. The reaction mixture was then concentrated to low volume in a vacuum, the residue taken up in ethyl acetate (30 mL) and washed with water and saturated sodium hydrogencarbonate solution (3×20 mL each). The organic phase was dried with sodium sulphate and concentrated to low volume in a vacuum. The raw product (600 mg) was taken up in diethyl ether/cyclohexane (10 mL each) and concentrated to low volume again. During this a white solid separated out.

Yield: 510 mg (100%), white solid
Melting point: 57-62° C.
$^1$H-NMR (DMSO-d$_6$): 1.30 (s, 9H); 2.88-3.00 (m, 1H); 3.10-3.20 (m, 1H); 4.40-4.56 (m, 1H); 6.72 (d, 1H, J=8.4 Hz); 6.94-7.10 (m, 2H); 7.17 (s, 1H); 7.32 (d, 1H, J=8.3 Hz); 7.65 (d, 1H, J=7.4 Hz); 9.16 (s, 1H); 9.61 (s, 1H); 10.80 (s, 1H).

Step 2 tert-butyl-(1S)-1-(4-hydroxy-4-methyl-4,5-dihydrothiazol-2-yl)-2-(1H-indol-3-yl)ethyl]carbamate A solution of (S)-tert-butyl-1-amino-3-(1H-indol-3-yl)-1-thioxopropan-2-yl carbamate (400 mg, 1.2 mmol) in anhydrous 1,2-dimethoxyethane (20 mL) was mixed with powdered potassium hydrogencarbonate (600 mg, 6 mmol) and chloroacetone (556 mg, 447 μL, 6 mmol) and stirred for 8 h at 70° C. and over the weekend at 45° C. The reaction mixture was then filtered and the filtrate concentrated to low volume in a vacuum.

Yield: 500 mg (100%), amber-coloured oil

Step 3

(S)-tert-butyl-2-(1H-indol-3-yl)-1-(4-methylthiazol-2-yl)ethyl carbamate

A solution of tert-butyl-(1S)-1-(4-hydroxy-4-methyl-4,5-dihydrothiazol-2-yl)-2-(1H-indol-3-yl)ethyl]carbamate (280 mg, 0.74 mmol) in toluol (20 mL) was mixed with sodium sulphate (1.00 g) and stirred for 1 h with reflux. The mixture was then filtered, the filtrate concentrated to low volume in a vacuum and the residue (260 mg) purified by flash chromatography (18 g, 20×2.0 cm) with ethyl acetate/cyclohexane (1:2).

Yield: 185 mg (70%), brownish oil
$^1$H-NMR (DMSO-$d_6$): 1.31 (s, 9H); 2.36 (d, 3H, J=1 Hz); 3.05-3.17 (m, 1H); 3.37-3.42 (m, 1H); 4.92-5.02 (m, 1H); 6.95-7.15 (m, 4H); 7.34 (d, 1H, J=8.0 Hz); 7.54 (d, 1H, J=7.8 Hz); 7.63 (d, 1H, J=8.3 Hz); 10.82 (s, 1H).

Step 4

(S)-2-(1H-indol-3-yl)-1-(4-methylthiazol-2-yl)ethylamine

A solution of (S)-tert-butyl-2-(1H-indol-3-yl)-1-(4-methylthiazol-2-yl)ethyl carbamate (2.13 g, 5.95 mmol) in anhydrous dichloromethane (15 mL) was mixed with trifluoroacetic acid (5 mL) and stirred for 1 h at room temperature. The solution was then concentrated to low volume in a vacuum, the residue taken up in dichloromethane (100 mL) and washed with 2M potassium carbonate solution (3×20 mL). The organic phase was dried with sodium sulphate and concentrated to low volume in a vacuum.

Yield: 1.49 g (97%), brown oil
$^1$H-NMR (DMSO-$d_6$): 2.07-2.17 (br s, 2H); 2.34 and 2.35 (d, 3H, J=0.8 Hz); 2.91 (dd, 1H, J=14.2, 8.5 Hz); 3.28 (dd, 1H, J=14.2, 4.5 Hz); 4.35 (dd, 1H, J=8.5, 4.4 Hz); 6.93-7.00 (m, 1H); 7.02-7.09 (m, 2H); 7.15 (d, 1H, J=2.2 Hz); 7.33 (d, 1H, J=8.0 Hz); 7.49 (d, 1H, J=7.8 Hz); 10.85 (s, 1H).
$^{13}$C-NMR (DMSO-$d_6$): 17.0; 29.3; 34.4; 54.0; 10.4; 111.3; 113.3; 118.3; 120.8; 123.8; 127.4; 136.2; 151.5; 177.7.

Step 5

(S)—N$^4$-(2-(1H-indol-3-yl)-1-(4-methylthiazol-2-yl)ethyl)-N$^1$,N$^1$-dimethyl-1-phenylcyclohexane-1,4-diamine (Example 20, non-polar diastereomer, Example 21, polar diastereomer)

A solution of (S)-2-(1H-indol-3-yl)-1-(4-methylthiazol-2-yl)ethylamine (500 mg, 1.94 mmol) and 4-dimethylamino-4-phenylcyclohexanone (421 mg, 1.94 mmol) in anhydrous tetrahydrofuran (40 mL) was mixed with sodium sulphate (1.00 g) and stirred for 3 h at room temperature. After adding acetic acid (291 mg, 287 μL, 4.85 mmol), sodium triacetoxyboron hydride (574 mg, 2.71 mmol) was added and the mixture stirred overnight at room temperature. The mixture was then filtered, the filtrate concentrated to low volume in a vacuum, the residue mixed with 1M potassium carbonate solution (50 mL) and extracted with ethyl acetate (3×30 mL). The combined organic phases were dried with sodium sulphate and concentrated to low volume in a vacuum. The raw product (750 mg) was purified by flash chromatography (100 g, 20×4.0 cm) with ethyl acetate/methanol [97:3→9:1 and 1% NH$_3$ in each case (33% in water)].

Example 20

Non-Polar Diastereoisomer

Yield: 400 mg (45%), white solid
Melting point: 70-72° C.
$^1$H-NMR (DMSO-$d_6$): 1.20-1.48 (m, 6H); 1.82 (s, 6H); 2.10-2.24 (m, 1H); 2.28-2.38 (m, 2H); 2.33 (d, 3H, J=1.0 Hz); 2.96 (dd, 1H, J=14.2, 8.5 Hz); 3.21 (dd, 1H, J=14.3, 4.5 Hz); 4.33 (dd, 1H, J=8.4, 4.7 Hz), 6.99 (ddd, 1H, J=8.0, 7.1, 1.1 Hz); 7.04-7.11 (m, 2H); 7.14-7.41 (m, 8H); 7.50 (d, 1H, J=7.5 Hz); 10.88 (s, 1H).
$^{13}$C-NMR (DMSO-$d_6$): 17.0; 27.0; 28.7; 30.2; 30.5; 33.4; 37.4; 53.6; 57.9; 58.6; 110.0; 111.4; 113.5; 118.0; 120.9; 124.0; 126.1; 126.7; 127.2; 127.3; 136.2; 138.8; 151.6; 177.9.
LC-MS (method 7): m/z: [M+H]$^+$=459.3, R$_1$=2.7 min.
Rotation value: $[\alpha]_D^{24}$=+1.4° (c 1.0, MeOH).

Example 21

Polar Diastereoisomer

Yield: 186 mg (21%), yellowish oil
$^1$H-NMR (CDCl$_3$): 0.66-0.77 (m, 1H); 0.85-1.07 (m, 1H); 1.43-1.76 (m, 4H); 1.97 (s, 6H); 2.23-2.33 (m, 1H); 2.45 (d, 3H, J=0.9 Hz); 2.39-2.53 (m, 2H); 2.98 (dd, 1H, J=14.5, 8.8 Hz); 3.30 (dd, 1H, J=14.5, 4.8 Hz), 4.43 (dd, 1H, J=8.8, 4.8 Hz); 6.75 (d, 1H, J=1.0 Hz); 6.91 (d, 1H, J=2.3 Hz); 7.07 (ddd, 1H, J=8.0, 7.1, 1.0 Hz); 7.13-7.25 (m, 5H); 7.28-7.34 (m, 3H); 7.58 (d, 1H, J=7.9 Hz); 7.99 (s, 1H).
$^{13}$C-NMR (CDCl$_3$): 17.2; 28.7; 30.4; 31.3; 31.6; 34.0; 38.2; 55.0; 58.5; 61.5; 111.1; 111.7; 113.0; 118.8; 119.3; 122.0; 122.8; 126.4; 127.4; 127.7; 127.9; 136.2; 136.4; 152.3; 177.7.
LC-MS (method 7): m/z: [M+H]$^+$=459.3, R$_t$=1.9 min.
Rotation value: $[\alpha]_D^{24}$=−0.15° (c 1.0, MeOH).

Example 22 and Example 23

Step 1

(R)-tert-butyl-1-amino-3-(1H-indol-3-yl)-1-oxopropan-2-yl carbamate

A solution of (R)-2-(tert-butoxycarbonylamino)-3-(1H-indol-3-yl)propionic acid (7.00 g, 23 mmol) and 1,1'-carbonyldiimidazole (4.44 g, 27.3 mmol) in anhydrous tetrahydrofuran (200 mL) was stirred for 2 h at room temperature. This solution was then added in drops to a solution of 33% aqueous ammonia (14 mL, 230 mmol) in tetrahydrofuran (50 mL) and stirred for 20 h at room temperature. The reaction solution was concentrated to low volume in a vacuum and the residue taken up in water (200 mL). After 30 min the product separated out as a white solid, which was filtered off, washed with water and dried over potassium hydroxide in an exsiccator.

Yield: 6.90 (99%), white solid
Melting point: 113-118° C.
$^1$H-NMR (DMSO-$d_6$): 1.31 (s, 9H); 2.89 (dd, 1H, J=14.5, 9.1 Hz); 3.07 (dd, 1H, J=14.5, 4.7 Hz); 4.09-4.19 (m, 1H); 6.62 (d, 1H, J=8.2 Hz); 6.93-7.14 (m, 4H); 7.29-7.38 (m, 2H); 7.60 (d, 1H, J=7.7 Hz); 10.77 (s, 1H).

Step 2

(R)-tert-butyl-1-amino-3-(1H-Indol-3-yl)-1-thioxopropan-2-yl carbamate

A solution of (R)-tert-butyl-1-amino-3-(1H-indol-3-yl)-1-oxopropan-2-yl carbamate (6.80 g, 22.4 mmol) in anhydrous dimethoxyethane (100 mL) was mixed in portions with sodium hydrogencarbonate (7.14 g, 85.1 mmol) and diphosphorus pentasulphide (10.2 g, 44.8 mmol) and stirred overnight at room temperature. The reaction mixture was concentrated to low volume in a vacuum, the residue taken up in ethyl acetate (100 mL) and washed with water and saturated sodium hydrogencarbonate solution (3×50 mL each). The organic phase was dried with sodium sulphate and concentrated to low volume in a vacuum. The raw product was taken up in diethyl ether/cyclohexane (50 mL each) and concentrated to low volume again. During this, the product separated out as a white solid, which was filtered off.

Yield: 6.49 g (91%), white solid
Melting point: 55-65° C.
$^1$H-NMR (DMSO-$d_6$): 1.30 (s, 9H); 2.95 (dd, 1H, J=9.3 Hz); 3.17 (dd, 1H, J=14.3, 4.3 Hz); 4.44-4.54 (m, 1H); 6.70 (d, 1H, J=8.4 Hz); 6.95-7.09 (m, 2H); 7.16 (s, 1H); 7.33 (d, 1H, J=8.0 Hz); 7.65 (d, 1H, J=7.7 Hz); 9.15 (s, 1H); 9.61 (s, 1H); 10.80 (s, 1H).

Step 3 tert-butyl-(1R)-1-(4-hydroxy-4-methyl-4,5-dihydrothiazol-2-yl)-2-(1H-indol-3-yl)ethyl carbamate A solution of (R)-tert-butyl-1-amino-3-(1H-Indol-3-yl)-1-thioxopropan-2-yl carbamate (6.49 g, 20.3 mmol) in anhydrous dimethoxyethane (100 mL) was mixed with powdered potassium hydrogencarbonate (10.1 g, 101 mmol) and chloroacetone (9.69 g, 8.4 mL, 101 mmol) and stirred for 8 h at 70° C. and over the weekend at 45° C. The reaction mixture was then filtered and the filtrate concentrated to low volume in a vacuum.

Yield: 7.12 g (93%), amber-coloured oil

Step 4

(R)-tert-butyl-2-(1H-indol-3-yl)-1-(4-methylthiazol-2-yl)ethyl carbamate

A solution of tert-butyl-(1R)-1-(4-hydroxy-4-methyl-4,5-dihydrothiazol-2-yl)-2-(1H-indol-3-yl)ethyl carbamate (7.12 g, 18.9 mmol) in toluol (150 mL) was mixed with sodium sulphate (9.00 g) and stirred for 1 h with reflux. The mixture was filtered, the filtrate concentrated to low volume in a vacuum and the residue purified by flash chromatography (400 g, 20×7.5 cm) with ethyl acetate/cyclohexane (1:2).

Yield: 4.97 g (74%), brownish oil
$^1$H-NMR (DMSO-$d_6$): 1.31 (s, 9H); 2.36 (s, 3H); 3.03-3.20 (m, 1H); 3.35-3.45 (m, 1H); 4.97 (dt, 1H, J=10.0, 4.6 Hz); 6.95-7.14 (m, 4H); 7.33 (d, 1H, J=8.1 Hz); 7.53 (d, 1H, J=7.7 Hz), 7.60 (d, 1H, J=8.4 Hz); 10.80 (s, 1H).

Step 5

(R)-2-(1H-indol-3-yl)-1-(4-methylthiazol-2-yl)ethylamine

A solution of (R)-tert-butyl-2-(1H-indol-3-yl)-1-(4-methylthiazol-2-yl)ethyl carbamate (4.97 g, 13.9 mmol) in anhydrous dichloromethane (40 mL) was mixed with trifluoroacetic acid (7 mL) and stirred for 24 h at room temperature. The solution was then concentrated to low volume in a vacuum, the residue taken up in dichloromethane (100 mL) and washed with 2M potassium carbonate solution (3×30 mL). The organic phase was dried with sodium sulphate and concentrated to low volume in a vacuum.

Yield: 3.47 g (97%), brown oil
$^1$H-NMR (DMSO-$d_6$): 2.00-2.18 (br s, 2H); 2.34 (d, 3H, J=1 Hz); 2.92 (dd, 1H, J=14.3, 8.4 Hz); 3.28 (dd, 1H, J=14.4, 4.7 Hz); 4.36 (dd, 1H, J=8.4, 4.4 Hz); 6.93-7.09 (m, 3H); 7.15 (d, 1H, J=2.3 Hz); 7.31-7.36 (m, 1H); 7.50 (d, 1H, J=7.8 Hz); 10.85 (s, 1H).

Step 6

(R)—N$^4$-(2-(1H-indol-3-yl)-1-(4-methylthiazol-2-yl)ethyl)-N$^1$,N$^1$-dimethyl-1-phenylcyclohexane-1,4-diamine (Example 22, non-polar diastereomer and Example 23, polar diastereomer)

A solution of (R)-2-(1H-indol-3-yl)-1-(4-methylthiazol-2-yl)ethylamine (500 mg, 1.94 mmol) and 4-dimethylamino-4-phenylcyclohexanone (421 mg, 1.94 mmol) in anhydrous tetrahydrofuran (40 mL) was mixed with sodium sulphate (1.00 g) and stirred for 3 h at room temperature. After adding, acetic acid (291 mg, 287 µL, 4.85 mmol), sodium triacetoxyboron hydride (574 mg, 2.71 mmol) was added and the mixture stirred overnight at room temperature. The mixture was then filtered, the filtrate concentrated to low volume in a vacuum, the residue mixed with 1M potassium carbonate solution (50 mL) and extracted with ethyl acetate (3×30 mL). The combined organic phases were dried with sodium sulphate and concentrated to low volume in a vacuum. The raw product (876 mg) was purified by flash chromatography (100 g, 20×4.0 cm) with ethyl acetate/methanol [95:5→9:1 and 1% ammonia in each case (33% in water)]. The non-polar diastereoisomer (450 mg) was purified once again by flash chromatography (38 g, 20×2.5 cm) with dichloromethane/methanol (300:9) and 1% ammonia (33% in water). The polar diastereoisomer (262 mg) was also purified once again by flash chromatography (18 g, 20×2.0 cm) with dichloromethane/methanol (24:1) and 1% ammonia (33% in water).

Example 22

Non-Polar Diastereoisomer

Yield: 252 mg (28%), white solid
Melting point: 75-77° C.
$^1$H-NMR (DMSO-$d_6$): 1.12-1.47 (m, 6H); 1.81 (s, 6H); 2.10-2.24 (m, 1H); 2.27-2.37 (m, 2H); 2.33 (d, 3H, J=0.9 Hz); 2.96 (dd, 1H, J=14.3, 8.5 Hz); 3.21 (dd, 1H, J=14.2, 4.7 Hz); 4.33 (dd, 1H, J=8.4, 4.7 Hz); 6.99 (ddd, 1H, J=7.9, 7.1, 1.0 Hz); 7.04-7.11 (m, 2H); 7.14-7.37 (m, 7H); 7.50 (d, 1H, J=7.6 Hz); 10.87 (s, 1H). 1H could not be identified.
$^{13}$C-NMR (DMSO-$d_6$): 17.0; 27.1; 28.7; 30.2; 30.5; 33.5; 37.4; 53.6; 57.9; 58.7; 110.1; 111.4; 113.6; 118.1; 118.4; 121.0; 124.0; 126.1; 126.7; 127.2; 127.3; 136.2; 138.8; 151.6; 177.9.
LC-MS (method 7): m/z: [M+H]$^+$=459.3, R. 2.0 min.
Rotation value: $[\alpha]_D^{24}$=+0.55° (c 1.0, CHCl$_3$).

Example 23

Polar Diastereoisomer

Yield: 108 mg (12%), white solid
Melting point: 71-74° C.
$^1$H-NMR (CDCl$_3$): 0.68-0.84 (m, 1H); 0.98-1.14 (m, 1H); 1.39-1.84 (m, 5H); 1.97 (s, 6H); 2.26-2.40 (m, 1H); 2.42-2.58 (m, 2H); 2.44 (s, 3H); 3.03 (dd, 1H, J=14.4, 8.8 Hz); 3.35 (dd, 1H, J=14.4, 4.7 Hz); 4.49 (dd, 1H, J=8.8, 4.7 Hz); 6.78-6.81 (m, 1H); 6.91 (d, 1H, J=2.1 Hz); 7.05-7.40 (m, 8H); 7.61 (d, 1H, J=7.8 Hz); 8.48 (s, 1H).

$^{13}$C-NMR (DMSO-d$_6$): 17.2; 28.7; 30.4; 31.3; 31.6; 34.0; 38.2; 55.0; 58.5; 61.3; 111.0; 111.5; 113.0; 118.8; 119.3; 121.9; 122.9; 126.3; 127.4; 127.7; 127.8; 136.2; 136.6; 152.2; 177.7.

LC-MS (method 7): m/z: [M+H]$^+$=459.3, R$_t$ 2.0 min.
Rotation value: [α]$_D^{24}$=+1.97° (c 1.0, CHCl$_3$).

Example 24 and Example 25

Step 1

2-(1H-indol-3-yl)-1-phenylethanone

NaCN (1.4 g, 29 mmol) was provided in absolute dimethylformamide (10 ml) in argon. At a bath temperature of 35° C. benzaldehyde (3 ml, 29 mmol) dissolved in absolute dimethylformamide (10 ml) was added in drops within 1.5 h and stirred for a further 0.5 h at this temperature. Gramine (10.1 g, 58 mmol) dissolved in absolute dimethylformamide (30 ml) was added in drops to this reaction solution within 2 h at an inside temperature of 70° C. The mixture was stirred a further 1 h at this temperature. For work up the vessel contents were placed in water (150 ml). The aqueous phase was acidified with 2N HCl to separate non-converted gramine as, a water-soluble hydrochloride. The aqueous phase was then extracted with chloroform (3×50 ml). The combined extracts were washed with NaHCO$_3$ solution (50 ml) and dried over Na$_2$SO$_4$. The volatile constituents were then completely removed in a vacuum. The residue (9 g) obtained after distilling off the solvent was purified by column chromatography [silica gel 60 (300 g); cyclohexane/ethyl acetate 6:1 (1500 ml)].

Yield: 1 g (14%) yellow oil

Step 2

2-(1H-indol-3-yl)-1-phenylethanone-oxime 2-(1H-indol-3-yl)-1-phenylethanone (0.97 g, 4.12 mmol) dissolved in absolute ethanol (20 ml) was added to a solution of hydroxylamine hydrochloride (0.97 g, 13.95 mmol) and potassium acetate (1.54 g, 15.74 mmol) in absolute ethanol (20 ml). This reaction mixture was stirred for 24 h at room temperature. The batch was then boiled for 3 h with reflux. The batch was then dissolved in water (20 ml) at 70° C. The batch was then left to stand for 5 h at 4° C. Since no solid separated out, the volatile constituents were removed completely in a vacuum. The residue was mixed with water (10 ml) and the pH value of the solution adjusted to pH 11 with 5N sodium hydroxide solution. The mixture was then extracted with ethyl acetate (5×30 ml). The combined organic phases were dried with sodium sulphate, filtered and all the volatile constituents removed in a vacuum. Yield: 90% (990 mg) yellow-brown oil Step 3

2-(1H-indol-3-yl)-1-phenylethylamine 2-(1H-indol-3-yl)-1-phenylethanone-oxime (0.2 g, 0.75 mmol) dissolved in ethanol (10 ml) was mixed in portions with sodium pieces (500 mg, 21 mmol) in the boiling heat. This reaction mixture was stirred with reflux until the metal was fully dissolved. After cooling in an ice bath, water (15 ml) was carefully added to the reaction solution. The volatile constituents were then removed in a vacuum. The aqueous residue was extracted with ethyl acetate (3×30 ml). The combined organic phases were dried with sodium sulphate, filtered and all the volatile constituents removed in a vacuum. The residue (163 mg) obtained after distilling off the solvent was purified by column chromatography [silica gel 60 (30 g); methanol (500 ml)].

Yield: 45 mg (25%), light yellow oil.

Since an increase in the batch led to losses in yield, this preparation was repeated three times.

Step 4

N$^4$-(2-(1H-indol-3-yl)-1-phenylethyl)-N$^1$,N$^1$-dimethyl-1-phenylcyclohexane-1,4-diamine (Example 24, non-polar diastereoisomer and Example 25, polar diastereoisomer)

2-(1H-indol-3-yl)-1-phenylethylamine (135 mg, 0.57 mmol) and 4-dimethylamino-4-phenylcyclohexanone (124 mg, 0.57 mmol) were dissolved in tetrahydrofuran (10 ml) and 1,2-dichloroethane (5 ml) in argon. Glacial acetic acid (0.035 ml, 0.57 mmol) were added to the clear solution. After a reaction time of 15 min the reaction mixture was mixed with NaBH(OAc)$_3$ (180 mg, 0.8 mmol) and stirred for 2 d at room temperature. For work up of the batch the mixture was mixed with saturated NaHCO$_3$ solution (40 ml) and stirred for 15 min. The aqueous phase was extracted with dichloromethane (2×30 ml). The combined organic phases were concentrated to low volume after drying over Na$_2$SO$_4$, and a light brown oil was obtained. The chromatographic separation of the substance mixture on silica gel 60 (50 g) was conducted with methanol (600 ml). The more non-polar amine was obtained as a beige-coloured compound with a yield of 67% (168 mg). No melting point could be determined. The more polar amine was obtained as a beige-coloured compound with a yield of 30% (75 mg). No melting point could be determined.

Example 24

Non-Polar Diastereomer $^{13}$C-NMR (101 MHz, DMSO-D$_6$) δ ppm: 27.0, 29.4, 30.5, 30.9, 35.4, 37.8, 52.4, 59.6, 60.0, 111.1, 113.2, 118.9, 119.2, 121.9, 122.8, 126.2, 126.4, 126.7, 127.1, 127.2, 127.3, 127.6, 128.2, 136.4, 139.0, 145.3

Example 25

Polar Diastereomer $^{13}$C-NMR (101 MHz, DMSO-D$_6$) δ ppm: 29.1, 30.8, 31.6, 318, 35.2, 38.354.4, 60.4, 61.4, 111.0, 113.0, 118.8, 119.2, 121.9, 122.5, 126.3, 126.7, 127.2, 127.6, 127.7, 128.0, 128.2, 136.2, 136.9, 145.2

Step 5

N$^4$-(2-(1H-indol-3-yl)-1-phenylethyl)-N$^1$,N$^1$-dimethyl-1-phenylcyclohexane-1,4-diamine dihydrochloride (Example 24, non-polar diastereoisomer and Example 25, polar diastereoisomer)

Example 24

Non-Polar Diastereomer

For production of the hydrochloride N$^4$-(2-(1H-Indol-3-yl)-1-phenylethyl)-N$^1$,N$^1$-dimethyl-1-phenylcyclohexane-1, 4-diamine (more non-polar amine) (160 mg, 0.36 mmol) was dissolved in ethyl methyl ketone (15 ml), mixed with trimethylchlorosilane (115 μl, 0.9 mmol) and stirred for 3 h at room temperature. The precipitated colourless hydrochloride was aspirated and dried. The hydrochloride was obtained with a yield of 100 mg (53%) and a melting point of 198-202° C.

Example 25

Polar Diastereomer

For production of the hydrochloride $N^4$-(2-(1H-Indol-3-yl)-1-phenylethyl)-$N^1$,$N^1$-dimethyl-1-phenylcyclohexane-1,4-diamine (more polar amine) (70 mg, 0.16 mmol) was dissolved in ethyl methyl ketone (7 ml), mixed with trimethylchlorosilane (51 μl, 0.4 mmol) and stirred for 3 h at room temperature. The precipitated colourless hydrochloride was aspirated and dried. The hydrochloride was obtained with a yield of 70 mg (85%) and a melting point of 208-217° C.

Example 26, Example 27, Example 28 and Example 29

Step 1

2-(4-dimethylamino-4-phenylcyclohexylamino)-3-(1H-indol-3-yl)propionamide (non-polar diastereomer and polar diastereomer)

DL-tryptophanamide hydrochloride (5.00 g, 20.8 mmol) was taken up in 0.5 M sodium hydroxide solution (20 mL), the solution was then adjusted to pH 9 with 4 M sodium hydroxide solution and then extracted with ethyl acetate (5×30 mL). The combined organic phases were dried with sodium sulphate and concentrated to low volume in a vacuum. The DL-tryptophanamide (3.87 g, 19.04 mmol) thus obtained was dissolved in tetrahydrofuran (105 mL) and 1,2-dichloroethane (60 mL) and mixed with 4-dimethylamino-4-phenylcyclohexanone (4.13 g, 19.0 mmol). The solution was mixed with glacial acetic acid (1.09 mL, 19.04 mmol) and sodium sulphate (9.52 g) and stirred for 15 min. Sodium triacetoxyboron hydride (5.71 g, 26.6 mmol) was then added, the reaction mixture was stirred overnight at room temperature, then mixed with saturated sodium hydrogencarbonate solution (225 mL) and stirred for 15 min. The phase separation the aqueous phase was extracted with dichloromethane (2×40 mL). The combined organic phases were dried with sodium sulphate and concentrated to low volume in a vacuum. The raw product (7.6 g) was purified by flash chromatography (500 g, 20×7.6 cm) with ethyl acetate/methanol (1:1).
Non-Polar Diastereoisomer
 Yield: 3.88 g (50%), white amorphous solid
 $^1$H-NMR (DMSO-$d_6$): 1.22-1.36 (m, 2H); 1.36-1.56 (m, 4H); 1.85 (s, 6H); 2.24-2.46 (m, 3H); 2.81 (dd, 1H, J=14.2, 7.9 Hz); 3.01 (dd, 1H, J=14.3, 5.4 Hz); 3.39 (t, 1H, J=6.5 Hz); 6.94-7.01 (m, 2H); 7.06 (ddd, 1H, J=8.1, 7.0, 1.1 Hz); 7.16-7.38 (m, 9H); 7.56 (d, 1H, J=7.8 Hz); 10.83 (s, 1H).
Polar Diastereoisomer
 Yield: 1.64 g (21%), white amorphous solid
 $^1$H-NMR (DMSO-$d_6$): 0.75 (m, 1H); 0.92 (m, 1H); 1.35-1.72 (m, 5H); 1.86 (s, 6H); 2.30-2.48 (m, 3H); 2.71 (dd, 1H, J=14.3, 7.3 Hz); 2.91 (dd, 1H, J=14.3, 5.9 Hz); 3.28 (t, 1H, J=6.6 Hz); 6.87-6.96 (m, 2H); 7.03 (dt, 1H, J=7.5, 1.0 Hz); 7.07 (d, 1H, J=7.2 Hz); 7.18-7.39 (m, 7H); 7.49 (d, 1H, J=78 Hz); 10.74 (s, 1H).

Step 2

N-[1-cyano-2-(1H-indol-3-yl)ethyl]-N-(4-dimethylamino-4-phenylcyclohexyl)-2,2,2-trifluoracetamide (non-polar diastereomer)

A solution of 2-(4-dimethylamino-4-phenylcyclohexylamino)-3-(1H-indol-3-yl)propionamide (non-polar diastereomer) (500 mg, 1.23 mmol) in anhydrous tetrahydrofuran (30 mL) and triethylamine (2 mL) was cooled to −15° C. and mixed with trifluoroacetic anhydride (777 mg, 514 μL, 3.69 mmol). The mixture was stirred for 3 h at −15° C. and then concentrated to low volume in a vacuum. The residue was mixed with 5% sodium hydrogencarbonate solution (30 mL) and the aqueous suspension extracted with dichloromethane (3×20 mL). The combined organic phases were ? with sodium hydrogencarbonate solution (3×20 mL), dried with sodium sulphate and concentrated to low volume in a vacuum. The raw product (539 mg) was purified by flash chromatography (85 g, 20×3.7 cm) with dichloromethane/methanol (95:5).
 Yield: 382 mg (64%), yellow solid
 Melting point: 230° C.
 $^1$H-NMR (DMSO-$d_6$): 0.94-1-06 (m, 1H); 1.23-1.45 (m, 2H); 1.55-1.75 (m, 2H); 1.95-2.10 (m, 2H); 1.91 (s, 6H); 2.75 (br d, 1H, J=11.7 Hz); 3.42 (dd, 1H, J=7.2 and 14.2 Hz); 3.66 (dd, 1H, J=8.4 and 14.2 Hz); 3.70-3.85 (m, 1H); 4.70 (t, 1H, J=7.8 Hz); 7.04 (t, 1H, J=7.4 Hz); 7.12 (t, 1H, J=7.3 Hz); 7.21-7.38 (m, 6H); 7.41 (d, 1H, J=8.0 Hz); 7.63 (d, 1H, J=7.7 Hz); 11.07 (s, 1H).
 $^{13}$C-NMR (DMSO-$d_6$): 24.2; 24.9; 25.1; 25.9; 31.2; 37.2; 37.5; 45.6; 45.9; 54.7; 57.2; 57.3; 66.8; 107.2; 111.8; 115.7 (q, J=288 Hz); 16.9; 117.7; 118.6; 121.3; 125.1; 126.4; 126.6; 127.3; 128.1; 136.1; 138.1; 155.7 (q, J=36 Hz).
 LC-MS (method 8): [M+H]$^+$: m/z=483.3, $R_t$=2.7 min.

Step 3

N-(2-(1H-indol-3-yl)-1-(1H-tetrazol-5-yl)ethyl)-N-(4-dimethylamino-4-phenylcyclohexyl)-2,2,2-trifluoroacetamide (Example 26, non-polar diastereomer)

A solution of N-[1-Cyano-2-(1H-indol-3-yl)ethyl]-N-(4-dimethylamino-4-phenylcyclohexyl)-2,2,2-trifluoroacetamide (non-polar diastereomer) (241 mg, 0.5 mmol) in N,N-dimethylformamide (5 mL) and toluol (5 mL) was mixed with sodium azide (325 mg, 5.0 mmol) and triethylamine hydrochloride (688 mg, 5.0 mmol) and stirred for 2 d at 80° C. The solvent was then removed in a vacuum. The residue was repeatedly mixed with toluol and each time concentrated to low volume again in a vacuum. The raw product was purified by flash chromatography (37 g, 20×2.1 cm) with dichloromethane/methanol [8:2+1% NH$_3$ (32% in H$_2$O)].

Example 26

Non-Polar Diastereomer

Yield: 219 mg (83%), beige-coloured solid
 Melting point: 216° C.
 $^1$H-NMR (DMSO-$d_6$): 0.74 (d, 1H, J=10.8 Hz); 1.12-1.44 (m, 2H); 1.50-1.68 (m, 1H); 1.70-1.80 (m, 1H); 1.86 (s, 5.4H); 2.00 (s, 0.6H); 2.10-2.28 (m, 1H); 2.39 (d, 1H, J=14.2 Hz); 2.78 (d, 1H); 3.68 (dd, 1H, J=14.3, 8.1 Hz); 3.70-3.80

(m, 1H); 3.97 (dd, 1H, J=6.8, 14.3 Hz); 5.20 (t, 0.9H, J=7.2 Hz); 5.44 (m, 0.1H); 7.02 (ddd, 1H, J=7.9, 7.0, 1.0 Hz); 7.09 (ddd, 1H, J=7.9, 7.0, 1.0 Hz); 7.14 (d, 1H, J=2.3 Hz), 7.20-7.40 (m, 6H); 7.36 (d, 1H(J=8.0 Hz); 7.67 (d, 1H, J=7.4 Hz); 10.75 (s, 0.1H); 10.91 (s, 0.9H).

LC-MS (method 8): [M+H]$^+$: m/z=526.3, R$_t$=2.4 min.

Step 4

N$^4$-(2-(1H-indol-3-yl)-1-(1H-tetrazol-5-yl)ethyl)-N$^1$, N$^1$-dimethyl-1-phenylcyclohexane-1,4-diamine (Example 27, non-polar diastereomer)

A suspension of N-(2-(1H-Indol-3-yl)-1-(1H-tetrazol-5-yl)ethyl)-N-(4-dimethylamino-4-phenylcyclohexyl)-2,2,2-trifluoroacetamide (non-polar diastereomer) (200 mg, 0.38 mmol) in methanol (10 mL) was mixed with 37% hydrochloric acid (10 mL) and stirred for 7 h at 100° C. in a Teflon pressure vessel. Methanol (10 mL) and 37% hydrochloric acid (10 mL) was then added again and the mixture stirred a further 6 h at 100° C. The reaction solution was then concentrated to low volume in a vacuum and the residue (250 mg) purified by flash chromatography (37 g, 20×2.1 cm) with dichloromethane/methanol [8:2+1% NH$_3$ (32% in H$_2$O)].

Example 27

Non-Polar Diastereomer

Yield: 98 mg (60%), amorphous beige-coloured solid
$^1$H-NMR (DMSO-d$_6$): 1.35-2.00 (m, 8H); 2.11 (s, 6H); 2.55 (s, 1H); 3.46 (d, 2H, J=4.0 Hz); 4.61 (s, 1H); 6.85 (s, 1H); 6.95 (t, 1H, J=7.5 Hz); 7.03 (t, 1H, J=7.5 Hz); 7.10-7.80 (m, 9H); 10.82 (s, 1H).

LC-MS (method 8): [M+H]$^+$: m/z=430.3, R$_t$=1.6 min.

Step 5

N-[1-cyano-2-(1H-indol-3-yl)ethyl]-N-(4-dimethylamino-4-phenylcyclohexyl)-2,2,2-trifluoroacetamide (polar diastereomer)

2-(4-dimethylamino-4-phenylcyclohexylamino)-3-(1H-indol-3-yl)propionamide (polar diastereomer) (1.58 g, 3.92 mmol) was mixed with anhydrous pyridine (20 mL) and dissolved by stirring with reflux. The solution was cooled to room temperature and mixed with anhydrous dichloromethane (20 mL) and triethylamine (6 mL), then cooled to −15° C. and mixed with trifluoroacetic anhydride (2.48 g, 1.64 mL, 11.8 mmol). The mixture was stirred for 3 h at −15° C. The solvent was then removed in a vacuum. The residue was repeatedly mixed with toluol and the solution again concentrated to low volume in a vacuum each time. The residue was dissolved in ethyl acetate (20 mL) and washed with sodium hydrogencarbonate solution (3×20 mL). The organic phase was dried with sodium sulphate and concentrated to low volume in a vacuum. The raw product (1.6 g) was purified by flash chromatography (120 g, 20×4.1 cm) with dichloromethane/methane [95:5+1% NH$_3$ (32% in H$_2$O)].

Yield: 693 mg (37%), yellowish solid
Melting point: 248° C.
$^1$H-NMR (DMSO-d$_6$): 0.98-1.07 (m, 2H); 1.22-1.72 (m, 4H); 1.86 (s, 6H); 2.43-2.50 (m, 1H); 2.73 (brd, 1H; J=10.9 Hz); 3.20 (dd, 1H, J=14.0, 7.5 Hz); 3.45 (dd, 1H, J=14.0, 8.2 Hz); 3.73 (m, 1H); 3.99 (t, 1H, J=7.8 Hz); 6.99 (t, 1H, J=7.0 Hz); 7.06-7.15 (m, 3H); 7.24 (d, 2H, J=7.8 Hz); 7.35 (t, 2H, J=7.8 Hz); 7.43 (t, 2H, J=7.6 Hz); 11.02 (s, 1H).

$^{13}$C-NMR (DMSO-d$_6$): 25.4; 25.9; 26.5; 30.7; 31.6; 38.0; 45.0; 45.6; 57.8; 60.1; 106.9; 111.6; 115.7 (q, J=287 Hz); 116.6; 117.6; 118.8; 121.2; 124.7; 126.5; 126.6; 127.7; 127.9; 135.3; 136.0; 155.6 (q, J=36 Hz).

LC-MS (method 8): [M+H]$^+$: m/z=483.3, R$_t$=2.3 min.

Step 6

N-(2-(1H-indol-3-yl)-1-(1H-tetrazol-5-yl)ethyl)-N-(4-dimethylamino-4-phenylcyclohexyl)-2,2,2-trifluoroacetamide (Example 28, polar-diastereomer)

A solution of N-[1-cyano-2-(1H-indol-3-yl)ethyl]-N-(4-dimethylamino-4-phenylcyclohexyl)-2,2,2-trifluoroacetamide (polar diastereomer) (613 mg, 1.27 mmol) in N,N-dimethylformamide (5 mL) and toluol (5 mL) was mixed with sodium azide (825 mg, 12.7 mmol) and triethylamine hydrochloride (1.74 g, 12.7 mmol) and stirred for 2 d at 80° C. in a Teflon pressure vessel. The solvent was then concentrated to low volume in a vacuum, the residue repeatedly mixed with toluol and the solution again concentrated to low volume in a vacuum each time. The raw product (1.62 g) was purified by flash chromatography (200 g, 20×4; 1 cm) with dichloromethane/methanol [2:1+1% NH$_3$ (32% in H$_2$O)].

Example 28

Polar Diastereomer

Yield: 615 mg (92%)
Melting point: 195-228° C.
$^1$H-NMR (DMSO-d$_6$): 0.30-2.10 (m, 4H); 2.15 (s, 2H), 2.20-2.30 (m, 1H); 2.35 (4H, s); 2.64-3.00 (m, 2H); 3.24 (dd, 1H, J=4.5 and 13.6 Hz); 3.50-3.75 (m, 1H); 3.85 (dd, 1H J=13.9, 10.2 Hz); 3.99 (m, 0.67H); 4.25 (m, 0.33H); 5.32 (dd, 1H, J=9.9, 4.2 Hz); 6.80 (d, 0.67H, J=2.0 Hz); 6.87 (d, 0.33H, J=2.0 Hz); 6.92-7.62 (m, 10H); 10.77 (s, 0.66H); 10.92 (m, 0.33H).

LC-MS (method 8): [M+H]$^+$: m/z=526.3, R$_t$=2.2 min.

Step 7

N$^4$-(2-(1H-indol-3-yl)-1-(1H-tetrazol-5-yl)ethyl)-N$^1$, N$^1$-dimethyl-1-phenylcyclohexane-1,4-diamine (Example 29, polar diastereomer)

A suspension of N-(2-(1H-indol-3-yl)-1-(1H-tetrazol-5-yl)ethyl)-N-(4-dimethylamino-4-phenylcyclohexyl)-2,2,2-trifluoroacetamide (100 mg, 0.19 mmol) in methanol (10 mL) was mixed with 37% hydrochloric acid (3 mL) and stirred for 7 h at 100° C. in a Teflon pressure vessel. 37% hydrochloric acid (3 mL) was then added again, the mixture stirred for a further 24 h at 100° C. and then concentrated to low volume in a vacuum. The raw product was purified by flash chromatography (85 g, 20×3.6 cm) with dichloromethane/methanol [2:1+1% NH$_3$ (32% in H$_2$O)].

Example 29

Polar Diastereomer

Yield: 43 mg (53%)
Melting point: 190-195° C.
$^1$H-NMR (DMSO-d$_6$): 1.00-1.44 (m, 6H); 1.73 (br d, 2H, J=10.6 Hz); 1.88 (s, 6H); 2.08 (br d, 1H, J=12.1 Hz); 2.52-2.72 (m, 2H); 3.31 (dd, 1H, J=13.7, 4.3 Hz); 3.36-3.48 (m, 1H); 4.63 (dd, 1H, J=9.8, 4.4 Hz); 6.73 (d, 1H, J=2.3 Hz); 6.93

(ddd, 1H, J=7.9, 7.1, 1.1H); 7.02 (ddd, 1H, J=8.0, 7.1, 1.1 Hz); 7.247.55 (m, 7H); 10.75 (s, 1H).

$^{13}$C-NMR (DMSO-$d_6$): 24.6; 26.3; 28.6; 30.4; 30.5; 37.8; 51.6; 53.8; 60.9; 108.8; 111.3; 117.7; 118.3; 120.7; 123.5; 12-6.5; 126.9; 127.7; 127.9; 135.6; 135.7; 157.3.

LC-MS (method 8): [M+H]$^+$: m/z=420.3, $R_f$=1.0 min.

Studies on the Efficacy of the Compounds According to the Invention

Measurement of the ORL 1-Bond

The compounds were examined with membranes of recombinant CHO-ORL 1 cells in a receptor binding assay with $^3$H-nociceptin/orphanin FQ. This test system was conducted in accordance with the method outlined by Ardati et al. (Mol. Pharmacol., 51, 1997, pp. 816-824). The concentration of $^3$H-nociceptin/orphanin FQ amounted to 0.5 nM in these tests. The binding assays were conducted in each case on 20 µg of membrane protein per 200 µg of preparation in 50 mM of HEPES, pH 7.4, 10 nM of $MgCl_2$ and 1 mM of EDTA. The binding to the ORL 1-receptor was determined using 1 mg of WGA-SPA beads (Amersham-Pharmacia, Freiburg) in each case by incubating the preparation for one hour at RT and then conducting measurements in the Trilux scintillation counter (Wallac, Finland). The affinity is indicated as nanomolar $K_i$ value or in % inhibition at c=1 µM in Table 1.

Measurement of the µ-Bond

The affinity to the human µ-opiate receptor was determined in a homogeneous preparation in microtiter plates. For this, dilution series of the respective compound to be tested were incubated for 90 minutes at room temperature with a receptor membrane preparation (15-40 µg of protein per 250 µl of incubation batch) of CHO-K1 cells, which express the human k opiate receptor (RB-HOM receptor membrane preparation of NEN, Zaventem, Belgium), in the presence of 1 nmol/l of the radioactive ligand [$^3$H']-naloxone (NET719, NEN, Zaventem, Belgium) and of 1 mg WGA-SPA beads (wheat germ agglutinin SPA beads from Amersham/Pharmacia, Freiburg, Germany) in a total volume of 250 µl. 50 mmol/l of tris-HCl supplemented by 0.05% by wt. of sodium azide and 0.06% by wt. of bovine serum albumin was used as incubation buffer. 25 µmol/l of naloxone were additionally added to determine the non-specific bond. After the ninety-minute incubation time had ended, the microtiter plates were centrifuged for 20 minutes at 1000 g and the radioactivity measured in a β-counter (Microbeta-Trilux, PerkinElmer Wallac, Freiburg, Germany). The percentage displacement of the radioactive ligand from its binding to the human L-opiate receptor was determined with a concentration of the test substances of 1 µmol/l and was specified as percentage inhibition (% inhibition) of the specific bond. In some instances, working from the percentage displacement by different concentrations of the compounds of the general formula I according to the invention, $IC_{50}$ inhibition-concentrations were calculated that effect a 50 percent displacement of the radioactive ligand. Ki values for the test substances were obtained by conversion using the Cheng-Prusoff equation. In some cases, the determination of the Ki value was omitted and only the inhibition with a test concentration of 1 µM was determined.

[$^3$H] BTX Binding to the Sodium Channel (Sodium Channel Binding Site 2; BTX Assay)

The [$^3$H] BTX displacement by test substances is tested on synaptosomes (from the cortical tissue in male Sprague Dawley rats, 150-350 g) in the presence of [$^3$H] BTX, TTX and alpha-scorpion venom.

batrachotoxin (BTX) binds to binding site 2 of the $Na^+$-receptor and inhibits the inactivation of the channel there tetrodotoxin (TTX) binds to binding site 2 of the receptor and reduces non-specific binding of BTX there scorpion venom improves the specific binding of BTX to binding site 2 by 20- to 30-fold by specifically binding site 3 veratridine (VTD), like BTX, binds to binding site 2 and therefore competitively inhibits the binding of BTX The tests are conducted with a fixed potassium concentration of 5.4 mM at 37° C. The incubation time amounts to 120 min. Non-specific bonds are determined in the presence of VTD. After the incubation time has elapsed the test plate is aspirated over a filter plate. Receptor molecules remaining in the filter and bonded by [$^3$H] BTX can now be quantified accordingly by measuring the radioactivity, from which findings concerning the displacement of BTX by test substances are provided in turn. Further details can be read in the method part of Catterall et al. (1981).

Literature: Binding of batrachotoxinin A 20-alpha-benzoate to a receptor site associated with sodium channels in synaptic nerve ending particles. Catterall W A, Morrow C S, Daly J W, Brown G B. J Biol. Chem. 1981 Sep. 10; 256(17): 8922-7.

Chung Model: Mononeuropathic Pain after Spinal Nerve Ligature

Animals: Male Sprague Dawley rats (140-160 g) from a commercial breeder (Janvier, Genest St. Isle, France) were held under a 12:12 h light-dark rhythm. The animals were kept with a free choice of feed and tap water. A break of one week was adhered to between delivery of the animals and the operation. The animals were tested multiple times after operation over a period of 4-5 weeks, in which case a wash out time of at least one week was adhered to.

Model description: Under pentobarbital narcosis (Narcoren®, 60 mg/kg i.p., Merial GmbH, Hallbergmoos, Germany), the left L5, L6 spinal nerves were exposed by removing a piece of paravertebral muscle and a portion of the left spinal process of the L5 lumbar vertebral body. The spinal nerves L5 and L6 were carefully isolated and bound with a firm ligature (NC silk black, USP 5/0, metric 1, Braun Melsungen AG, Melsungen, Germany) (Kim and Chung 1992). After ligature the muscle and adjacent tissue were sutured and the wound closed by metal clamps.

After a one-week recovery time the animals are placed in cages with a wire base for measurement of the mechanical allodynia. The pull-away threshold was determined at the ipsi- and/or contralateral rear paw by means of an electronic von Frey filament (Somedic A B, Malmö, Sweden). The median of five stimulations gave a data point. The animals were tested 30 min before application and at various times after application of test substance or vehicle solution. The data were determined as % maximum possible effect (% MPE) from the pre-testing of individual animals (=0% MPE) and the test values of an independent sham control group (=100% MPE). Alternatively the pull-away thresholds were shown in gram.

Statistical evaluation: $ED_{50}$ values and 95% confidence intervals were determined by means of semi-logarithmic regression analysis at the time of maximum effect. The data were analysed by means of a variance analysis with repeated measurements as well as a Bonferroni post hoc analysis procedure. The group size usually amounted to n=10.

References: Kim, S. H. and Chung, J. M.: An experimental model for peripheral neuropathy produced by segmental spinal nerve ligature in the rat, Pain, 50 (1992) 355-363.

Nephelometric Solubility Study (Phosphate Buffer pH 7.4):

This method examines the solubility of a substance with fixed concentrations (1 µM, 3 µM, 10 µM, 30 µM and 100 µM)

in 10 mM of phosphate buffer solution with pH 7.4. A 10 mM solution of the substances in DMSO will be initially required, from which 100-fold stock solutions of the above-mentioned concentration level again in DMSO are produced, the final DMSO concentration in the test batch amounting to 1% (v/v). The experiment is conducted multiple times for determination. After the DMSO stock solutions have been added to the buffer, the batch is incubated for 2 h at 37° C. before an absorption determination at 620 nm occurs. If the absorption of the samples increases above that of the pure buffer/DMSO solution, then this applies as indicator for a precipitate formation. The lower solubility limit ("lower boundary") is the concentration preceding that with the first precipitate formation (e.g. 3 µM if precipitate formation was detected at 10 µM).

Results Table:

| No. | % Inhibition (ORL1) [1 µM] | Ki (ORL1) Mean [µM] | % Inhibition (µ) [1 µM] | Ki (µ) Mean [µM] | SNL. rat. i.v. |
|---|---|---|---|---|---|
| 1 | 83 | 0.019 | 94 | 0.014 | nd |
| 2 | 47 | 0.395 | 65 | 0.730 | nd |
| 3 | 96 | 0.005 | 96 | 0.013 | 26% MPE at 300 µg/kg |
| 4 | 42 | 0.165 | 69 | 0.103 | nd |
| 5 | nd | 0.060 | 72 | 0.195 | nd |
| 7 | nd | 0.052 | 95 | 0.011 | nd |
| 8 | nd | 0.630 | 45 | 1.010 | nd |
| 9 | 92 | 0.006 | 92 | 0.016 | nd |
| 10 | 71 | 0.135 | 91 | 0.480 | nd |
| 11 | 93 | nd | 93 | nd | nd |
| 12 | 91 | 0.008 | 97 | 0.007 | nd |
| 13 | 53 | nd | 80 | nd | nd |
| 14 | 93 | 0.010 | 97 | 0.005 | nd |
| 15 | 61 | 0.320 | 81 | 0.036 | nd |
| 17 | 97 | 0.004 | nd | 0.018 | nd |
| 18 | 60 | nd | 87 | nd | nd |
| 19 | 88 | 0.011 | 96 | 0.009 | nd |
| 20 | 86 | 0.02 | nd | 0.009 | nd |
| 22 | 78 | 0.015 | 98 | 0.01 | nd |
| 23 | 53 | 0.3 | 86 | 0.1 | nd |
| 24 | 92 | nd | 72 | nd | nd |
| 25 | 47 | nd | 46 | nd | nd |
| 26 | 39 | nd | 72 | nd | nd |
| 29 | 26 | 2.8 | nd | 0.34 | nd | nd = not determined

The compounds according to the invention of type E where Z=—NH, R≠H (Ex; 4, 6, 8, 13 and 15) were compared to corresponding compounds of type E where Z=O or —NH, R=H and Me and (C-1 to C-3):

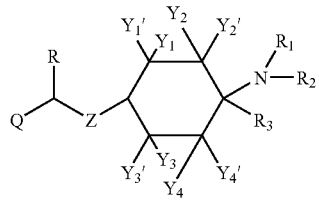

(E)

| No. | Z | R | Diastereomer | Inhibition (BTX) Mean [% at 10 µM] |
|---|---|---|---|---|
| C-1 | —NH— | H | polar | 86 |
| C-2 | —NH— | Me | polar | 62 |
| C-3 | —O— | H | polar | 77 |
| Ex. 4 | —NH— | (C(=O)NH₂) | polar | 29 |
| Ex. 6 | —NH— | (C(=O)N(Me)₂) | polar | 15 |
| Ex. 8 | —NH— | (C(=O)NHMe) | polar | 27 |
| Ex. 13 | —NH— | (oxadiazolone) | polar | 43 |
| Ex. 15 | —NH— | (methyl-oxadiazole) | polar | 41 |

As the above comparison shows, the compounds according to the invention, in particular the respective more polar diastereomer, exhibit a lower affinity to the BTX ion channel compared to structurally similar compounds, which should be associated in particular with advantages with respect to undesirable cardiovascular side-effects.

The compounds according to the invention of type E where Z=—NH, R≠H (Ex; 1, 9, 18 and 20) were compared to compounds of type F where Z=—NH or —NMe, $R_6$=H or Me ($R_1$ to $R_3$, $Y_1$ to $Y_4$ and $Y_1$' to $Y_4$' are each identical) (C-4 to C-6):

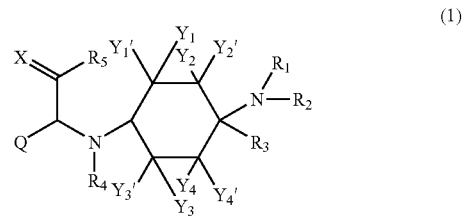

(E)

(F)

| Ex. | R | Z | R$_6$ | Diastereomer | Nephelometry (lower boundary) μM |
|---|---|---|---|---|---|
| 1 | (C(=O)NH$_2$) | NH | not applicable | non-polar | 100 |
| 9 | (oxadiazolone) | NH | not applicable | non-polar | 100 |
| 18 | (oxazole) | NH | not applicable | polar | 100 |
| 20 | (thiazole) | NH | not applicable | non-polar | 100 |
| C-4: | not applicable | NMe | H | non-polar | 3 |
| C-5: | not applicable | NMe | H | polar | 3 |
| C-6: | not applicable | NH | Me | non-polar | 10 |

As the above comparison shows, the compounds according to the invention from Examples 1, 9, 18 and 20 have a better solubility in aqueous media compared to structurally similar compounds (C-4 to C-6), which in particular should be associated with advantages with respect to the resorption properties and/or bioavailability.

The invention claimed is:

1. A compound of the formula (1):

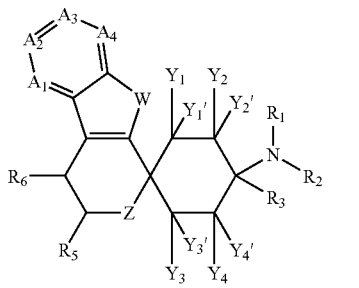

wherein
$Y_1, Y_1', Y_2, Y_2', Y_3, Y_3', Y_4$ and $Y_4'$ are respectively selected independently of one another from the group consisting of —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ and —NHC(=O)N(R$_0$)$_2$; or $Y_1$ and $Y_1'$, or $Y_2$ and $Y_2'$, or $Y_3$ and $Y_3'$, or $Y_4$ and $Y_4'$ jointly stand for =O;

Q stands for —R$_0$;

X stands for =O, =CR$_6$R$_7$ or =N—R$_6$;

R$_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

R$_1$ and R$_2$, independently of one another, stand for —H or —R$_0$; or R$_1$ and R$_2$ together stand for —CH$_2$CH$_2$OCH$_2$CH$_2$—, —(CH$_2$)$_{3-6}$— or —CH$_2$CH$_2$NR'CH$_2$CH$_2$— with R'=—H, —R$_0$ or —C(=O)R$_0$;

R$_3$ stands for —R$_0$;

R$_4$ stands for —H, —C(=O)R$_0$ or —R$_0$;

R$_5$ stands for —H, —F, —Cl, —Br, —I, —CN, —NO$_2$, —CHO, —R$_0$, —C(=O)H, —C(=O)R$_0$, —C(=O)OH, —C(=O)OR$_0$, —C(=O)NH$_2$, —C(=O)NHR$_0$, —C(=O)N(R$_0$)$_2$, —N(R$_0$)$_2$, —N$^+$(R$_0$)$_3$, —N$^+$(R$_0$)$_2$O$^-$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$ or —NHC(=O)N(R$_0$)$_2$;

R$_6$ and R$_7$ respectively independently stand for —H, —F, —Cl, —Br, —I, —CN, —NO$_2$, —CHO, —R$_0$, —C(=O)H, —C(=O)R$_0$, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$ or —NHC(=O)N(R$_0$)$_2$;

or R$_5$ and R$_6$ jointly form a five- or six-membered ring, the other ring atoms of which respectively independently of one another are C, N, S or O, wherein the ring is aromatic or non-aromatic, unsubstituted or mono- or polysubstituted by substituents selected independently of one another from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$ and —NH—C(=O)N(R$_0$)$_2$;

wherein

"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue;

wherein with respect to "aliphatic" and "cycloaliphatic", "mono- or polysubstituted" means the mono- or polysubstitution of one or more hydrogen atoms by substituents selected independently of one another from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$, —NHC(=O)N(R$_0$)$_2$, —Si(R$_0$)$_3$ and —PO(OR$_0$)$_2$;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" means the mono- or polysubstitution of one or more hydrogen atoms of the ring system by substituents selected from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)—N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NH—C(=O)NH$_2$, —NHC(=O)NHR$_0$, —NHC(=O)N(R$_0$)$_2$, —Si(R$_0$)$_3$, —PO(OR$_0$)$_2$;

wherein any N-ring atoms present can be respectively oxidised;

said compound being in the form of a single stereoisomer or mixture thereof, the free compound and/or a physiologically compatible salt thereof.

2. Compound according to claim 1, which has the formula (1.1) or (1.2):

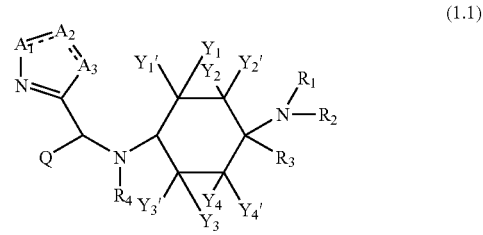

(1.1)

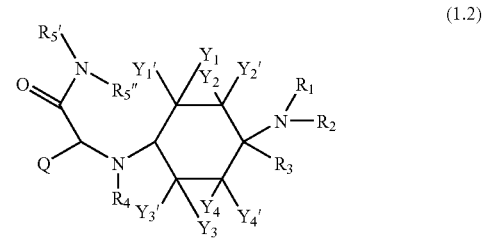

(1.2)

wherein, where present,

A$_1$ stands for —N=, —NH—, —NR$_8$— or —CR$_8$=;

A$_2$ stands for =N—, —C(=O)— or =CR$_9$—;

A$_3$ stands for —O—, —NH— or —NR$_{10}$—; and

R$_5$', R$_5$", R$_8$, R$_9$ and R$_{10}$ respectively independently of one another stand for —H, =O or —C$_{1-8}$-aliphatic.

3. Compound according to claim 1, which has the formula (2), (3), (4), (5) or (6):

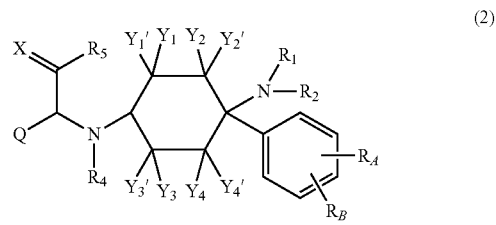

(2)

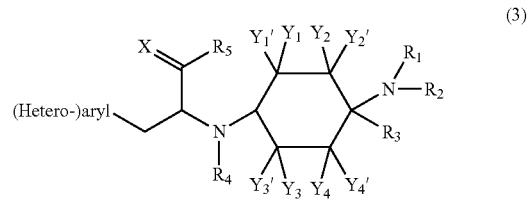

(3)

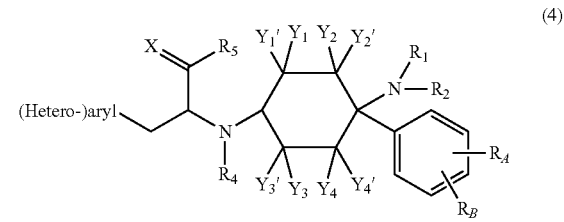

(4)

-continued (5)

(6)

wherein, where present, $R_A$, $R_B$, $R_C$ and $R_D$ are respectively selected independently of one another from the group consisting of —H, —$C_{1-8}$-aliphatic, —OH, —$OC_{1-8}$-aliphatic, —$CF_3$, —F, —Cl, —Br, —$NO_2$, —CN, -heteroaryl, —$C_{1-8}$-aliphatic-aryl and —$C_{1-8}$-aliphatic-heteroaryl; and (hetero)aryl stands for -heteroaryl or -aryl.

4. Compound according to claim 1, which is selected from the group consisting of:

- (S)-2-(4-(dimethylamino)-4-phenylcyclohexylamino)-3-(1H-indol-3-yl)propanamide;
- (S)-2-(4-(dimethylamino)-4-phenylcyclohexylamino)-3-(1H-indol-3-yl)propanamide;
- (±)-2-(4-(dimethylamino)-4-phenylcyclohexylamino)-3-(1H-indol-3-yl)propanamide;
- (±)-2-(4-(dimethylamino)-4-phenylcyclohexylamino)-3-(1H-indol-3-yl)propanamide;
- (S)-2-(4-(dimethylamino)-4-phenylcyclohexylamino)-3-(1H-indol-3-yl)-N,N-dimethylpropanamide;
- (S)-2-(4-(dimethylamino)-4-phenylcyclohexylamino)-3-(1H-indol-3-yl)-N,N-dimethylpropanamide;
- (S)-2-(4-(dimethylamino)-4-phenylcyclohexylamino)-3-(1H-indol-3-yl)-N-methylpropanamide;
- (S)-2-(4-(dimethylamino)-4-phenylcyclohexylamino)-3-(1H-indol-3-yl)-N-methylpropanamide;
- 5-((S)-1-(4-(dimethylamino)-4-phenylcyclohexylamino)-2-(1H-indol-3-yl)ethyl)-1,3,4-oxadiazol-2(3H)-one;
- 5-((S)-1-(4-(dimethylamino)-4-phenylcyclohexylamino)-2-(1H-indol-3-yl)ethyl)-1,3,4-oxadiazol-2(3H)-one;
- N4-((S)-2-(1H-indol-3-yl)-1-(3-methyl-1,2,4-oxadiazol-5-yl)ethyl)-N1,N1-dimethyl-1-phenylcyclohexane-1,4-diamine;
- 5-((R)-1-(4-(dimethylamino)-4-phenylcyclohexylamino)-2-(1H-indol-3-yl)ethyl)-1,3,4-oxadiazol-2(3H)-one;
- 5-((R)-1-(4-(dimethylamino)-4-phenylcyclohexylamino)-2-(1H-indol-3-yl)ethyl)-1,3,4-oxadiazol-2(3H)-one;
- N4-((R)-2-(1H-indol-3-yl)-1-(3-methyl-1,2,4-oxadiazol-5-yl)ethyl)-N1,N1-dimethyl-1-phenylcyclohexane-1,4-diamine;
- N4-((R)-2-(1H-indol-3-yl)-1-(3-methyl-1,2,4-oxadiazol-5-yl)ethyl)-N1,N1-dimethyl-1-phenylcyclohexane-1,4-diamine;
- N4-((S)-2-(1H-indol-3-yl)-1-(5-methyloxazol-2-yl)ethyl)-N1,N1-dimethyl-1-phenylcyclohexane-1,4-diamine;
- N4-((S)-2-(1H-indol-3-yl)-1-(5-methyloxazol-2-yl)ethyl)-N1,N1-dimethyl-1-phenylcyclohexane-1,4-diamine;
- N4-(2-(1H-indol-3-yl)-1-(1H-tetrazol-5-yl)ethyl)-N1,N1-dimethyl-1-phenylcyclohexane-1,4-diamine;
- N4-(2-(1H-indol-3-yl)-1-phenylethyl)-N1,N1-dimethyl-1-phenylcyclohexane-1,4-diamine;
- N4-(2-(1H-indol-3-yl)-1-(1H-tetrazol-5-yl)ethyl)-N1,N1,N4-trimethyl-1-phenyl-cyclohexane-1,4-diamine;
- N4-(2-(1H-indol-3-yl)-1-phenylethyl)-N1,N1,N4-trimethyl-1-phenylcyclohexane-1,4-diamine;
- N4-(2-(1H-indol-3-yl)-1-(3-methyl-1,2,4-oxadiazol-5-yl)ethyl)-N1,N1,N4-trimethyl-1-phenylcyclohexane-1,4-diamine;
- N4-(2-(1H-indol-3-yl)-1-(5-methyloxazol-2-yl)ethyl)-N1,N1,N4-trimethyl-1-phenylcyclohexane-1,4-diamine;
- 5-(1-((4-(dimethylamino)-4-phenylcyclohexyl)(methyl)amino)-2-(1H-indol-3-yl)ethyl)-1,3,4-oxadiazol-2(3H)-one;
- 2-((4-(dimethylamino)-4-phenylcyclohexyl) (methyl)amino)-3-(1H-indol-3-yl)-N,N-dimethylpropanamide;
- N4-(2-(1H-indol-3-yl)-1-(3-methyl-1,2,4-oxadiazol-5-yl)ethyl)-1-(3-fluorophenyl)-N1,N1-dimethylcyclohexane-1,4-diamine;
- N4-(2-(1H-indol-3-yl)-1-(5-methyloxazol-2-yl)ethyl)-1-(3-fluorophenyl)-N1,N1-dimethylcyclohexane-1,4-diamine;
- N-(2-(1H-indol-3-yl)-1-(5-methyloxazol-2-yl)ethyl)-N-(4-(dimethylamino)-4-(3-fluorophenyl)cyclohexyl)cinnamic acid amide; and
- N-(2-(1H-indol-3-yl)-1-(3-methyl-1,2,4-oxadiazol-5-yl)ethyl)-N-(4-(dimethylamino)-4-(3-fluorophenyl)cyclohexyl)cinnamic acid amide;
- (R)—N4-(2-(1H-indol-3-yl)-1-(5-methyloxazol-2-yl)ethyl)-N1,N1-dimethyl-1-phenylcyclohexane-1,4-diamine;
- (S)—N4-(2-(1H-indol-3-yl)-1-(4-methylthiazol-2-yl)ethyl)-N1,N1-dimethyl-1-phenylcyclohexane-1,4-diamine;
- (R)—N4-(2-(1H-indol-3-yl)-1-(4-methylthiazol-2-yl)ethyl)-N1,N1-dimethyl-1-phenylcyclohexane-1,4-diamine;
- N4-(2-(1H-indol-3-yl)-1-phenylethyl)-N1,N1-dimethyl-1-phenylcyclohexane-1,4-diamine dihydrochloride;
- N-(2-(1H-indol-3-yl)-1-(1H-tetrazol-5-yl)ethyl)-N-(4-dimethylamino-4-phenylcyclohexyl)-2,2,2-trifluoroacetamide; and
- N4-(2-(1H-indol-3-yl)-1-(1H-tetrazol-5-yl)ethyl)-N1,N1-dimethyl-1-phenylcyclohexane-1,4-diamine;

and physiologically compatible salts thereof.

5. A pharmaceutical composition comprising at least one compound according to claim 1, said compound being in the form of a single stereoisomer or mixture thereof, the free compound and/or a physiologically compatible salt thereof, and optionally suitable additives and/or adjuvants and/or further active substances.

6. A method of treating pain in a patient in need of such treatment, said method comprising administering to said patient an effective amount therefor of a compound according to claim 1, said compound being in the form of a single stereoisomer or mixture thereof, the free compound and/or a physiologically compatible salt thereof.

7. A method of treating a condition in a patient in need of such treatment, said method comprising administering to said patient an effective amount therefor of a compound according to claim 1, said compound being in the form of a single stereoisomer or mixture thereof, the free compound and/or a physiologically compatible salt and/or solvate thereof, wherein said condition is selected from the group consisting of anxiety conditions, stress and stress-related syndromes, depressive illnesses, epilepsy, Alzheimer's disease, senile dementia, general cognitive dysfunctions, learning and memory disabilities (as nootropic), withdrawal symptoms, alcohol and/or drug and/or medication misuse and/or dependence, sexual dysfunctions, cardiovascular diseases, hypotension, hypertension, tinitus, pruritus, migraine, hearing impairment, deficient intestinal motility, eating disorders, anorexia, bulimia, mobility disorders, diarrhoea, cachexia, urinary incontinence, or as muscle relaxant, anticonvulsive or anaesthetic, or wherein said administering is for coadministration in the treatment with an opioid analgesic or with an anaesthetic, for diuresis or anti-natriuresis, anxiolysis, for modulating movement activity, for modulating neurotransmitter release and for treating neuro-degenerative diseases associated therewith, for treating withdrawal symptoms and/or for reducing the addiction potential of opioids.

* * * * *